(12) United States Patent
Taggi et al.

(10) Patent No.: US 10,015,966 B2
(45) Date of Patent: **\*Jul. 10, 2018**

(54) FUNGICIDAL PYRAZOLE MIXTURES

(71) Applicant: E I DU PONT DE NEMOURS AND COMPANY, Wilmington, DE (US)

(72) Inventors: Andrew Edmund Taggi, Newark, DE (US); Jeffrey Keith Long, Wilmington, DE (US); James Francis Bereznak, Newtown Square, PA (US)

(73) Assignee: E I DU PONT DE NEMOURS AND COMPANY, Wilmington, DE (US)

( \* ) Notice: Subject to any disclaimer, the term of this patent is extended or adjusted under 35 U.S.C. 154(b) by 0 days.

This patent is subject to a terminal disclaimer.

(21) Appl. No.: 14/374,315

(22) PCT Filed: Jan. 30, 2013

(86) PCT No.: PCT/US2013/023703
§ 371 (c)(1),
(2) Date: Jul. 24, 2014

(87) PCT Pub. No.: WO2013/116251
PCT Pub. Date: Aug. 8, 2013

(65) Prior Publication Data
US 2015/0018374 A1 Jan. 15, 2015

Related U.S. Application Data

(60) Provisional application No. 61/593,540, filed on Feb. 1, 2012, provisional application No. 61/662,149, filed on Jun. 20, 2012.

(51) Int. Cl.
| | | |
|---|---|---|
| *A01N 43/56* | (2006.01) |
| *C07C 323/29* | (2006.01) |
| *C07C 331/28* | (2006.01) |
| *C07C 255/40* | (2006.01) |
| *A01N 37/18* | (2006.01) |
| *A01N 43/10* | (2006.01) |
| *A01N 43/40* | (2006.01) |
| *A01N 43/54* | (2006.01) |
| *A01N 43/60* | (2006.01) |
| *A01N 43/90* | (2006.01) |
| *A01N 47/18* | (2006.01) |

(52) U.S. Cl.
CPC ............ *A01N 43/56* (2013.01); *A01N 37/18* (2013.01); *A01N 43/10* (2013.01); *A01N 43/40* (2013.01); *A01N 43/54* (2013.01); *A01N 43/60* (2013.01); *A01N 43/90* (2013.01); *A01N 47/18* (2013.01); *C07C 255/40* (2013.01); *C07C 323/29* (2013.01); *C07C 331/28* (2013.01)

(58) Field of Classification Search
CPC ...................................................... A01N 43/56
See application file for complete search history.

(56) References Cited

U.S. PATENT DOCUMENTS

| 5,849,778 A | 12/1998 | Heil et al. |
| 6,087,381 A | 7/2000 | Hanson et al. |
| 2009/0156592 A1 | 6/2009 | Pasteris |
| 2010/0016396 A1 | 1/2010 | Imoto |

FOREIGN PATENT DOCUMENTS

| JP | 8208620 A | 8/1996 |
| WO | 9319054 A1 | 9/1993 |
| WO | 2004050650 A1 | 6/2004 |
| WO | 2004050651 A1 | 6/2004 |
| WO | 2007027842 A1 | 3/2007 |
| WO | 2008093639 A1 | 7/2008 |
| WO | 2009137538 A2 | 11/2009 |
| WO | 2009137651 A2 | 11/2009 |
| WO | 2010101973 A1 | 9/2010 |
| WO | WO 2010123791 A1 \* | 10/2010 |
| WO | 2012024586 A1 | 2/2012 |
| WO | 2012030922 A1 | 3/2012 |
| WO | 2012031061 A2 | 3/2012 |
| WO | WO 2012031061 A2 \* | 3/2012 |

OTHER PUBLICATIONS

Pfeiffer et al., Synthesis and Reactivity of 6H-1,3,4-Selenadiazines, Pharmazie, 1993, vol. 48, No. 10, pp. 732-735.

\* cited by examiner

*Primary Examiner* — Timothy P Thomas
(74) *Attorney, Agent, or Firm* — Charlene Gross Sternberg

(57) ABSTRACT

Disclosed is a fungicidal composition comprising (a) at least one compound selected from the compounds of Formula 1, N-oxides, and salts thereof,

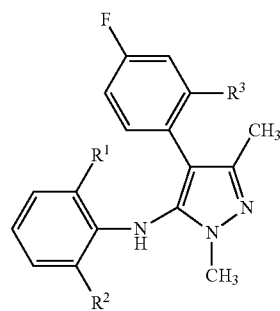

wherein
R¹ is F, Cl or Br;
R² is H or F; and
R³ is Cl or Br; and
(b) at least one fungicidal compound selected from (b1) through (b13) as disclosed herein. Also disclosed is a method for controlling plant diseases caused by fungal plant pathogens comprising applying to the plant or portion thereof, or to the plant seed, a fungicidally effective amount of a compound of Formula 1, an N-oxide, or salt thereof (e.g., as a component in the aforesaid composition). Also disclosed are process intermediate compounds useful for preparing compounds of Formula 1.

3 Claims, No Drawings

FUNGICIDAL PYRAZOLE MIXTURES

FIELD OF THE INVENTION

This invention relates to certain pyrazole derivatives, their N-oxides and salts, to process intermediates for their preparation and to mixtures and compositions comprising such pyrazole derivatives and methods for using such pyrazole derivatives and their mixtures and compositions as fungicides.

BACKGROUND OF THE INVENTION

The control of plant diseases caused by fungal plant pathogens is extremely important in achieving high crop efficiency. Plant disease damage to ornamental, vegetable, field, cereal and fruit crops can cause significant reduction in productivity and thereby result in increased costs to the consumer. In addition to often being highly destructive, plant diseases can be difficult to control and may develop resistance to commercial fungicides. Many products are commercially available for these purposes, but the need continues for new fungicidal compounds which are more effective, less costly, less toxic, environmentally safer or have different sites of action. Besides introduction of new fungicides, combinations of fungicides are often used to facilitate disease control, to broaden spectrum of control and to retard resistance development. Furthermore, certain rare combinations of fungicides demonstrate a greater-than-additive (i.e. synergistic) effect to provide commercially important levels of plant disease control. The advantages of particular fungicide combinations are recognized in the art to vary, depending on such factors as the particular plant species and plant disease to be treated, and whether the plants are treated before or after infection with the fungal plant pathogen. Accordingly new advantageous combinations are needed to provide a variety of options to best satisfy particular plant disease control needs. Such combinations have now been discovered. U.S. Patent Publication US 2011/0319430 A1 discloses certain fungicidal pyrazoles, but does not disclose the fungicidal mixtures of the present invention.

SUMMARY OF THE INVENTION

This invention relates to a fungicidal composition (i.e. combination, mixture) comprising (a) at least one compound selected from the compounds of Formula 1 (including all stereoisomers), N-oxides, and salts thereof:

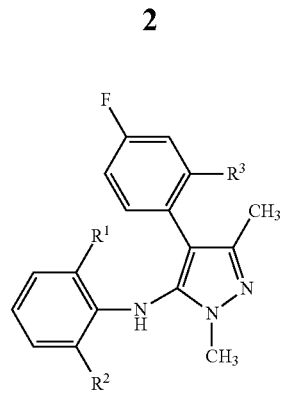

wherein
  $R^1$ is F, Cl or Br;
  $R^2$ is H or F; and
  $R^3$ is Cl or Br; and (b) at least one fungicidal compound selected from (b1)

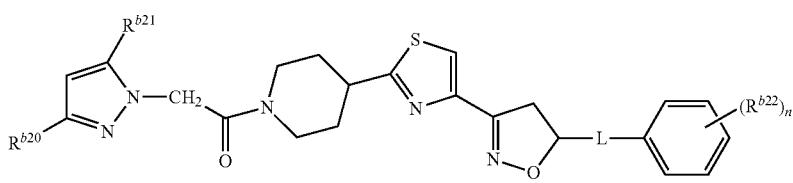

wherein $R^{b20}$ and $R^{b21}$ are independently $CH_3$, $CF_2H$ or $CF_3$; each $R^{b22}$ is independently halogen or cyano; n is 0, 1, 2 or 3; and L is a direct bond or —$CH_2O$— wherein the left bond is connected to the dihydroisoxazole ring and the right bond is connected to the phenyl ring (in Formula B1);

(b2)

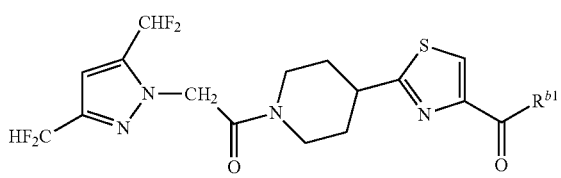

wherein $R^{b1}$ is

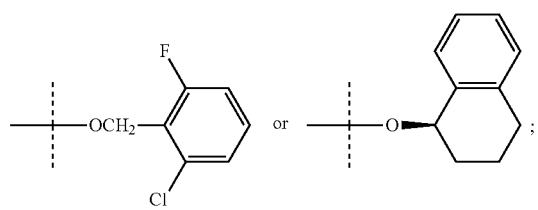

-continued (b3)

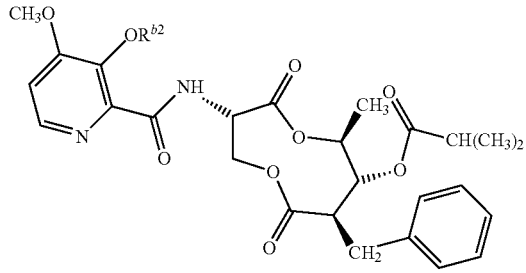
B3 wherein R$^{b2}$ is —CH$_2$OC(O)CH(CH$_3$)$_2$, —C(O)CH$_3$, —CH$_2$OC(O)CH$_3$, —C(O)OCH$_2$CH(CH$_3$)$_2$ or

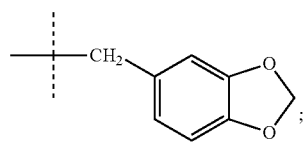
;

(b4)

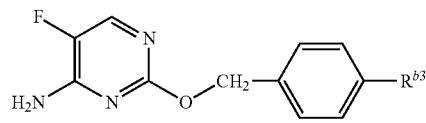
B4 wherein R$^{b3}$ is CH$_3$ or F;

(b5)

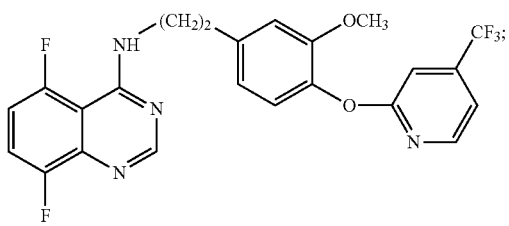
B5

(b6)

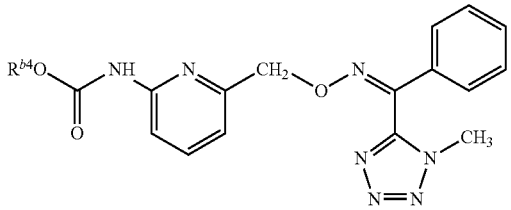
B6 wherein R$^{b4}$ is —(CH$_2$)$_4$CH$_3$, —C(CH$_3$)$_3$ or —(CH$_2$)$_2$C≡CH;

(b7)

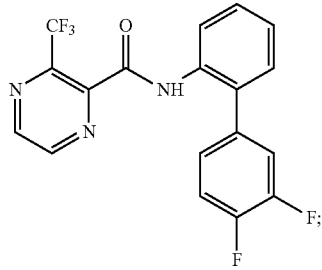
B7

(b8)

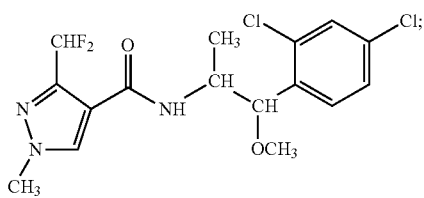
B8

(b9)

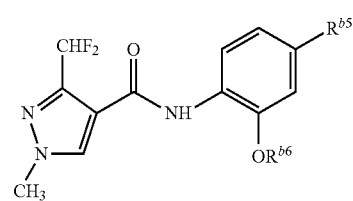
B9 wherein R$^{b5}$ is H or F, and R$^{b6}$ is —CF$_2$CHFCF$_3$ or —CF$_2$CF$_2$H;

(b10)

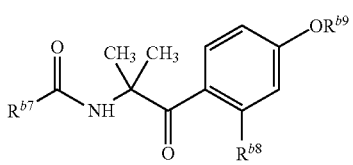
B10 wherein
R$^{b7}$ is

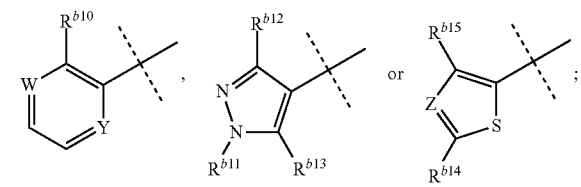

R$^{b8}$ is H, halogen or C$_1$-C$_2$ alkyl;
R$^{b9}$ is C$_1$-C$_8$ alkyl, C$_1$-C$_8$ haloalkyl or C$_2$-C$_8$ alkoxyalkyl;
R$^{b10}$ is halogen, C$_1$-C$_2$ alkyl or C$_1$-C$_2$ haloalkyl;
R$^{b11}$ is halogen, C$_1$-C$_2$ alkyl or C$_1$-C$_2$ haloalkyl;
R$^{b12}$ is C$_1$-C$_2$ alkyl;
R$^{b13}$ is H, halogen or C$_1$-C$_2$ alkyl;
R$^{b14}$ is C$_1$-C$_2$ alkyl or C$_1$-C$_2$ haloalkyl;

$R^{b15}$ is H, $C_1$-$C_2$ alkyl or $C_1$-$C_2$ haloalkyl;
W is CH or N;
Y is CH or N; and
Z is CH or N;

(b10a)

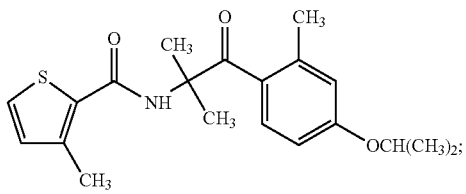

(b10b)

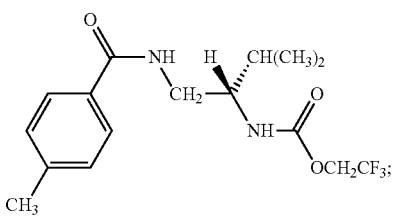

(b11)

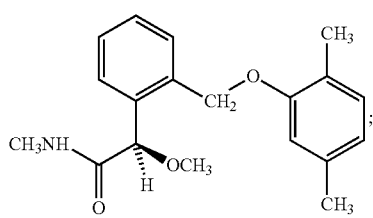

(b12)

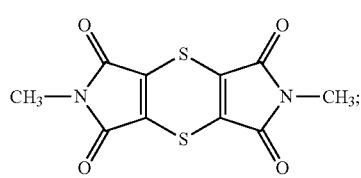

(b13)

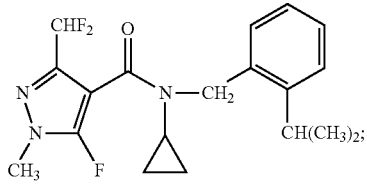

and salts thereof.

This invention also relates to a fungicidal composition comprising: (a) at least one compound selected from the compounds of Formula 1, (b) at least one fungicidal compound selected from Formulae B1 through B13 and salts thereof described above, and further comprising (c) at least one additional compound or agent that is biologically active.

This invention also relates to a composition comprising one of the aforesaid compositions comprising components (a) and (b) and at least one additional component selected from the group consisting of surfactants, solid diluents and liquid diluents.

This invention also relates to a method for controlling plant diseases caused by fungal plant pathogens comprising applying to the plant or portion thereof, or to the plant seed, a fungicidally effective amount of one of the aforesaid compositions.

The aforedescribed method can also be described as a method for protecting a plant or plant seed from diseases caused by fungal pathogens comprising applying a fungicidally effective amount of one of the aforesaid compositions to the plant (or portion thereof) or plant seed (directly or through the environment (e.g., growing medium) of the plant or plant seed).

This invention also relates to a compound of Formula 1 described above, or an N-oxide or salt thereof. This invention further relates to a fungicidal composition comprising a compound of Formula 1, or an N-oxide or salt thereof, and at least one additional component selected from the group consisting of surfactants, solid diluents and liquid diluents. This invention also further relates to a method for protecting a plant or plant seed from diseases caused by fungal pathogens comprising a fungicidally effective amount of a compound of Formula 1, or an N-oxide or salt thereof, to the plant or plant seed.

This invention further relates to a compound of Formula 14,

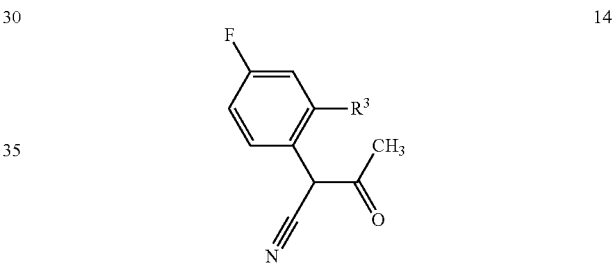

wherein $R^3$ is Cl or Br.

This invention further relates to a compound of Formula 17,

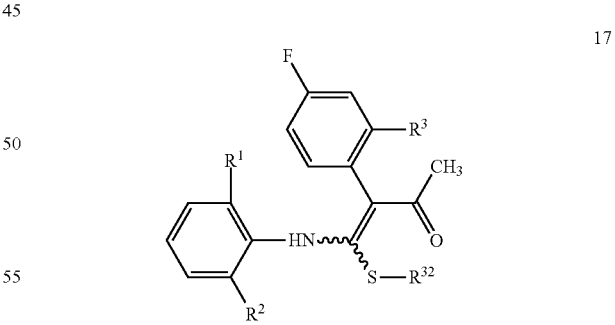

wherein
$R^1$ is F, Cl or Br;
$R^2$ is H or F;
$R^3$ is Cl or Br; and
$R^{32}$ is H, $CH_3$, $CH_2CH_3$ or $(CH_2)_2CH_3$; particularly provided that when $R^1$ is H, or when $R^1$ and $R^2$ are each F, then $R^{32}$ is H.

This invention further relates to a compound of Formula 20,

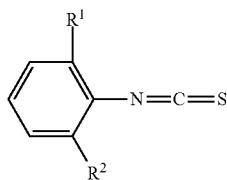

wherein $R^1$ is F, Cl or Br, and $R^2$ is H or F, particularly wherein $R^1$ is Br and $R^2$ is F.

This invention further relates to a compound of Formula 22,

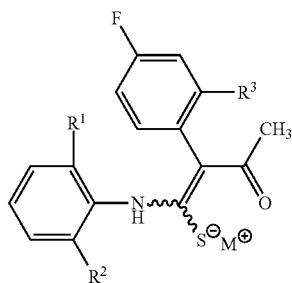

wherein $R^1$ is F, Cl or Br; $R^2$ is H or F; $R^3$ is Cl or Br; and M is Na or K.

Compounds of Formulae 14, 17, 20 and 22 can be used as process intermediates to prepare compounds of Formula 1, which are useful as component (a) in the present compositions.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

The term "Registry Number" refers to Chemical Abstracts Registry Number.

A single bond drawn as a wavy line (e.g., in Formulae 17 and 22) denote that either the E or Z isomer or a mixture of E and Z isomers may be present. A dashed line perpendicularly traversing a bond denotes that the bond connects the substituent fragment to the remainder of a molecule (e.g., $R^{b1}$ in Formula B2).

Compounds relevant to the compositions and methods of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds in the compositions of this invention may be present as a mixture of stereoisomers, individual stereoisomers or as an optically active form.

Synthetic methods for the preparation of N-oxides of heterocycles such as pyrazoles are very well known by one skilled in the art including the oxidation of heterocycles with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in*

*Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 alone and in mixtures are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. Accordingly, the present invention relates to mixtures of compounds selected from Formula 1, N-oxides and agriculturally suitable salts thereof. Also, biologically similar salt forms can exist for many of the compounds of Formulae B1 through B13.

Compounds selected from Formula 1, stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures. Compounds of Formulae B1 through B13, including salts thereof, can also typically exist in more than one form.

In the embodiments of the present invention, including those described below, reference to Formula 1 includes N-oxides and salts thereof unless otherwise indicated, and reference to "a compound of Formula 1" includes the definitions of substituents specified in the Summary of the Invention unless further defined in the Embodiments. Furthermore, reference to Formulae B1 through B13 includes salts thereof unless otherwise indicated.

Embodiment 1

A composition comprising components (a) and (b) described in the Summary of the Invention wherein in Formula 1, $R^2$ is F.

Embodiment 2

A composition comprising components (a) and (b) described in the Summary of the Invention wherein in Formula 1, $R^2$ is H.

Embodiment 3

A composition comprising components (a) and (b) described in the Summary of the Invention or Embodiment 1 or 2 wherein component (a) does not comprise an N-oxide of a compound of Formula 1.

Embodiment 4

A composition comprising components (a) and (b) described in the Summary of the Invention or Embodiment 3 wherein component (a) comprises a compound selected from the group consisting of
4-(2-chloro-4-fluorophenyl)-N-(2-fluorophenyl)-1,3-dimethyl-1H-pyrazol-5-amine (Compound 1),
4-(2-chloro-4-fluorophenyl)-N-(2-chlorophenyl)-1,3-dimethyl-1H-pyrazol-5-amine (Compound 10),
N-(2-bromophenyl)-4-(2-chloro-4-fluorophenyl)-1,3-dimethyl-1H-pyrazol-5-amine (Compound 9),
4-(2-bromo-4-fluorophenyl)-N-(2-fluorophenyl)-1,3-dimethyl-1H-pyrazol-5-amine (Compound 12),
4-(2-bromo-4-fluorophenyl)-N-(2-chlorophenyl)-1,3-dimethyl-1H-pyrazol-5-amine (Compound 8),
4-(2-bromo-4-fluorophenyl)-N-(2-bromophenyl)-1,3-dimethyl-1H-pyrazol-5-amine (Compound 6),
4-(2-chloro-4-fluorophenyl)-N-(2,6-difluorophenyl)-1,3-dimethyl-1H-pyrazol-5-amine (Compound 2),
4-(2-chloro-4-fluorophenyl)-N-(2-chloro-6-fluorophenyl)-1,3-dimethyl-1H-pyrazol-5-amine (Compound 3),
N-(2-bromo-6-fluorophenyl)-4-(2-chloro-4-fluorophenyl)-1,3-dimethyl-1H-pyrazol-5-amine (Compound 5),
4-(2-bromo-4-fluorophenyl)-N-(2,6-difluorophenyl)-1,3-dimethyl-1H-pyrazol-5-amine (Compound 11),
4-(2-bromo-4-fluorophenyl)-N-(2-chloro-6-fluorophenyl)-1,3-dimethyl-1H-pyrazol-5-amine (Compound 4), and
4-(2-bromo-4-fluorophenyl)-N-(2-bromo-6-fluorophenyl)-1,3-dimethyl-1H-pyrazol-5-amine (Compound 7)
(wherein the compound numbers are identified in Index Table A).

Embodiment 5

A composition of Embodiment 4 wherein component (a) comprises Compound 1.

Embodiment 6

A composition of Embodiment 4 wherein component (a) comprises Compound 2.

Embodiment 7

A composition of Embodiment 4 wherein component (a) comprises Compound 3.

Embodiment 8

A composition of Embodiment 4 wherein component (a) comprises Compound 4.

Embodiment 9

A composition of Embodiment 4 wherein component (a) comprises Compound 5.

Embodiment 10

A composition of Embodiment 4 wherein component (a) comprises Compound 6.

Embodiment 11

A composition of Embodiment 4 wherein component (a) comprises Compound 7.

Embodiment 12

A composition of Embodiment 4 wherein component (a) comprises Compound 8.

Embodiment 13

A composition of Embodiment 4 wherein component (a) comprises Compound 9.

Embodiment 14

A composition of Embodiment 4 wherein component (a) comprises Compound 10.

Embodiment 15

A composition of Embodiment 4 wherein component (a) comprises Compound 11.

Embodiment 16

A composition of Embodiment 4 wherein component (a) comprises Compound 12.

Embodiment 17

A composition comprising components (a) and (b) described in the Summary of the Invention or any one of Embodiments 1 through 16 wherein component (b) comprises at least one fungicidal compound selected from (b1).

Embodiment 17a

A composition comprising components (a) and (b) described in the Summary of the Invention or any one of Embodiments 1 through 17 wherein component (b) comprises at least one fungicidal compound selected from (b1a).

Embodiment 17b

A composition comprising components (a) and (b) described in the Summary of the Invention or any one of Embodiments 1 through 17a wherein component (b) comprises at least one fungicidal compound selected from (b1b).

Embodiment 18

A composition comprising components (a) and (b) described in the Summary of the Invention or any one of Embodiments 1 through 17b wherein component (b) comprises at least one fungicidal compound selected from (b2).

Embodiment 19

A composition comprising components (a) and (b) described in the Summary of the Invention or any one of Embodiments 1 through 18 wherein component (b) comprises at least one fungicidal compound selected from (b3).

Embodiment 20

A composition comprising components (a) and (b) described in the Summary of the Invention or any one of Embodiments 1 through 19 wherein component (b) comprises at least one fungicidal compound selected from (b4).

Embodiment 21

A composition comprising components (a) and (b) described in the Summary of the Invention or any one of Embodiments 1 through 20 wherein component (b) comprises at least one fungicidal compound selected from (b5).

Embodiment 22

A composition comprising components (a) and (b) described in the Summary of the Invention or any one of Embodiments 1 through 21 wherein component (b) comprises at least one fungicidal compound selected from (b6).

Embodiment 23

A composition comprising components (a) and (b) described in the Summary of the Invention or any one of Embodiments 1 through 22 wherein component (b) comprises at least one fungicidal compound selected from (b7).

Embodiment 24

A composition comprising components (a) and (b) described in the Summary of the Invention or any one of Embodiments 1 through 23 wherein component (b) comprises at least one fungicidal compound selected from (b8).

Embodiment 25

A composition comprising components (a) and (b) described in the Summary of the Invention or any one of Embodiments 1 through 24 wherein component (b) comprises at least one fungicidal compound selected from (b9).

Embodiment 26

A composition comprising components (a) and (b) described in the Summary of the Invention or any one of Embodiments 1 through 25 wherein component (b) comprises at least one fungicidal compound selected from (b10).

Embodiment 26a

A composition comprising components (a) and (b) described in the Summary of the Invention or any one of Embodiments 1 through 26 wherein component (b) comprises at least one fungicidal compound selected from (b10a).

Embodiment 26b

A composition comprising components (a) and (b) described in the Summary of the Invention or any one of Embodiments 1 through 26a wherein component (b) comprises at least one fungicidal compound selected from (b10b).

Embodiment 27

A composition comprising components (a) and (b) described in the Summary of the Invention or any one of Embodiments 1 through 26b wherein component (b) comprises at least one fungicidal compound selected from (b11).

Embodiment 28

A composition comprising components (a) and (b) described in the Summary of the Invention or any one of Embodiments 1 through 27 wherein component (b) comprises at least one fungicidal compound selected from (b12).

Embodiment 28a

A composition comprising components (a) and (b) described in the Summary of the Invention or any one of Embodiments 1 through 28 wherein component (b) comprises at least one fungicidal compound selected from (b13).

Embodiment 29

A composition comprising components (a) and (b) described in the Summary of the Invention or any one of Embodiments 1 through 28a further comprising (c) least one additional compound or agent that is biologically active.

Embodiment 30

A composition of Embodiment 29 wherein component (c) comprises at least one fungicidal compound selected from the group consisting of:
(c1) methyl benzimidazole carbamate (MBC) fungicides;
(c2) dicarboximide fungicides;
(c3) demethylation inhibitor (DMI) fungicides;
(c4) phenylamide fungicides;
(c5) amine/morpholine fungicides;
(c6) phospholipid biosynthesis inhibitor fungicides;
(c7) carboxamide fungicides;
(c8) hydroxy(2-amino-)pyrimidine fungicides;
(c9) anilinopyrimidine fungicides;
(c10) N-phenyl carbamate fungicides;
(c11) quinone outside inhibitor (QoI) fungicides;
(c12) phenylpyrrole fungicides;
(c13) quinoline fungicides;
(c14) lipid peroxidation inhibitor fungicides;
(c15) melanin biosynthesis inhibitors-reductase (MBI-R) fungicides;
(c16) melanin biosynthesis inhibitors-dehydratase (MBI-D) fungicides;
(c17) hydroxyanilide fungicides;
(c18) squalene-epoxidase inhibitor fungicides;
(c19) polyoxin fungicides;
(c20) phenylurea fungicides;
(c21) quinone inside inhibitor (QiI) fungicides;
(c22) benzamide fungicides;
(c23) enopyranuronic acid antibiotic fungicides;
(c24) hexopyranosyl antibiotic fungicides;
(c25) glucopyranosyl antibiotic: protein synthesis fungicides;
(c26) glucopyranosyl antibiotic: trehalase and inositol biosynthesis fungicides;
(c27) cyanoacetamideoxime fungicides;
(c28) carbamate fungicides;
(c29) oxidative phosphorylation uncoupling fungicides;
(c30) organo tin fungicides;
(c31) carboxylic acid fungicides;
(c32) heteroaromatic fungicides;
(c33) phosphonate fungicides;
(c34) phthalamic acid fungicides;
(c35) benzotriazine fungicides;
(c36) benzene-sulfonamide fungicides;
(c37) pyridazinone fungicides;
(c38) thiophene-carboxamide fungicides;
(c39) pyrimidinamide fungicides;
(c40) carboxylic acid amide (CAA) fungicides;
(c41) tetracycline antibiotic fungicides;
(c42) thiocarbamate fungicides;
(c43) benzamide fungicides;
(c44) host plant defense induction fungicides;
(c45) multi-site contact activity fungicides;
(c46) fungicides other than fungicides of component (a) and components (c1) through (c45); and
salts of compounds of (c1) through (c46).

Embodiment 31

A composition of Embodiment 29 or 30 wherein component (c) includes at least one compound selected from acibenzolar-S-methyl, aldimorph, ametoctradin, amisulbrom, anilazine, azaconazole, azoxystrobin, benalaxyl, benalaxyl-M, benodanil, benomyl, benthiavalicarb, benthiavalicarb-isopropyl, bethoxazin, binapacryl, biphenyl, bitertanol, bixafen, blasticidin-S, boscalid, bromuconazole, bupirimate, buthiobate, carboxin, carpropamid, captafol, captan, carbendazim, chloroneb, chlorothalonil, chlozolinate, clotrimazole, copper salts (such as Bordeaux mixture (tribasic copper sulfate), copper hydroxide and copper oxychloride), cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole, diniconazole-M, dinocap, dithianon, dodemorph, dodine, edifenphos, enestroburin, epoxiconazole, etaconazole, ethaboxam, ethirimol, etridiazole, famoxadone, fenamidone, fenarimol, fenbuconazole, fenfuram, fenhexamid, fenoxanil, fenpiclonil, fenpropidin, fenpropimorph, fenpyrazamine, fentin acetate, fentin chloride, fentin hydroxide, ferbam, ferimzone, fluazinam, fludioxonil, flumetover, flumorph, fluopicolide (also known as picobenzamid), fluopyram, fluoroimide, fluoxastrobin, fluquinconazole, flusilazole, flusulfamide, flutianil (2-[[2-fluoro-5-(trifluoromethyl)phenyl]thio]-2-[3-(2-methoxyphenyl)-2-thiazolidinylidene]acetonitrile), flutolanil, flutriafol, fluxapyroxad, folpet, fosetyl-aluminum, fuberidazole, furalaxyl, furametpyr, hexaconazole, hymexazol, guazatine, imazalil, imibenconazole, iminoctadine, iodocarb, ipconazole, iprobenfos, iprodione, iprovalicarb, isoprothiolane, isopyrazam, isotianil, kasugamycin, kresoxim-methyl, mancozeb, mandipropamid, maneb, mepronil, meptyldinocap, metalaxyl, metalaxyl-M, metconazole, methasulfocarb, metiram, metominostrobin, mepanipyrim, metrafenone, myclobutanil, naftifine, neo-asozin (ferric methanearsonate), nuarimol, octhilinone, ofurace, orysastrobin, oxadixyl, oxolinic acid, oxpoconazole, oxycarboxin, oxytetracycline, penconazole, pencycuron, penflufen, penthiopyrad, pefurazoate, phosphorous acid and salts thereof, phthalide, picoxystrobin, piperalin, polyoxin, probenazole, prochloraz, procymidone, propamocarb, propamocarb-hydrochloride, propiconazole, propineb, proquinazid, prothiocarb, prothioconazole, pyraclostrobin, pyrametostrobin, pyraoxystrobin, pyrazophos, pyribencarb, pyributicarb, pyrifenox, pyrimethanil, pyriofenone, pyroquilon, pyrrolnitrin, quinconazole, quinomethionate, quinoxyfen, quintozene, sedaxane, silthiofam, simeconazole, spiroxamine, streptomycin, sulfur, tebuconazole, tebufloquin, tecloftalam, tecnazene, terbinafine, tetraconazole, thiabendazole, thifluzamide, thiophanate, thiophanate-methyl, thiram, tiadinil, tolclofos-methyl, tolylfluanid, triadimefon, triadimenol, triarimol, triazoxide, tricyclazole, tridemorph, triflumizole, tricyclazole, trifloxystrobin, triforine, trimorphamide, triticonazole, uniconazole, validamycin, valifenalate (valiphenal), vinclozolin, zineb, ziram, zoxamide, N'-[4-[4-chloro-3-(trifluoromethyl)phenoxy]-2,5-dimethylphenyl]-N-ethyl-N-methylmethanimidamide, 5-chloro-6-(2,4,6-trifluorophenyl)-7-(4-methylpiperidin-1-yl)[1,2,4]triazolo[1,5-a]pyrimidine (BAS600), N-[2-[4-[[3-(4-chlorophenyl)-2-propyn-1-yl]oxy]-3-methoxyphenyl]ethyl]-3-methyl-2-[(methylsulfonyl)amino]butanamide, N-[2-[4-[[3-(4-chlorophenyl)-2-propyn-1-yl]oxy]-3-methoxyphenyl]ethyl]-3-methyl-2-[(ethylsulfonyl)amino]butanamide, 2-butoxy-6-iodo-3-propyl-4H-1-benzopyran-4-one, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]carbamate, N-[[(cyclopropylmethoxy)amino][6-(difluoromethoxy)-2,3-difluorophenyl]methylene]-benzeneacetamide, α-(methoxyimino)-N-methyl-2-[[[1-[3-(trifluoromethyl)-phenyl]ethoxy]imino]methyl]benzeneacetamide, N-[4-[4-chloro-3-(trifluoro-methyl)phenoxy]-2,5-dimethylphenyl]-N-ethyl-N-methylmethanimidamide, N-(4-chloro-2-nitrophenyl)-N-ethyl-4-methylbenzenesulfonamide, 2-[[[[3-(2,6-dichlorophenyl)-1-methyl-2-propen-1-ylidene]amino]oxy]methyl]-α-(methoxyimino)-N-methylbenzeneacetamide, 1-[(2-propenylthio)carbonyl]-2-(1-methylethyl)-4-(2-methylphenyl)-5-amino-1H-pyrazol-3-one, ethyl-6-octyl-[1,2,4]triazolo[1,5-a]pyrimidin-7-ylamine, pentyl N-[4-[[[[(1-methyl-1H-tetrazol-5-yl)phenylmethylene]amino]oxy]methyl]-2-thiazolyl]carbamate, pentyl N-[6-[[[[(1-methyl-1H-tetrazol-5-yl)phenylmethylene]amino]oxy]methyl]-2-pyridinyl]carbamate, 2-[(3-bromo-6-quinolinyl)oxy]-N-(1,1-dimethyl-2-butyn-1-yl)-2-(methylthio)acetamide, 2-[(3-ethynyl-6-quinolinyl)oxy]-N-[1-(hydroxymethyl)-1-methyl-2-propyn-1-yl]-2-(methylthio)acetamide, N-(1,1-dimethyl-2-butyn-1-yl)-2-[(3-ethynyl-6-quinolinyl)oxy]-2-(methylthio)acetamide and N'-[4-[[3-[(4-chlorophenyl)methyl]-1,2,4-thiadiazol-5-yl]oxy]-2,5-dimethylphenyl]-N-ethyl-N-methylmethanimidamide.

Embodiment 32

A composition of Embodiment 31 wherein component (c) includes at least one compound selected from azoxystrobin, bixafen, boscalid (nicobifen), bromuconazole, carbendazim, chlorothalonil, cyflufenamid, cyproconazole, difenoconazole, dimoxystrobin, epoxiconazole, etaconazole, famoxadone, fenbuconazole, fenpropidin, fenpropimorph, fluopyram, flusilazole, fluxapyroxad, hexaconazole, ipconazole, isopyrazam, kresoxim-methyl, metaconazole, metominostrobin/fenominostrobin, metrafenone, myclobutanil, penconazole, penthiopyrad, picoxystrobin, prochloraz, propiconazole, proquinazid, prothioconazole, pyraclostrobin, pyrametostrobin, pyraoxystrobin, pyriofenone, quinoxyfen, sedaxane, tebuconazole, trifloxystrobin and triticonazole.

Embodiment 33

A composition of Embodiment 32 wherein component (c) includes at least one compound selected from azoxystrobin, bixafen, boscalid, cyflufenamid, cyproconazole, difenconazole, epoxiconazole, fluopyram, isopyrazam, kresoxim-methyl, metaconazole, metrafenone, myclobutanil, penthiopyrad, picoxystrobin, pyraclostrobin, pyrametostrobin, pyraoxystrobin, pyriofenone, proquinazid, prothioconazole, quinoxyfen, sedaxane, tebuconazole and trifloxystrobin.

Embodiment 34

A composition comprising components (a) and (b) described in the Summary of the Invention or any one of Embodiments 1 through 33 wherein the composition further comprises in component (c) at least one invertebrate pest control compound or agent.

Of note as an embodiment is a composition comprising components (a) and (b) described in the Summary of the Invention or any one of Embodiments 1 through 34 wherein component (b1) is (b1a) (i.e. Formula B1a)

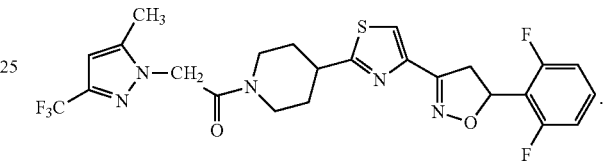

Also of note is any of the fungicidal compositions or the methods relating to the compositions described in the Summary of the Invention or any embodiments described herein, including Embodiments 1-34, wherein component (b) does not comprise (b13) the compound of Formula B13, or a salt thereof. Also of note is any of the fungicidal compositions or the methods relating to the compositions described in the Summary of the Invention or any embodiments described herein, including Embodiments 1-34, wherein component (b) furthermore does not comprise (b10a) the compound of Formula B10a, (b10b) the compound of Formula B10b, or a salt thereof.

Embodiments of this invention, including Embodiments 1-34 above as well as any other embodiments described herein, can be combined in any manner. In addition, embodiments of this invention, including Embodiments 1-34 above as well as any other embodiments described herein, and any combination thereof, pertain to the methods of the present invention. Furthermore, embodiments of the invention described herein and their combinations pertain to compounds of Formula 1 and intermediates for their preparation, such as compounds of Formulae 14, 17, 20 and 22.

Of note is the composition of any one of the embodiments described herein, including Embodiments 1 through 34, wherein reference to Formula 1 includes salts thereof but not N-oxides thereof; therefore the phrase "a compound of Formula 1" can be replaced by the phrase "a compound of Formula 1 or a salt thereof". In this composition of note, component (a) comprises a compound of Formula 1 or a salt thereof.

Also noteworthy as embodiments are fungicidal compositions of the present invention comprising a composition (e.g., in a fungicidally effective amount) of any one of Embodiments 1 through 34, and at least one additional component selected from the group consisting of surfactants, solid diluents and liquid diluents.

Embodiments of the invention further include methods for controlling plant diseases caused by fungal plant pathogens comprising applying to the plant or portion thereof, or to the plant seed or seedling, a fungicidally effective amount of a composition any one of Embodiments 1 through 34, (e.g., as a composition including formulation ingredients as described herein). Embodiments of the invention also include methods for protecting a plant or plant seed from diseases caused by fungal pathogens comprising applying a fungicidally effective amount of a composition of any one of Embodiments 1 through 34 to the plant or plant seed.

Some embodiments of the invention involve control of a plant disease or protection from a plant disease that primarily afflicts plant foliage and/or applying the composition of the invention to plant foliage (i.e. plants instead of seeds). The preferred methods of use include those involving the above preferred compositions; and the diseases controlled with particular effectiveness include plant diseases caused by fungal plant pathogens. Combinations of fungicides used in accordance with this invention can facilitate disease control and retard resistance development.

As described in the Summary of the Invention, an aspect of the present invention is directed at a composition comprising as component (a) at least one compound selected from Formula 1, N-oxides, and salts thereof. One or more of the following methods and variations as described in Schemes 1-16 can be used to prepare the compounds of Formula 1. The definitions of $R^1$, $R^2$, $R^3$, $R^{32}$ and M in the compounds of Formulae 1-23 below are as defined above in the Summary of the Invention unless otherwise noted. Formulae 6a and 6b are various subsets of Formula 6; Formula 10a is a subset of Formula 10; and Formula 17a is a tautomeric subset of Formula 17. Substituents for each subset formula are as defined for its parent formula unless otherwise noted.

As shown in Scheme 1, compounds of Formula 1 can be prepared by the reaction of 1H-pyrazole compounds of Formula 2 with various methylating agents (e.g., Formula 3), such as iodomethane, methyl sulfonates (e.g., methyl mesylate (OMs) or tosylate (OTs)) or trimethyl phosphate, preferably in the presence of an organic or inorganic base such as 1,8-diazabicyclo[5.4.0]undec-7-ene, potassium carbonate or potassium hydroxide, and in a solvent such as N,N-dimethylformamide (DMF), tetrahydrofuran (THF), toluene or water.

Scheme 1

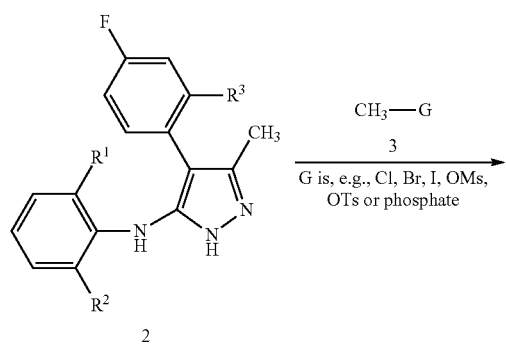

As is shown in Scheme 2, compounds of Formula 1 can be prepared by the reaction of compounds of Formula 4 with aromatic compounds of Formula 5 containing a leaving group G (e.g., halogen or (halo)alkylsulfonate), optionally in the presence of a metal catalyst, and generally in the presence of a base and a polar aprotic solvent such as N,N-dimethylformamide or dimethyl sulfoxide. For example, compounds of Formula 5 wherein the benzene ring contains electron-withdrawing substituents react by direct displacement of the leaving group G from the ring to provide compounds of Formula 1. Compounds of Formula 5 are commercially available or their preparation is known in the art.

Scheme 2

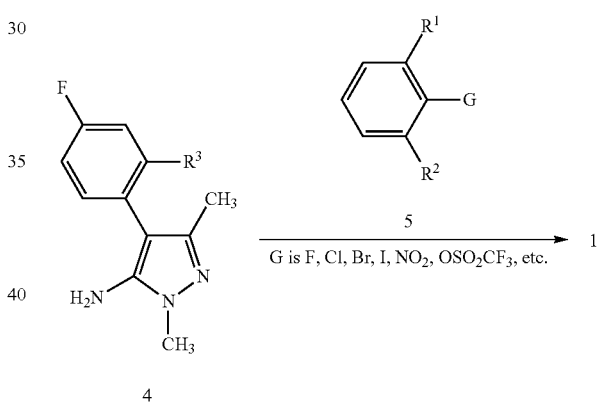

For reactions according to the method of Scheme 2 of a compound of Formula 4 with a compound of Formula 5 wherein the aromatic ring lacks sufficiently electron-withdrawing substituents, or to improve reaction rate, yield or product purity, the use of a metal catalyst (e.g., metal or metal salt) in amounts ranging from catalytic up to superstoichiometric can facilitate the desired reaction. Typically for these conditions, G is Br or I or a sulfonate such as $OS(O)_2CF_3$ or $OS(O)_2(CF_2)_3CF_3$. For example, copper salt complexes (e.g., CuI with N,N-dimethylethylenediamine, proline or bipyridyl), palladium complexes (e.g., tris-(dibenzylideneacetone)dipalladium(0)) or palladium salts (e.g., palladium acetate) with ligands such as 4,5-bis(diphenylphosphino)-9,9-dimethylxanthene (i.e. "Xantphos"), 2-dicyclohexylphosphino-2',4',6'-triisopropylbiphenyl (i.e. "Xphos") or 2,2'-bis(diphenylphosphino)-1, 1'-binaphthalene (i.e. "BINAP"), in the presence of a base such as potassium carbonate, cesium carbonate, sodium phenoxide or sodium tert-butoxide, in a solvent such as N,N-dimethylformamide, 1,2-dimethoxyethane, dimethyl sulfoxide, 1,4-dioxane or toluene, optionally mixed with alcohols such as ethanol, can be used. Alternatively as illustrated in Scheme 3, compounds of Formula 1 can be prepared by reaction of compounds of Formula 6 (i.e. 5-bromopyrazoles or other pyrazoles substituted at the 5-position with a leaving group) with compounds of Formula 7 under metal-catalyzed conditions similar to those described above for Scheme 2. Compounds of Formula 7 are commercially available or their preparation is known in the art.

Scheme 3

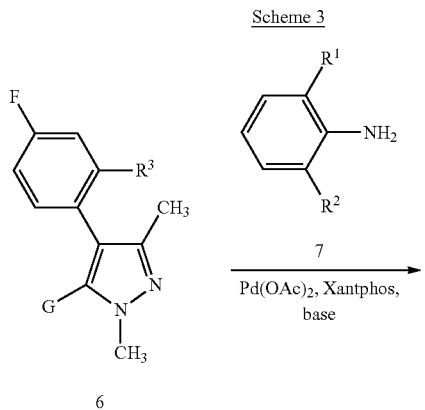

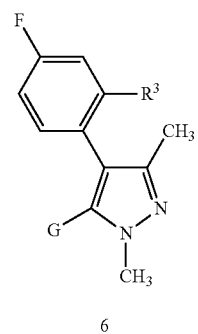

As shown in Scheme 5, 5-bromopyrazoles of Formula 6a (i.e. Formula 6 wherein G is Br) can be prepared by reacting 5-hydroxypyrazoles of Formula 8 with phosphorus tribromide as described in *Tetrahedron Lett.* 2000, 41(24), 4713.

Scheme 5

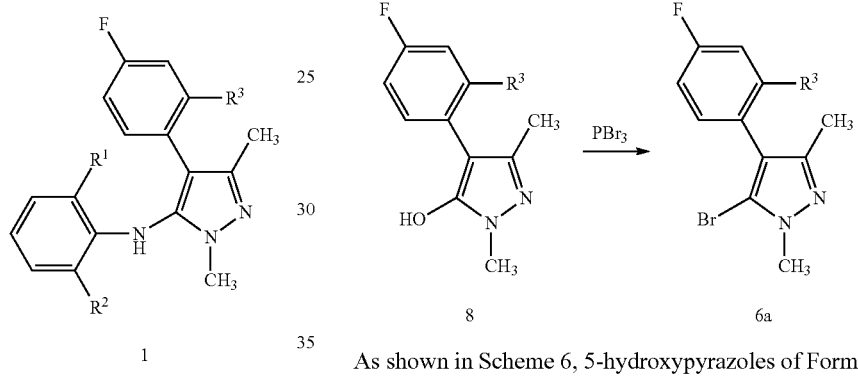

As shown in Scheme 4, compounds of Formula 6 wherein G is Br or I can be prepared by reaction of 5-aminopyrazoles of Formula 4 under diazotization conditions either in the presence of, or followed by combination with, copper salts containing bromide or iodide. For example, addition of tert-butyl nitrite to a solution of a 5-aminopyrazole of Formula 4 in the presence of $CuBr_2$ in a solvent such as acetonitrile provides the corresponding 5-bromopyrazole of Formula 6. Likewise, a 5-aminopyrazole of Formula 4 can be converted to a diazonium salt and then to a corresponding 5-halopyrazole of Formula 6 by treatment with sodium nitrite in solvents such as water, acetic acid or trifluoroacetic acid, in the presence of a mineral acid typically containing the same halide atom (such as aqueous HI solution for G being I), followed by treatment with the corresponding copper(I) or copper(II) salt according to general procedures well known to those skilled in the art.

As shown in Scheme 6, 5-hydroxypyrazoles of Formula 8 can also be used to prepare 5-fluoroalkylsulfonyl (e.g., 5-trifluoromethanesulfonyl, 5-nonafluorobutylsulfonyl) pyrazoles of Formula 6b (i.e. Formula 6 wherein G is fluoroalkylsulfonyloxy) as described in *Synlett* 2004, 5, 795.

Scheme 6

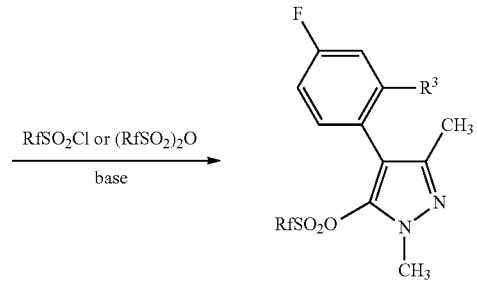

wherein Rf is fluoroalkyl such as $CF_3$ or $(CF_2)_2CF_3$

As shown in Scheme 7, compounds of Formula 1 can be prepared by reaction of 4-bromo or iodo pyrazoles of Formula 9 with organometallic compounds of Formula 10 under transition-metal-catalyzed cross-coupling reaction conditions. Reaction of a 4-bromo or iodo pyrazole of Formula 9 with a boronic acid, trialkyltin, zinc or organomagnesium reagent of Formula 10 in the presence of a palladium or nickel catalyst having appropriate ligands (e.g., triphenylphosphine ($PPh_3$), dibenzylideneacetone (dba), dicyclohexyl(2',6'-dimethoxy[1,1'-biphenyl]-2-yl)phosphine (SPhos)) and a base, if needed, affords the correspond- Scheme 4

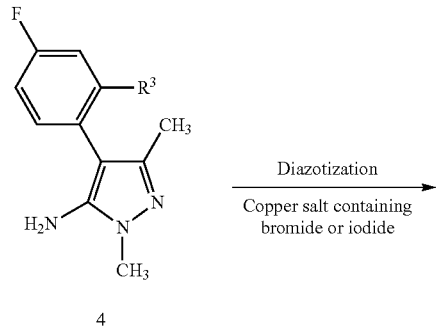

ing compound of Formula 1. For example, a substituted aryl boronic acid or derivative e.g., Formula 10 wherein M is $B(OH)_2$, $B(OC(CH_3)_2C(CH_3)_2O))$ or $B(O\text{-}i\text{-}Pr)_3^{\ominus}Li^{\oplus}$, reacts with a 4-bromo- or 4-iodopyrazole of Formula 9 in the presence of dichlorobis(triphenylphosphine) palladium(II) and aqueous base such as sodium carbonate or potassium hydroxide, in solvents such as 1,4-dioxane, 1,2-dimethoxyethane, toluene or ethyl alcohol, or under anhydrous conditions with a ligand such as phosphine oxide or phosphite ligand (e.g., diphenylphosphine oxide) and potassium fluoride in a solvent such as 1,4-dioxane (see *Angewandte Chemie, International Edition* 2008, 47(25), 4695-4698) to provide the corresponding compound of Formula 1.

Scheme 7

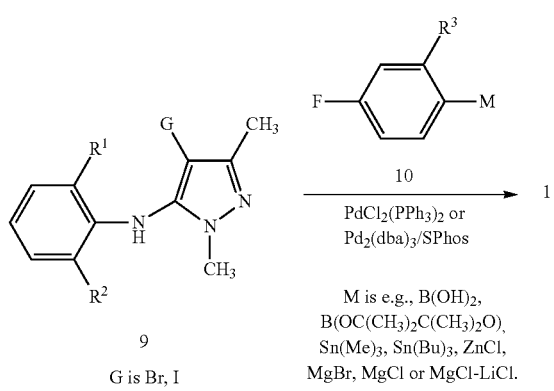

As illustrated in Scheme 8, compounds of Formula 4 can be prepared by reacting compounds of Formula 11 with compounds of Formula 10a (e.g., compounds of Formula 10 wherein M is $B(OH)_2$) using transition-metal-catalyzed cross-coupling reaction conditions as described for the method of Scheme 7.

Scheme 8

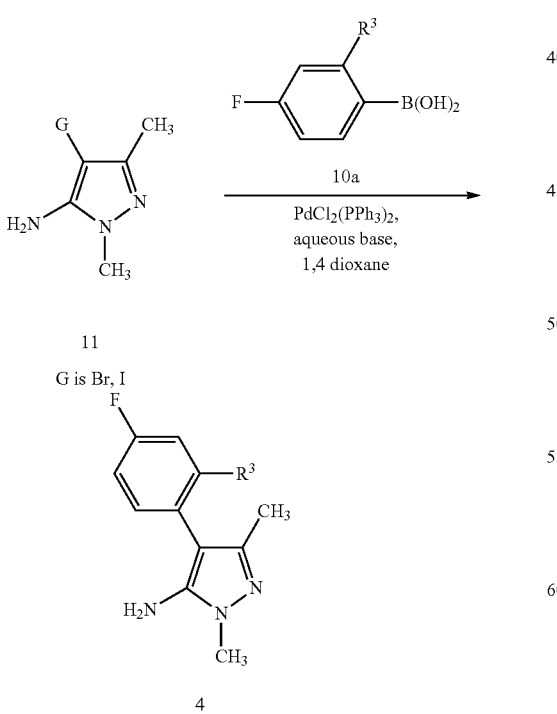

As illustrated in Scheme 9, pyrazoles of Formula 9 wherein G is Br or I are readily prepared by the reaction of pyrazoles unsubstituted at the 4-position (Formula 12) with halogenating reagents such as bromine, sodium bromite, N-bromosuccinimide (NBS) or N-iodosuccinimide (NIS), in solvents such as acetic acid, acetonitrile, N,N-dimethylformamide, N,N-dimethylacetamide or 1,4-dioxane, or a mixture of water with the aforementioned solvents, at temperatures ranging from ambient to the boiling point of the solvent.

Scheme 9

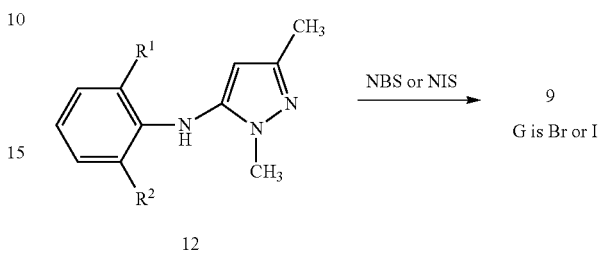

As illustrated in Scheme 10, using reaction conditions similar to those for the method of Scheme 9, the pyrazole of Formula 13 can be converted into intermediates of Formula 11 which are useful for preparing compounds of Formula 4 as depicted in Scheme 8. The compound of Formula 13 not only can be prepared by methods known in the art, but is also commercially available.

Scheme 10

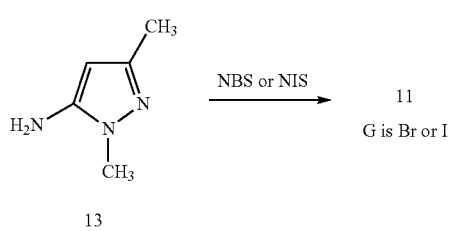

As shown in Scheme 11, compounds of Formula 12 can be prepared from corresponding compounds of Formula 13 by procedures analogous to those used for the method of Scheme 2. Compounds of Formula 13 are commercially available or can be prepared by methods known in the art.

Scheme 11

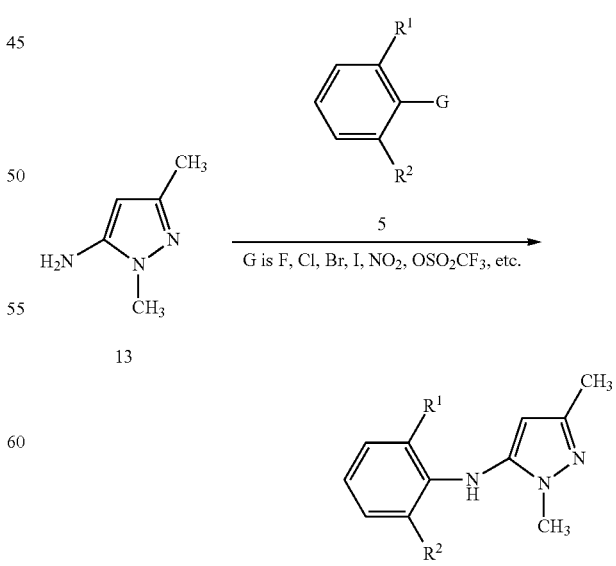

General methods useful for preparing 5-aminopyrazoles of Formula 4 are well known in the art; see, for example, *Journal für Praktische Chemie (Leipzig)* 1911, 83, 171 and *J. Am. Chem. Soc.* 1954, 76, 501. Such a method is illustrated in Scheme 12.

Scheme 12

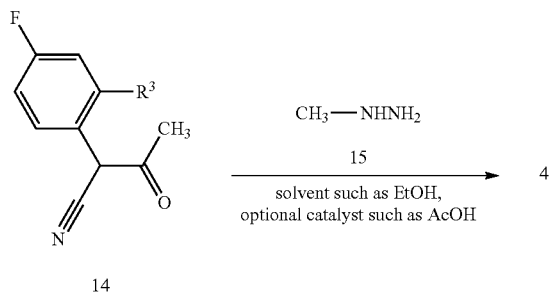

Similarly, general methods useful for preparing 5-hydroxypyrazoles of Formula 8 are well known in the art; see, for example, *Annalen der Chemie* 1924, 436, 88. Such a method is illustrated in Scheme 13.

Scheme 13

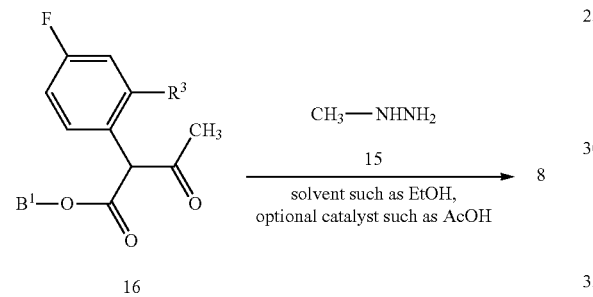

$B^1$ is alkyl, aryl, benzyl, etc.

As shown in Scheme 14, compounds of Formula 1 can be prepared by condensing compounds of Formula 17 with methylhydrazine (Formula 15) in a solvent such as ethanol or methanol and optionally in the presence of an acid or base catalyst such as acetic acid, piperidine or sodium methoxide, according to general procedures known in the art. The method of Scheme 14 is illustrated by Step C of Synthesis Example 1 and Step B of Synthesis Example 2.

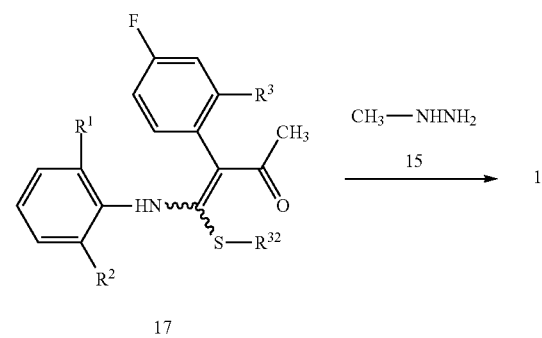

wherein $R^{32}$ is H or lower alkyl
(e.g., $CH_3$, $CH_2CH_3$ or $(CH_2)_2CH_3$)

In a manner analogous to the method of Scheme 14, compounds of Formula 2 can be similarly prepared by condensing compounds of Formula 17 with hydrazine. This method is described in *Chemistry of Heterocyclic Compounds* 2005, 41(1), 105-110.

As shown in Scheme 15, compounds of Formula 17 (wherein, $R^{32}$ is H or lower alkyl such as $CH_3$, $CH_2CH_3$ or $(CH_2)_2CH_3$) can be prepared by reaction of corresponding ketene dithioacetal compounds of Formula 18 with compounds of Formula 19 optionally in the presence of a base, such as sodium hydride or ethylmagnesium chloride, in solvents such as toluene, tetrahydrofuran or dimethoxymethane, at temperatures ranging from −10° C. to the boiling point of the solvent. See, for example, *J. Heterocycl. Chem.* 1975, 12(1), 139. Methods useful for preparing compounds of Formula 18 are known in the art.

Scheme 15

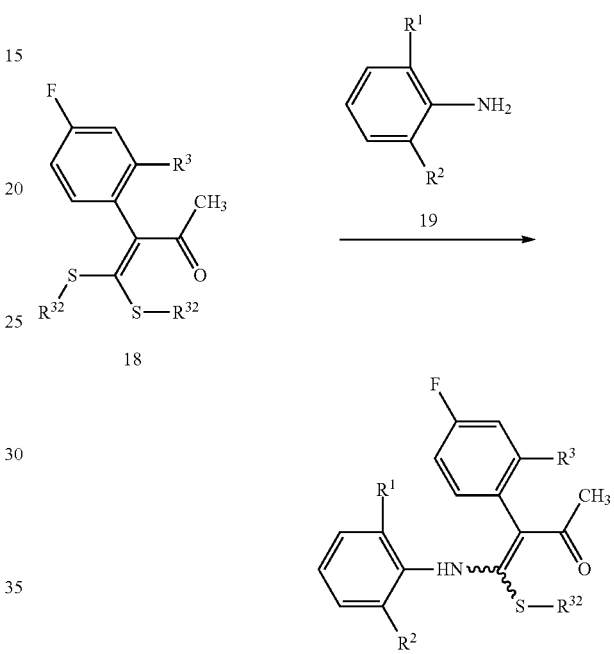

wherein $R^{32}$ is H or lower alkyl (e.g., $CH_3$, $CH_2CH_3$ or $(CH_2)_2CH_3$)

As shown in Scheme 16, compounds of Formula 17 wherein $R^{32}$ is lower alkyl (e.g., methyl, ethyl, n-propyl) and Formula 17a (i.e. tautomer of Formula 17 wherein $R^{32}$ is H) can be prepared starting by condensation reaction of corresponding isothiocyanate compounds of Formula 20 with arylacetone compounds of Formula 21 to give intermediate compounds of Formula 22, which are salts of the thioamides of Formula 17a. The intermediate compounds of Formula 22 can either be used in situ as is illustrated by Step C of Synthesis Example 1 or isolated before further conversion as is illustrated by Steps A and B of Synthesis Example 2. Bases useful for preparing compounds of Formula 22 include hydrides, alkoxides, hydroxides or carbonates of sodium or potassium, such as sodium hydride, potassium tert-butoxide, sodium ethoxide, potassium hydroxide, sodium hydroxide or potassium carbonate. Amine bases (e.g., triethylamine or N,N-diisopropylethylamine) can also be used to effect the condensation of the compounds of Formulae 20 and 21. A variety of solvents are useful, such as tetrahydrofuran, ether, toluene, N,N-dimethylformamide, alcohols (e.g., ethanol), esters (e.g., ethyl acetate or isopropyl acetate), or mixtures thereof. Solvents are chosen for compatibility with the base selected, as is well-known in the art. Reaction temperatures can range from −78° C. to the boiling point of the solvent. One useful mixture of base and solvent is potassium tert-butoxide in tetrahydrofuran, to which at −70 to 0° C. is added a solution of an isothiocyanate of Formula 20 and a carbonyl compound of Formula 21, which are either combined into one solution, or added separately, preferably by addition of the carbonyl compound followed by addition of the isothiocyanate. The salt compound of Formula 22 can be acidified to form the ketothioamide compound of Formula 17a or alkylated with $R^{32}X^1$ (Formula 23) wherein $R^{32}$ is lower alkyl (e.g., methyl, ethyl, n-propyl) and $X^1$ is a nucleofuge (i.e. a nucleophilic reaction leaving group such as Br, I, $OS(O)_2CH_3$) to form the corresponding compound of Formula 17. This general method is known in the chemical literature; see, for example, *Zhurnal Organicheskoi Khimii* 1982, 18(12), 2501. The method of Scheme 16 to prepare a non-isolated intermediate compound of Formula 17 wherein $R^{32}$ is methyl is illustrated by Step C of Synthesis Example 1. The method of Scheme 16 to prepare an isolated intermediate compound of Formula 22 is illustrated by Step A of Synthesis Example 2.

The above reactions can also in many cases be performed in alternate sequence, such as the preparation of 1H pyrazoles for use in the reaction in Scheme 2 by reactions illustrated later for the general preparation of substituted pyrazoles.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1.

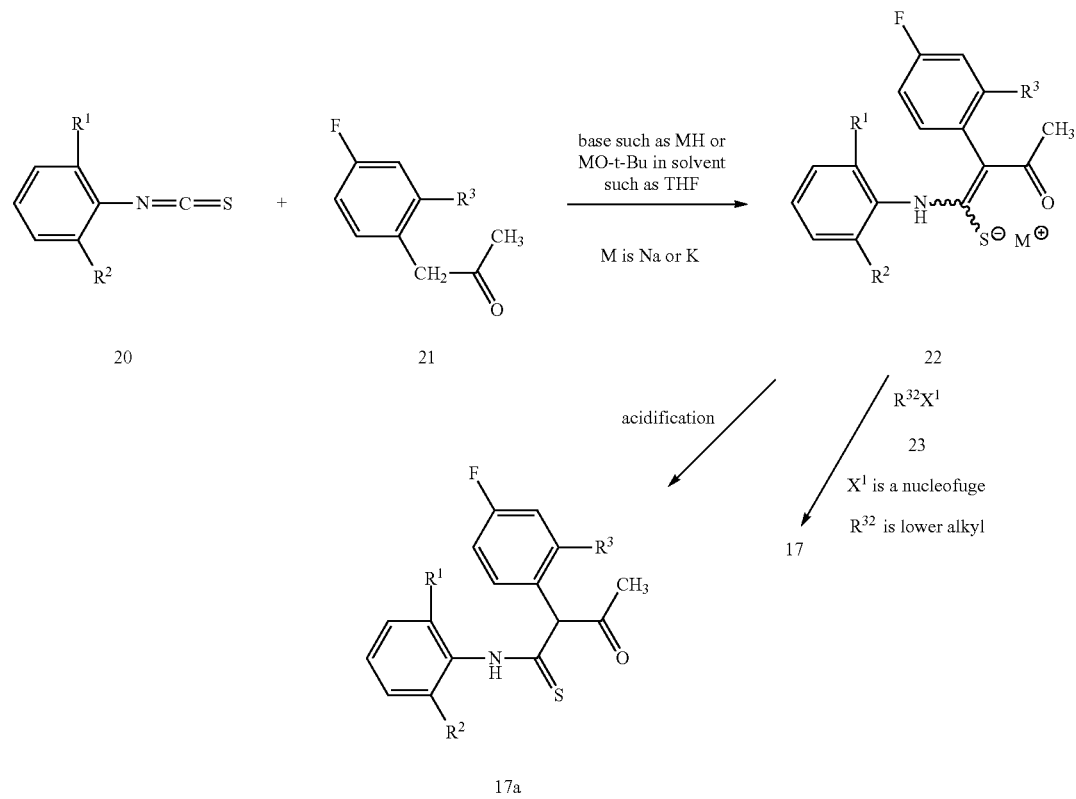

Ketothioamides of Formula 17a can also be prepared by allowing the corresponding ketoamides to react with sulfurizing agents such as Lawesson's reagent or $P_2S_5$; see, for example, *Helv. Chim. Acta.* 1998, 81(7), 1207.

It is recognized by one skilled in the art that various functional groups can be converted into others to provide different compounds of Formula 1. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1.

One skilled in the art will also recognize that it may be necessary to perform a combination of the steps illustrated in the above schemes in an order other than that implied by the particular sequence presented to prepare the compounds of Formula 1. One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding synthesis description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in CDCl$_3$ unless otherwise noted; "s" means singlet, "br s" means broad singlet, "d" means doublet, "dd" means doublet of doublets, "t" means triplet, "dt" means doublet of triplets, "m" means multiplet.

Synthesis Example 1

Preparation of 4-(2-Bromo-4-fluorophenyl)-N-(2-chloro-6-fluorophenyl)-1,3-dimethyl-1H-pyrazol-5-amine (Compound 4)

Step A: Preparation of 1-(2-Bromo-4-fluorophenyl)-2-propanone

A solution of sodium methoxide in methanol (25%, 34 mL, 157 mmol) was combined with toluene (200 mL). The methanol was then distilled off at 90° C. using a Dean-Stark trap. After the solution was cooled to 70° C., 2-bromo-4-fluorobenzeneacetonitrile (21.4 g, 100 mmol) dissolved in ethyl acetate (40 mL) was added from a dropping funnel over 20 min with mechanical stirring. At this point additional toluene (150 mL) was added to facilitate stirring of a voluminous light pink precipitate. The reaction mixture was poured into water, and the organic phase was separated. The aqueous phase was acidified and extracted with ethyl acetate. The ethyl acetate phase was dried and concentrated under reduced pressure to provide the intermediate compound α-acetyl-2-bromo-4-fluorobenzeneacetonitrile as a crude oil.

The crude oil was stirred in sulfuric acid (60%, 170 mL), and the resulting mixture was refluxed for 6.5 h. The reaction mixture was then extracted with hexanes (2×100 mL), and the combined hexane extracts were washed with water and brine, dried (MgSO$_4$) and concentrated under reduced pressure to yield the title compound as a yellow oil (14.7 g), which was used without further purification in Step C.

$^1$H NMR δ 7.33 (m, 1H), 7.18 (m, 1H), 7.01 (m, 1H), 3.85 (s, 2H), 2.23 (s, 3H).

Step B: Preparation of 1-Chloro-3-fluoro-2-isothiocyanatobenzene

To a solution of 2-chloro-6-fluorobenzenamine (5.0 g, 34 mmol) in chlorobenzene (52 mL) was added carbonothioic dichloride (thiophosgene) (5.1 g, 45 mmol) and DMF (0.27 mL). The reaction mixture was refluxed for 2 h and then concentrated to leave the title compound as a brown oil (6.15 g), which was used in Step C without further purification.

$^1$H NMR δ 7.18 (m, 2H), 7.07 (m, 1H).

Step C: Preparation of 4-(2-Bromo-4-fluorophenyl)-N-(2-chloro-6-fluorophenyl)-1,3-dimethyl-1H-pyrazol-5-amine To a solution of potassium tert-butoxide (0.41 g, 3.3 mmol) in THF (20 mL) at 0° C. was added a solution of 1-(2-bromo-4-fluorophenyl)-2-propanone (i.e. the product of Step A) (0.70 g, 3.0 mmol) in THF (10 mL) over 5 minutes. Stirring was continued for 1 h and then the temperature was reduced to −10° C. A solution of 1-chloro-3-fluoro-2-isothiocyanatobenzene (i.e. the product of Step B) (0.57 g, 3.0 mmol) in THF (10 mL) was added over 6 minutes, and stirring was continued for 15 minutes to provide a reaction mixture containing the intermediate compound 3-(2-bromo-4-fluorophenyl)-4-[(2-chloro-6-fluorophenyl)amino]-4-mercapto-3-buten-2-one potassium salt (1:1), which is the potassium salt of α-acetyl-2-bromo-N-(2-chloro-6-fluorophenyl)-4-fluorobenzeneethanethioamide. Iodomethane (0.54 g, 3.8 mmol) was added, and the cooling bath was removed to provide a reaction mixture containing the intermediate compound 3-(2-bromo-4-fluorophenyl)-4-[(2-chloro-6-fluorophenyl)amino]-4-(methylthio)-3-buten-2-one. After 5 min, water (0.2 mL, 11 mmol), glacial acetic acid (0.53 mL, 9.1 mmol) and methylhydrazine (0.81 mL, 15 mmol) were added in rapid succession, and the reaction mixture was heated to reflux for 6 h. The crude reaction mixture was then concentrated under reduced pressure and purified by MPLC (0 to 100% ethyl acetate in hexanes as eluent) to provide the title product as an off-white solid (0.55 g).

$^1$H NMR δ 7.24 (m, 1H), 7.04 (m, 1H), 6.95 (m, 1H), 6.87 (m, 1H), 6.78 (m, 1H), 6.68 (m, 1H), 5.45 (d, 1H), 3.80 (s, 3H), 2.10 (s, 3H).

Example 2

Preparation of 4-(2-Bromo-4-fluorophenyl)-N-(2,6-difluorophenyl)-1,3-dimethyl-1H-pyrazol-5-amine (Compound 11)

Step A: Preparation of 3-(2-Bromo-4-fluorophenyl)-4-[(2,6-difluorophenyl)amino]-4-mercapto-3-buten-2-one potassium salt (1:1)

To a solution of 1-(2-bromo-4-fluorophenyl)-2-propanone (23.4 g, 101 mmol) in methyl tert-butyl ether (300 mL) cooled to 6° C. with aid of an ice bath was added a tetrahydrofuran solution of potassium tert-butoxide (1.0 M, 100 mL, 100 mmol) over 30 min. During the addition of about 90 mL of potassium tert-butoxide solution the temperature of the reaction mixture was maintained at 6-8° C., and then the ice bath was removed during the addition of the remaining potassium tert-butoxide solution.

At the completion of the potassium tert-butoxide solution addition, the reaction mixture was a light yellow solution at 12° C. The reaction mixture was stirred for 30 min at 12-16° C. The reaction mixture was then cooled to 3° C., and a solution of 1,3-difluoro-2-isothiocyanatobenzene (17.4 g, 102 mmol) in methyl tert-butyl ether (50 mL) was added over 20 min while maintaining the temperature of the reaction mixture between 3 and 5° C. The resulting yellow slurry was then slowly warmed to 12° C. over 90 min. The mixture was diluted with hexanes (100 mL) and cooled to 8° C., and then the solid product was isolated by filtration. The product was dried in a vacuum oven at 70° C. overnight to provide the title product as a yellow solid (32.3 g).

$^1$H NMR (DMSO-d$_6$) δ 14.36 (s, 1H), 7.38 (dd, 1H), 7.22 (dd, 1H), 7.17 (m, 1H), 7.06 (dd, 1H), 6.99 (t, 2H), 1.50 (s, 3H).

Step B: Preparation of 4-(2-Bromo-4-fluorophenyl)-N-(2,6-difluorophenyl)-1,3-dimethyl-1H-pyrazol-5-amine A stirred mixture of 3-(2-bromo-4-fluorophenyl)-4-[(2,6-difluorophenyl)amino]-4-mercapto-3-buten-2-one potassium salt (1:1) (i.e. the product of Step A) (32.3 g, 73.4 mmol), acetic acid (44 g, 73 mmol) and methylhydrazine (109 mmol) in ethanol (200 mL) was heated at 65° C. for 3 h. Then the temperature was increased to 70° C. over 15 min. To the light yellow cloudy reaction mixture was added water (200 mL) over 30 min. The resulting yellow slurry was cooled to 8° C. over 2 h and then held at 8° C. for 30 min more. The solids were collected by filtration, rinsed with aqueous ethanol (1:4 EtOH—H$_2$O by volume) and dried in a vacuum oven at 70° C. to provide the title product as yellow solid (25 g).

$^1$H NMR δ 7.23 (dd, 1H), 7.06 (dd, 1H), 6.89 (dt, 1H), 6.68 (m, 3H), 5.15 (br s, 1H), 3.81 (s, 3H), 2.11 (s, 3H).

By the procedures described herein together with methods known in the art, the compounds disclosed in Table 1 that follows can be prepared.

TABLE 1

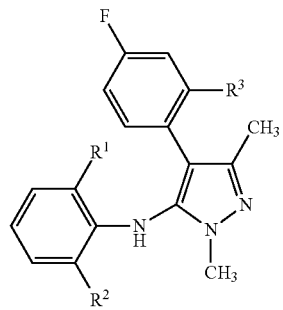

| R$^1$ | R$^2$ | R$^3$ |
|---|---|---|
| F | H | Cl |
| Cl | H | Cl |
| Br | H | Cl |
| F | H | Br |
| Cl | H | Br |
| Br | H | Br |
| F | F | Cl |
| Cl | F | Cl |
| Br | F | Cl |
| F | F | Br |
| Cl | F | Br |
| Br | F | Br |

Tables 2-5 disclose specific compounds useful as process intermediates for preparing compounds of Formula 1, N-oxides, and salts thereof. The "Note" column in these tables references physical property data (e.g., $^1$H NMR spectra, MS parent ion(s), melting ranges) for representative compounds. Mass spectra (MS) are reported as the molecular weight of the highest isotopic abundance parent ion (M+1) formed by addition of H$^+$ (molecular weight of 1) to the molecule, observed by mass spectrometry using atmospheric pressure chemical ionization (AP$^+$). The presence of molecular ions containing one or more higher atomic weight isotopes of lower abundance (e.g., $^{37}$Cl, $^{81}$Br) is not reported. In some instances, the M−1 ion is also reported.

As described for Scheme 12, compounds of Formula 14 are useful process intermediates for preparing compounds of Formula 4 as intermediates to compounds of Formula 1, which are useful as component (a) in the present composition. Illustrative of compounds of Formula 14 are those specifically disclosed in Table 2.

TABLE 2

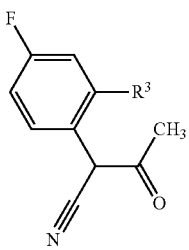

14

| R$^3$ | Note |
|---|---|
| Cl | 2-1 |
| Br | 2-2 |

Note 2-1: $^1$H NMR (CDCl$_3$) δ 7.49 (m, 1H), 7.25 (m, 1H), 7.11 (m, 1H), 5.14 (s, 1H), 2.36 (s, 3H).

Note 2-2: $^1$H NMR (CDCl$_3$) δ 7.49 (m, 2H), 7.41 (m, 1H), 7.17 (m, 1H), 5.20 (s, 1H), 2.35 (s, 3H).

As described for Scheme 14, compounds of Formula 17 including Formula 17a (Formula 17 tautomer wherein R$^{32}$ is H) are useful process intermediates for preparing compounds of Formula 1, which are useful as component (a) in the present composition. Illustrative of compounds of Formulae 17 and 17a are those specifically disclosed in Table 3a and 3b.

TABLE 3a

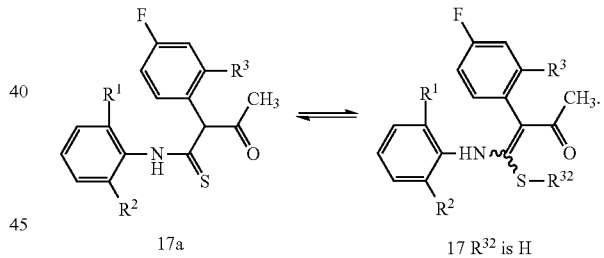

17a      17 R$^{32}$ is H

| R$^1$ | R$^2$ | R$^3$ | Note |
|---|---|---|---|
| F | H | Cl | |
| Cl | H | Cl | |
| Br | H | Cl | |
| F | H | Br | |
| Cl | H | Br | 3a-1 |
| Br | H | Br | |
| F | F | Cl | |
| Cl | F | Cl | |
| Br | F | Cl | 3a-2 |
| F | F | Br | 3a-3 |
| Cl | F | Br | |
| Br | F | Br | |

Note 3a-1: $^1$H NMR (CDCl$_3$) δ 15.36 (s, 1H), 8.09 (d, 1H), 7.62 (br s, 1H), 7.52 (dd, 1H), 7.42 (q, 1H), 7.37 (d, 1H), 7.29 (t, 1H), 7.19 (m, 2H), 1.82 (s, 3H).
Note 3a-2: MS 420 (M + 1). Melting 134-135° C.
Note 3a-3: $^1$H NMR (CDCl$_3$) δ 15.29 (s, 1H), 7.53 (dd, 1H), 7.43 (dd, 1H), 7.29 (m, 1H), 7.19 (dt, 1H), 6.95 (t, 2H), 6.82 (s, 1H), 1.81 (s, 3H).

TABLE 3b

17

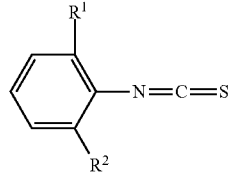

| R¹ | R² | R³ | Note |
|---|---|---|---|
| $R^{32}$ is $CH_3$. | | | |
| F | H | Cl | |
| Cl | H | Cl | 3b-1 |
| Br | H | Cl | 3b-2 |
| F | F | Cl | 3b-3 |
| Cl | F | Cl | |
| Br | F | Cl | 3b-4 |
| F | F | Br | 3b-5 |
| Cl | F | Br | 3b-6 |
| Br | F | Br | 3b-7 |
| $R^{32}$ $CH_2CH_3$. | | | |
| F | H | Cl | |
| Cl | H | Cl | |
| Br | H | Cl | |
| F | H | Br | |
| Cl | H | Br | |
| Br | H | Br | |
| F | F | Cl | |
| Cl | F | Cl | |
| Br | F | Cl | |
| F | F | Br | |
| Cl | F | Br | |
| Br | F | Br | |
| $R^{32}$ is $(CH_2)_2CH_3$. | | | |
| F | H | Cl | |
| Cl | H | Cl | |
| Br | H | Cl | |
| F | H | Br | |
| Cl | H | Br | |
| Br | H | Br | |
| F | F | Cl | |
| Cl | F | Cl | |
| Br | F | Cl | |
| F | F | Br | |
| Cl | F | Br | |
| Br | F | Br | |

Note 3b-1: ¹H NMR (CDCl₃) δ 12.76 (s, 1H), 766 (d, 1H), 7.43 (m, 2H), 7.32 (q, 1H), 7.24 (t, 1H), 7.10 (m, 2H), 1.89 (s, 3H), 1.84 (s, 3H).
Note 3b-2: MS 459.8 (M + 1), 457.9 (M − 1).
Note 3b-3: MS 372.0 (M + 1).
Note 3b-4: MS 433.8 (M + 1).
Note 3b-5: ¹H NMR (CDCl₃) δ 12.53 (s, 1H), 7.42 (dd, 1H), 7.32 (dd, 1H), 7.22 (m, 1H), 7.08 (dt, 1H), 6.97 (t, 2H), 1.92 (s, 3H), 1.89 (s, 3H).
Note 3b-6: MS 433.8 (M + 1), 431.8 (M − 1).
Note 3b-7: MS 477.8 (M + 1), 475.8 (M − 1).

As described for Scheme 16, compounds of Formula 20 are useful process intermediates for preparing compounds of Formulae 17 and 17a as intermediates to compounds of Formula 1, which are useful as component (a) in the present composition. Illustrative of compounds of Formula 20 are those specifically disclosed in Table 4.

TABLE 4

20

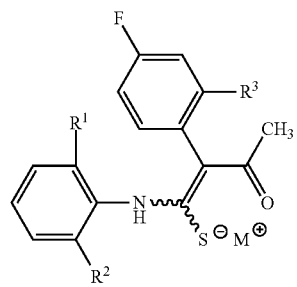

| R¹ | R² | Note |
|---|---|---|
| F | H | |
| Cl | H | |
| Br | H | |
| F | F | |
| Cl | F | 4-1 |
| Br | F | 4-2 |

Note 4-1: See Synthesis Example 1, Step B for ¹H NMR spectrum.
Note 4-2: ¹H NMR (CDCl₃) δ 7.36 (m, 1H), 7.10 (m, 1H). ¹⁹F NMR (CDCl₃) δ−114.93 (m, 1F).

As described for Scheme 16, compounds of Formula 22 are useful process intermediates for preparing compounds of Formulae 17 and 17a as intermediates to compounds of Formula 1, which are useful as component (a) in the present composition. Illustrative of compounds of Formula 22 are those specifically disclosed in Table 5.

TABLE 5

22

| R¹ | R² | R³ | Note |
|---|---|---|---|
| M is Na. | | | |
| F | H | Cl | |
| Cl | H | Cl | |
| Br | H | Cl | |
| F | H | Br | 5-1 |
| Cl | H | Br | |
| Br | H | Br | |
| F | F | Cl | |
| Cl | F | Cl | |
| Br | F | Cl | |
| F | F | Br | |
| Cl | F | Br | |
| Br | F | Br | |
| M is K. | | | |
| F | H | Cl | |
| Cl | H | Cl | |
| Br | H | Cl | |
| F | H | Br | |
| Cl | H | Br | 5-2 |
| Br | H | Br | |
| F | F | Cl | |
| Cl | F | Cl | |
| Br | F | Cl | |
| F | F | Br | 5-3 |

TABLE 5-continued

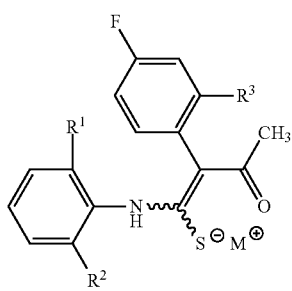

| R¹ | R² | R³ | Note |
|---|---|---|---|
| Cl | F | Br | |
| Br | F | Br | |

Note 5-1: Melting 115-118° C.
Note 5-2: $^1$H NMR (DMSO-$d_6$) δ 15.09 (s, 1H), 8.98 (d, 1H), 7.39 (d, 1H), 7.35 (d, 1H), 7.21 (dd, 1H), 7.10 (m, 2H), 6.90 (t, 1H), 1.49 (s, 3H).
Note 5-3: See Synthesis Example 2, Step B for $^1$H NMR spectrum.

Remarkably, 2,6-substituted aniline-pyrazole compounds of Formula 1 have now been discovered to have significantly improved pharmacokinetic properties compared to corresponding compounds wherein the phenyl ring connected to R¹ and R² has a nonhydrogen substituent at the para position relative to the bond connecting the phenyl ring to the remainder of the molecule. In particular in vertebrate animals, compounds of Formula 1 compared to para-substituted analogs have been found to have a significantly diminished distribution into fat, thereby reducing the possibility of bioaccumulation. Furthermore, in addition to having more favorable pharmacokinetic properties in vertebrate animals, 2,6-substituted anilino-pyrazole compounds of Formula 1 wherein R² is F, have been discovered to retain remarkably high activity when the phenyl para position is unsubstituted against plant fungal diseases, such as caused by *Septoria tritici*. Because of their extraordinarily desirable biological profile, compounds of Formula 1 are remarkably useful as component (a) in combination with fungicidal compounds of component (b) and optionally other biologically active compounds or agents as component (c) in the present compositions. Moreover, process intermediates useful for preparing compounds of Formula 1, such as compounds of Formulae 14, 17, 20 and 22 are correspondingly particularly useful.

The pharmacokinetic properties of compounds of Formula 1 can be measured using a wide variety of assay protocols known in the science of pharmacology. In one illustrative method involving a single oral dose, three male and three female rats receive a single dose of a test substance via oral gavage. Approximately 0.25 mL of blood is collected via tail vein immediately prior to dosing, and then at 0.25, 0.5, 1, 2, 4, 8, 12, 24 h and every 24 h thereafter until sacrifice. At sacrifice, fat is also collected to determine the fat:plasma ratio at sacrifice. Blood is collected into tubes that contain ethylenediaminetetracetic acid (EDTA) and centrifuged at 2500×g in order to separate plasma from blood cells. The plasma is then extracted by protein precipitation using, for example, acetonitrile and a protein precipitation plate (e.g., Strata Impact Protein Precipitation Plate, part number CEO-7565 of Phenomenex, Torrance, Calif., U.S.A.) following directions provided for the plate. Alternatively, the plasma is extracted just with acetonitrile, vortexed (i.e. mixed using a vortex mixer), and centrifuged to pellet the proteins. After removal of the proteins, the plasma is analyzed for parent compound and/or metabolites by liquid chromatography-mass spectrometry (LC/MS). The fat is homogenized and extracted by an organic solvent such as acetonitrile. The extract is then analyzed for parent compound and/or metabolites by LC/MS. The plasma pharmacokinetic data is then analyzed using nonlinear modeling software (e.g., WinNonlin™ from Pharsight, Cary, N.C., U.S.A.) to determine half-life of the administered compound in plasma, the time after administration when the maximum plasma concentration is reached ($T_{max}$), the maximum plasma concentration ($C_{max}$) and the area under the plasma concentration curve (AUC). As analysis of fat requires rat sacrifice, fat data is obtained at single time points (i.e. the time of rat sacrifice). However, by using multiple rats sacrificed after different intervals from time of dosing, such parameters as $C_{max}$ for fat are determined. Using the above described method, Compounds 3, 4 and 5 identified in Index Table A are found to have a significantly diminished distribution into fat compared to corresponding compounds wherein the phenyl ring connected to R¹ and R² has a nonhydrogen substituent at the para position relative to the bond connecting the phenyl ring to the remainder of the molecule.

In a composition comprising (a) at least one compound selected from Formula 1, N-oxides, and salts thereof, with (b) at least one fungicidal compound selected from component (b), component (b) is selected from components (b1) through (b13), i.e. Formulae B1 through B13, respectively, including salts thereof.

Component (b1) relates to the compound of Formula B1

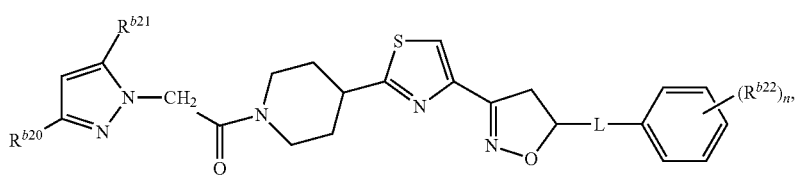

B1 wherein $R^{b20}$ and $R^{b21}$ are independently $CH_3$, $CF_2H$ or $CF_3$; each $R^{b22}$ is independently halogen or cyano; n is 0, 1, 2 or 3; and L is a direct bond or —$CH_2O$— wherein the left bond is connected to the dihydroisoxazole ring and the right bond is connected to the phenyl ring. Of note as an example of a compound of Formula B1 wherein L is a direct bond is (b1a) the compound of Formula B1a

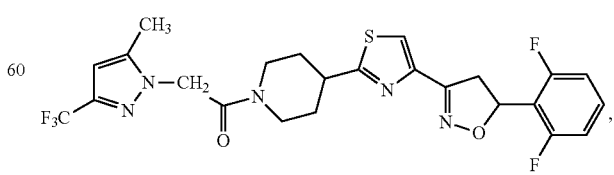

B1a which is 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone (Registry Number 1003318-67-9). Of particular note is (b1aa) the R enantiomer of Formula B1a-R

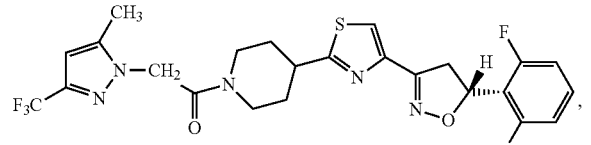
B1a-R which is 1-[4-[4-[5R-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone (Registry Number 1003319-79-6). Examples of a compound of Formula B1 wherein L is —CH$_2$O— include (b1b) the compound of Formula B1b

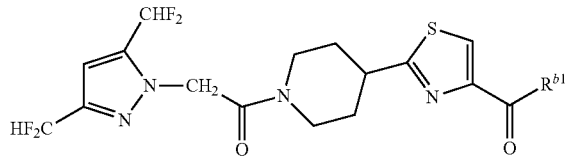
B1b which is 1-[4-[4-[5-[(2,6-difluorophenoxy)methyl]-4,5-dihydro-3-isoxazolyl]-2-thiazolyl]-1-piperdinyl-2-[5-methyl-3-(trifluoromethyl)-1H-pyrazol-1-yl]ethanone. Methods for preparing compounds of Formula B1 are described in PCT Patent Publication WO 2008/013622 and PCT Patent Application PCT/US11/64324.

Component (b2) relates to a compound of Formula B2

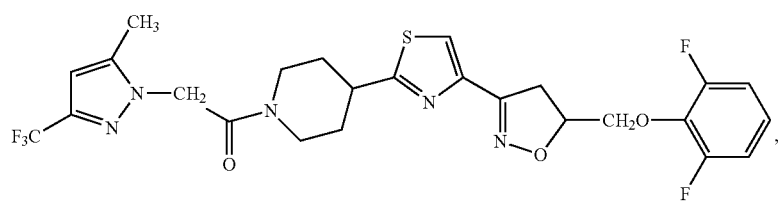
B2 wherein $R^{b1}$ is

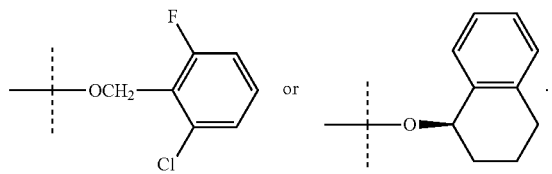

Examples of a compound of Formula B2 include (b2a) (2-chloro-6-fluorophenyl)methyl 2-[1-[2-[3,5-bis(difluoromethyl)-1H-pyrazol-1-yl]acetyl]-4-piperidinyl]-4-thiazolecarboxylate (Registry Number 1299409-40-7) and (b2b) (1R)-1,2,3,4-tetrahydro-1-naphthalenyl 2-[1-[2-[3,5-bis(difluoromethyl)-1H-pyrazol-1-yl]acetyl]-4-piperidinyl]-4-thi- azolecarboxylate (Registry Number 1299409-42-9). Methods for preparing compounds of Formula B2 are described in PCT Patent Publications WO 2009/132785 and WO 2011/051243.

Component (b3) relates to a compound of Formula B3

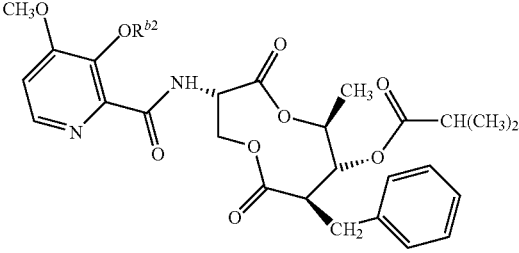
B3 wherein $R^{b2}$ is —CH$_2$OC(O)CH(CH$_3$)$_2$, —C(O)CH$_3$, —CH$_2$OC(O)CH$_3$, —C(O)OCH$_2$CH(CH$_3$)$_2$ or Examples of a compound of Formula B3 include (b3a) [[4-methoxy-2-[[[(3S,7R,8R,9S)-9-methyl-8-(2-methyl-1-oxopropoxy)-2,6-dioxo-7-(phenylmethyl)-1,5-dioxonan-3-yl]-amino]carbonyl]-3-pyridinyl]oxy]methyl 2-methylpropanoate (Registry Number 517875-34-2), (b3b) (3S,6S,7R,8R)-3-[[[3-(acetyloxy)-4-methoxy-2-pyridinyl]carbonyl]amino]-6-methyl-4,9-dioxo-8-(phenylmethyl)-1,5-dioxonan-7-yl 2-methylpropanoate (Registry Number 234112-93-7), (b3c) (3S,6S,7R,8R)-3-[[[3-[(acetyloxy)methyl]-4-methoxy-2-pyridinyl]carbonyl]amino]-6-methyl-4,9-dioxo-8-(phenylmethyl)-1,5-dioxonan-7-yl 2-methylpropanoate (Registry Number 517875-31-9), (b3d) (3S,6S,7R,8R)-3-[[[4-methoxy-3-[[(2-methylpropoxy)carbonyl]oxy]-2-pyridinyl]carbonyl]amino]-6-methyl-4,9-dioxo-8-(phenylmethyl)-1,5-dioxonan-7-yl 2-methylpropanoate (Registry Number 328256-72-0), and (b3e) N-[[3-(1,3-benzodioxol-5-ylmethoxy)-4-methoxy-2-pyridinyl]carbonyl]-O-[2,5-dideoxy-3-O-(2-methyl-1-oxopropyl)-2-(phenylmethyl)-L-arabinonoyl]-L-serine, (1→4')-lactone (Registry Number 1285706-70-8). Methods for preparing compounds of Formula B3 are described in PCT Patent Publications WO 99/40081, WO 2001/014339, WO 2003/035617 and WO 2011044213.

Component (b4) relates to a compound of Formula B4

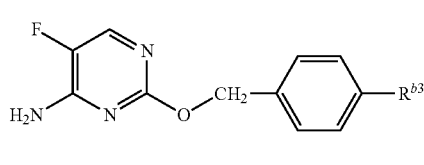

wherein R$^{b3}$ is CH$_3$ or F.

Examples of a compound of Formula B4 include (b4a) 5-fluoro-2-[(4-methylphenyl)-methoxy]-4-pyrimidinamine (Registry Number 1174376-25-0) and (b4b) 5-fluoro-2-[(4-fluorophenyl)methoxy]-4-pyrimidinamine (Registry Number 1174376-11-4). Compounds of Formula B4 can be prepared by methods described in PCT Patent Publication WO 2009/094442.

Component (b5) relates to the compound of Formula B5

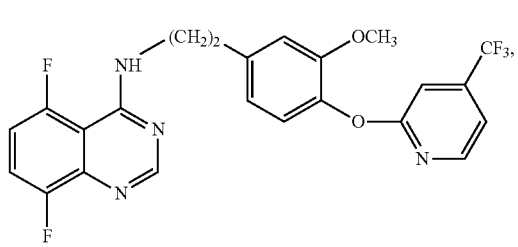

which is 5,8-difluoro-N-[2-[3-methoxy-4-[[4-(trifluoromethyl)-2-pyridinyl]oxy]phenyl]-ethyl]-4-quinazolinamine (Registry Number 1210070-31-7). The compound of Formula B5 can be prepared by methods described in PCT Patent Publication WO 2010/025451.

Component (b6) relates to a compound of Formula B6

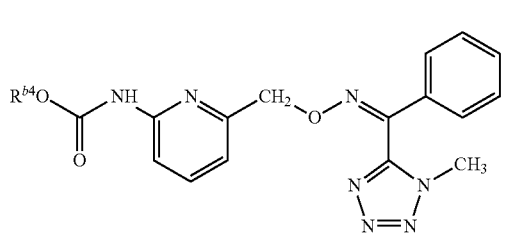

wherein R$^{b4}$ is —(CH$_2$)$_4$CH$_3$, —C(CH$_3$)$_3$ or —(CH$_2$)$_2$C≡CH.

Examples of a compound of Formula B6 include (b6a) pentyl[6-[[[(Z)-[(1-methyl-1H-tetrazol-5-yl)phenylmethylene]amino]oxy]methyl]-2-pyridinyl]carbamate (Registry Number 500207-05-6), (b6b) 1,1-dimethylethyl N-[6-[[[(Z)-[(1-methyl-1H-tetrazol-5-yl)-phenylmethylene]amino]oxy]methyl]-2-pyridinyl]carbamate (Registry Number 500207-04-5), and (b6c) 3-butyn-1-yl N-[6-[[[(Z)-[(1-methyl-1H-tetrazol-5-yl)phenylmethylene]amino]-oxy]methyl]-2-pyridinyl]carbamate (Registry Number 1202946-82-4). Compounds of Formula B6 can be prepared by methods described in PCT Patent Publication WO 2003/016303.

Component (b7) relates to the compound of Formula B7

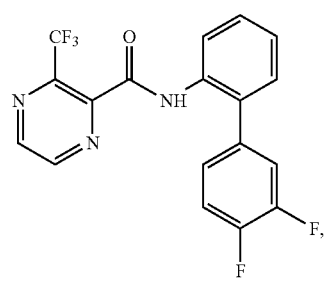

which is N-(3',4'-difluoro[1,1'-biphenyl]-2-yl)-3-(trifluoromethyl)-2-pyrazinecarboxamide (Registry Number 942515-63-1). The compound of Formula B7 can be prepared by methods described in PCT Patent Publication WO 2007/072999.

Component (b8) relates to the compound of Formula B8

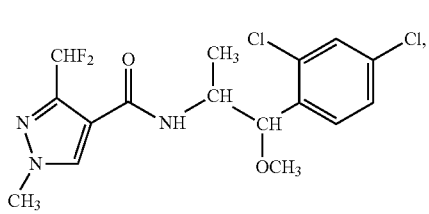

which is N-[2-(2,4-dichlorophenyl)-2-methoxy-1-methylethyl]-3-(difluoromethyl)-1-methyl-1H-pyrazole-4-carboxamide (Registry Number 1092400-95-7). The compound of Formula B8 can be prepared by methods described in PCT Patent Publication WO 2008/148570.

Component (b9) relates to a compound of Formula B9

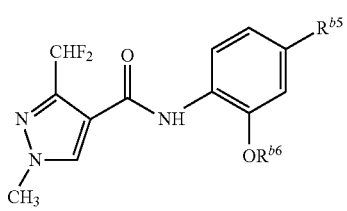

wherein R$^{b5}$ is H or F, and R$^{b6}$ is —CF$_2$CHFCF$_3$ or —CF$_2$CF$_2$H. Examples of a compound of Formula B9 are (b9a) 3-(difluoromethyl)-N-[4-fluoro-2-(1,1,2,3,3,3-hexafluoropropoxy)-phenyl]-1-methyl-1H-pyrazole-4-carboxamide (Registry Number 1172611-40-3) and (b9b) 3-(difluoromethyl)-1-methyl-N-[2-(1,1,2,2-tetrafluoroethoxy)phenyl]-1H-pyrazole-4-carboxamide (Registry Number 923953-98-4). Compounds of Formula B9 can be prepared by methods described in PCT Patent Publication WO 2007/017450.

Component (b10) relates to a compound of Formula B10

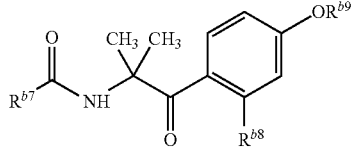

B10 wherein
$R^{b7}$ is

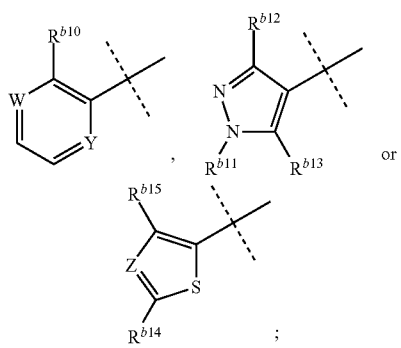

$R^{b8}$ is H, halogen or $C_1$-$C_2$ alkyl;
$R^{b9}$ is $C_1$-$C_8$ alkyl, $C_1$-$C_8$ haloalkyl or $C_2$-$C_8$ alkoxyalkyl;
$R^{b10}$ is halogen, $C_1$-$C_2$ alkyl or $C_1$-$C_2$ haloalkyl;
$R^{b11}$ is halogen, $C_1$-$C_2$ alkyl or $C_1$-$C_2$ haloalkyl;
$R^{b12}$ is $C_1$-$C_2$ alkyl;
$R^{b13}$ is H, halogen or $C_1$-$C_2$ alkyl;
$R^{b14}$ is $C_1$-$C_2$ alkyl or $C_1$-$C_2$ haloalkyl;
$R^{b15}$ is H, $C_1$-$C_2$ alkyl or $C_1$-$C_2$ haloalkyl;
W is CH or N;
Y is CH or N; and
Z is CH or N.

Component (b10a) relates to isofetamid (IKF-5411), which is N-[1,1-dimethyl-2-[2-methyl-4-(1-methylethoxy)phenyl]-2-oxoethyl]-3-methyl-2-thiophenecarboxamide (Registry Number 875915-78-9), i.e. the compound of Formula B10a B10a This compound as well as the compounds of Component (b10) can be prepared by methods described in PCT Patent Publications WO 2006/016708 and WO 2007/069777.

Component (b10b) relates to tolprocarb (MTF-0301), which is 2,2,2-trifluoroethyl N-[(1S)-2-methyl-1-[[(4-methylbenzoyl)amino]methyl]propyl]carbamate (Registry Number 911499-62-2), i.e. the compound of Formula B10b B10b This compound can be prepared by methods described in US Patent Publication US 2007/0049635 A1.

Component (b11) relates to the compound of Formula B11

B11 which is (αR)-2-[(2,5-dimethylphenoxy)methyl]-α-methoxy-N-methylbenzeneacetamide (Registry Number 394657-24-0). The compound of Formula B11 can be prepared by methods described in PCT Patent Publication WO 95/27693.

Component (b12) relates to the compound of Formula B12

B12 which is 2,6-dimethyl-1H,5H-[1,4]dithiino[2,3-c:5,6-c'] dipyrrole-1,3,5,7(2H,6H)-tetrone (Registry Number 16114-35-5). The compound of Formula B12 can be prepared by methods described in U.S. Pat. No. 3,364,229.

Component (b13) relates to the compound of Formula B13

B13 which is N-cyclopropyl-3-(difluoromethyl)-5-fluoro-1-methyl-N-[[2-(1-methylethyl)phenyl]-methyl]-1H-pyrazole-4-carboxamide (Registry Number 1255733-83-5). The compound of Formula B13 can be prepared by methods described in PCT Patent Publication WO 2010/130767.

Compositions comprising a combination of (a) at least one compound selected from the compounds of Formula 1, including N-oxides and salts thereof, together with (b) at least one fungicidal component selected from Formulae B1 through B13, including salts thereof, described above typically will provide improved control (i.e. prevention and/or cure) of plant disease from synergic contributions of components (a) and (b). The improved plant disease control may be manifest by a broader spectrum or longer duration of plant disease control, or retardation of resistance development. The contributions of components (a) and (b) may be complementarily additive or even greater than additive through synergistic interaction.

This invention also relates to a fungicidal composition comprising: (a) at least one compound selected from the compounds of Formula 1, (b) at least one fungicidal compound selected from Formulae B1 through B13 described above, and (c) further comprising at least one additional compound or agent that is biologically active. Thus compositions of component (a) with component (b) can be further mixed with (c) one or more other biologically active compounds or agents including insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multicomponent pesticide giving an even broader spectrum of agricultural protection. General references for these agricultural protectants include *The Pesticide Manual,* 13th Edition, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

A more particular aspect relates to said fungicidal composition wherein component (c) comprises at least one additional compound that is a fungicide (i.e. an additional fungicidal compound). In the present composition, additional fungicidal compounds in component (c) are typically selected from the group consisting of (c1) methyl benzimidazole carbamate (MBC) fungicides; (c2) dicarboximide fungicides; (c3) demethylation inhibitor (DMI) fungicides; (c4) phenylamide fungicides; (c5) amine/morpholine fungicides; (c6) phospholipid biosynthesis inhibitor fungicides; (c7) carboxamide fungicides; (c8) hydroxy(2-amino-)pyrimidine fungicides; (c9) anilinopyrimidine fungicides; (c10) N-phenyl carbamate fungicides; (c11) quinone outside inhibitor (QoI) fungicides; (c12) phenylpyrrole fungicides; (c13) quinoline fungicides; (c14) lipid peroxidation inhibitor fungicides; (c15) melanin biosynthesis inhibitors-reductase (MBI-R) fungicides; (c16) melanin biosynthesis inhibitors-dehydratase (MBI-D) fungicides; (c17) hydroxyanilide fungicides; (c18) squalene-epoxidase inhibitor fungicides; (c19) polyoxin fungicides; (c20) phenylurea fungicides; (c21) quinone inside inhibitor (QiI) fungicides; (c22) benzamide fungicides; (c23) enopyranuronic acid antibiotic fungicides; (c24) hexopyranosyl antibiotic fungicides; (c25) glucopyranosyl antibiotic: protein synthesis fungicides; (c26) glucopyranosyl antibiotic: trehalase and inositol biosynthesis fungicides; (c27) cyanoacetamideoxime fungicides; (c28) carbamate fungicides; (c29) oxidative phosphorylation uncoupling fungicides; (c30) organo tin fungicides; (c31) carboxylic acid fungicides; (c32) heteroaromatic fungicides; (c33) phosphonate fungicides; (c34) phthalamic acid fungicides; (c35) benzotriazine fungicides; (c36) benzene-sulfonamide fungicides; (c37) pyridazinone fungicides; (c38) thiophene-carboxamide fungicides; (c39) pyrimidinamide fungicides; (c40) carboxylic acid amide (CAA) fungicides; (c41) tetracycline antibiotic fungicides; (c42) thiocarbamate fungicides; (c43) benzamide fungicides; (c44) host plant defense induction fungicides; (c45) multi-site contact activity fungicides; (c46) fungicides other than fungicides of component (a) and components (c1) through (c45); and salts of compounds of (c1) through (c46).

Of note are fungicide composition embodiments wherein component (c) comprises at least one fungicidal compound from each of two different groups selected from (c1) through (c46).

"Methyl benzimidazole carbamate (MBC) fungicides (c1)" (FRAC (Fungicide Resistance Action Committee) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

"Dicarboximide fungicides (c2)" (FRAC code 2) are proposed to inhibit a lipid peroxidation in fungi through interference with NADH cytochrome c reductase. Examples include chlozolinate, iprodione, procymidone and vinclozolin.

"Demethylation inhibitor (DMI) fungicides (c3)" (FRAC code 3) inhibit C14-demethylase which plays a role in sterol production. Sterols, such as ergosterol, are needed for membrane structure and function, making them essential for the development of functional cell walls. Therefore, exposure to these fungicides result in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz, pefurazoate and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

"Phenylamide fungicides (c4)" (FRAC code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl, metalaxyl-M (also known as mefenoxam). The oxazolidinones include oxadixyl. The butyrolactones include ofurace.

"Amine/morpholine fungicides (c5)" (FRAC code 5) inhibit two target sites within the sterol biosynthetic pathway, Δ⁸→Δ⁷ isomerase and Δ¹⁴ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

"Phospholipid biosynthesis inhibitor fungicides (c6)" (FRAC code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

"Carboxamide fungicides (c7)" (FRAC code 7) inhibit Complex II (succinate dehydrogenase) fungal respiration by disrupting a key enzyme in the Krebs Cycle (TCA cycle) named succinate dehydrogenase Inhibiting respiration prevents the fungus from making ATP, and thus inhibits growth and reproduction. Carboxamide fungicides include benzamide, furan carboxamide, oxathiin carboxamide, thiazole carboxamide, pyrazole carboxamide and pyridine carboxamide. The benzamides include benodanil, flutolanil and mepronil. The furan carboxamides include fenfuram. The oxathiin carboxamides include carboxin and oxycarboxin. The thiazole carboxamides include thifluzamide. The pyrazole carboxamides include bixafen, furametpyr, isopyrazam, fluxapyroxad, penthiopyrad, sedaxane (N-[2-(1S,2R)-[1,1'-bicyclopropyl]-2-ylphenyl]-3-(difluoromethyl)-1-methyl-1H-pyrazole-4-carboxamide) and penflufen (N-[2-(1,3-dimethylbutyl)phenyl]-5-fluoro-1,3-dimethyl-1H-pyrazole-4-carboxamide) (PCT Patent Publication WO 2003/010149). The pyridine carboxamides include boscalid.

"Hydroxy(2-amino-)pyrimidine fungicides (c8)" (FRAC code 8) inhibit nucleic acid synthesis by interfering with adenosine deaminase. Examples include bupirimate, dimethirimol and ethirimol.

"Anilinopyrimidine fungicides (c9)" (FRAC code 9) are proposed to inhibit biosynthesis of the amino acid methionine and to disrupt the secretion of hydrolytic enzymes that lyse plant cells during infection. Examples include cyprodinil, mepanipyrim and pyrimethanil.

"N-Phenyl carbamate fungicides (c10)" (FRAC code 10) inhibit mitosis by binding to β-tubulin and disrupting microtubule assembly. Inhibition of microtubule assembly can disrupt cell division, transport within the cell and cell structure. Examples include diethofencarb.

"Quinone outside inhibitor (QoI) fungicides (c11)" (FRAC code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides include methoxyacrylate, methoxycarbamate, oximinoacetate, oximinoacetamide and dihydrodioxazine fungicides (collectively also known as strobilurin fungicides), and oxazolidinedione, imidazolinone and benzylcarbamate fungicides. The methoxyacrylates include azoxystrobin, enestroburin (SYP-Z071) and picoxystrobin. The methoxycarbamates include pyraclostrobin and pyrametostrobin. The oximinoacetates include kresoxim-methyl, pyraoxystrobin and trifloxystrobin. The oximinoacetamides include dimoxystrobin, metominostrobin, orysastrobin and α-(methoxyimino)-N-methyl-2-[[[1-[3-(trifluoro-methyl)phenyl]ethoxy]imino]methyl]benzeneacetamide. The dihydrodioxazines include fluoxastrobin. The oxazolidinediones include famoxadone. The imidazolinones include fenamidone. The benzylcarbamates include pyribencarb.

"Phenylpyrrole fungicides (c12)" (FRAC code 12) inhibit a MAP protein kinase associated with osmotic signal transduction in fungi. Fenpiclonil and fludioxonil are examples of this fungicide class.

"Quinoline fungicides (c13)" (FRAC code 13) are proposed to inhibit signal transduction by affecting G-proteins in early cell signaling. They have been shown to interfere with germination and/or appressorium formation in fungi that cause powdery mildew diseases. Quinoxyfen is an example of this class of fungicide.

"Lipid peroxidation inhibitor fungicides (c14)" (FRAC code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbons include biphenyl, chloroneb, dicloran, quintozene, tecnazene and tolclofos-methyl. The 1,2,4-thiadiazoles include etridiazole.

"Melanin biosynthesis inhibitors-reductase (MBI-R) fungicides (c15)" (FRAC code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

"Melanin biosynthesis inhibitors-dehydratase (MBI-D) fungicides (c16)" (FRAC code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

"Hydroxyanilide fungicides (c17)" (FRAC code 17) inhibit C4-demethylase which plays a role in sterol production. Examples include fenhexamid.

"Squalene-epoxidase inhibitor fungicides (c18)" (FRAC code 18) inhibit squalene-epoxidase in ergosterol biosynthesis pathway. Sterols such as ergosterol are needed for membrane structure and function, making them essential for the development of functional cell walls. Therefore exposure to these fungicides result in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

"Polyoxin fungicides (c19)" (FRAC code 19) inhibit chitin synthase. Examples include polyoxin.

"Phenylurea fungicides (c20)" (FRAC code 20) are proposed to affect cell division. Examples include pencycuron.

"Quinone inside inhibitor (QiI) fungicides (c21)" (FRAC code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi. Inhibiting mitochondrial respiration prevents normal fungal growth and development.

Quinone inside inhibitor fungicides include cyanoimidazole and sulfamoyltriazole fungicides. The cyanoimidazoles include cyazofamid. The sulfamoyltriazoles include amisulbrom.

"Benzamide fungicides (c22)" (FRAC code 22) inhibit mitosis by binding to β-tubulin and disrupting microtubule assembly. Inhibition of microtubule assembly can disrupt cell division, transport within the cell and cell structure. Examples include zoxamide.

"Enopyranuronic acid antibiotic fungicides (c23)" (FRAC code 23) inhibit growth of fungi by affecting protein biosynthesis. Examples include blasticidin-S.

"Hexopyranosyl antibiotic fungicides (c24)" (FRAC code 24) inhibit growth of fungi by affecting protein biosynthesis. Examples include kasugamycin.

"Glucopyranosyl antibiotic: protein synthesis fungicides (c25)" (FRAC code 25) inhibit growth of fungi by affecting protein biosynthesis. Examples include streptomycin.

"Glucopyranosyl antibiotic: trehalase and inositol biosynthesis fungicides (c26)" (FRAC code 26) inhibit trehalase in inositol biosynthesis pathway. Examples include validamycin.

"Cyanoacetamideoxime fungicides (c27)" (FRAC code 27) include cymoxanil.

"Carbamate fungicides (c28)" (FRAC code 28) are considered multi-site inhibitors of fungal growth. They are proposed to interfere with the synthesis of fatty acids in cell membranes, which then disrupts cell membrane permeability. Propamacarb, iodocarb, and prothiocarb are examples of this fungicide class.

"Oxidative phosphorylation uncoupling fungicides (c29)" (FRAC code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

"Organo tin fungicides (c30)" (FRAC code 30) inhibit adenosine triphosphate (ATP) synthase in oxidative phosphorylation pathway. Examples include fentin acetate, fentin chloride and fentin hydroxide.

"Carboxylic acid fungicides (c31)" (FRAC code 31) inhibit growth of fungi by affecting deoxyribonucleic acid (DNA) topoisomerase type II (gyrase). Examples include oxolinic acid.

"Heteroaromatic fungicides (c32)" (FRAC code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

"Phosphonate fungicides (c33)" (FRAC code 33) include phosphorous acid and its various salts, including fosetyl-aluminum.

"Phthalamic acid fungicides (c34)" (FRAC code 34) include teclofthalam.

"Benzotriazine fungicides (c35)" (FRAC code 35) include triazoxide.

"Benzene-sulfonamide fungicides (c36)" (FRAC code 36) include flusulfamide.

"Pyridazinone fungicides (c37)" (FRAC code 37) include diclomezine.

"Thiophene-carboxamide fungicides (c38)" (FRAC code 38) are proposed to affect ATP production. Examples include silthiofam.

"Pyrimidinamide fungicides (c39)" (FRAC code 39) inhibit growth of fungi by affecting phospholipid biosynthesis and include diflumetorim.

"Carboxylic acid amide (CAA) fungicides (c40)" (FRAC code 40) are proposed to inhibit phospholipid biosynthesis and cell wall deposition. Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb and valifenalate (valiphenal). The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)-amino]butanamide and N-[2-[4-[[3-(4-chlorophenyl)-2-propyn-1-yl]oxy]-3-methoxyphenyl]-ethyl]-3-methyl-2-[(ethylsulfonyl)amino]butanamide.

"Tetracycline antibiotic fungicides (c41)" (FRAC code 41) inhibit growth of fungi by affecting complex 1 nicotinamide adenine dinucleotide (NADH) oxidoreductase. Examples include oxytetracycline.

"Thiocarbamate fungicides (c42)" (FRAC code 42) include methasulfocarb.

"Benzamide fungicides (c43)" (FRAC code 43) inhibit growth of fungi by delocalization of spectrin-like proteins. Examples include acylpicolide fungicides such as fluopicolide and fluopyram.

"Host plant defense induction fungicides (c44)" (FRAC code P) induce host plant defense mechanisms. Host plant defense induction fungicides include benzo-thiadiazole, benzisothiazole and thiadiazole-carboxamide fungicides. The benzo-thiadiazoles include acibenzolar-S-methyl. The benzisothiazoles include probenazole. The thiadiazole-carboxamides include tiadinil and isotianil.

"Multi-site contact fungicides (c45)" inhibit fungal growth through multiple sites of action and have contact/preventive activity. This class of fungicides includes: "copper fungicides (c45.1) (FRAC code M1)", "sulfur fungicides (c45.2) (FRAC code M2)", "dithiocarbamate fungicides (c45.3) (FRAC code M3)", "phthalimide fungicides (c45.4) (FRAC code M4)", "chloronitrile fungicides (c45.5) (FRAC code M5)", "sulfamide fungicides (c45.6) (FRAC code M6)", "guanidine fungicides (c45.7) (FRAC code M7)" "triazine fungicides (c45.8) (FRAC code M8)" and "quinone fungicides (c45.9) (FRAC code M9)". "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolylfluanid. "Guanidine fungicides" include dodine, guazatine and iminoctadine. "Triazine fungicides" include anilazine. "Quinone fungicides" include dithianon.

"Fungicides other than fungicides of component (a) and components (c1) through (c45); (c46)" include certain fungicides whose mode of action may be unknown. These include: (c46.1) "thiazole carboxamide fungicides" (FRAC code U5), (c46.2) "phenyl-acetamide fungicides" (FRAC code U6), (c46.3) "quinazolinone fungicides" (FRAC code U7), (c46.4) "benzophenone fungicides" (FRAC code U8)

and (c46.5) "triazolopyrimidylamine fungicides" (FRAC code 45). The thiazole carboxamides include ethaboxam. The phenyl-acetamides include cyflufenamid and N-[[(cyclopropyl-methoxy)amino][6-(difluoromethoxy)-2,3-difluorophenyl]-methylene]benzeneacetamide. The quinazolinones include proquinazid and 2-butoxy-6-iodo-3-propyl-4H-1-benzopyran-4-one. The benzophenones include metrafenone and pyriofenone. The triazolopyrimidylamines include ametoctradin and are believed to inhibit Complex III mitochondrial respiration by binding to an unelucidated site on ubiquinone-cytochrome bc1 reductase. The (c46) class also includes bethoxazin, neo-asozin (ferric methanearsonate), fenpyrazamine, pyrrolnitrin, quinomethionate, tebufloquin, 2-[[2-fluoro-5-(trifluoromethyl)phenyl]thio]-2-[3-(2-methoxyphenyl)-2-thiazolidinylidene]acetonitrile, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]carbamate, 5-chloro-6-(2,4,6-trifluorophenyl)-7-(4-methylpiperidin-1-yl) [1,2,4]triazolo[1,5-a]pyrimidine, N-(4-chloro-2-nitrophenyl)-N-ethyl-4-methylbenzenesulfonamide, N'-[4-[4-chloro-3-(trifluoromethyl)phenoxy]-2,5-dimethylphenyl]-N-ethyl-N-methylmethanimidamide and 1-[(2-propenylthio)carbonyl]-2-(1-methylethyl)-4-(2-methylphenyl)-5-amino-1H-pyrazol-3-one.

"Fungicides other than fungicides of component (a) and components (c1) through (c45); (c46)" also include (c46.5) 6-quinolinyloxyacetamide compounds of Formula C1 and salts thereof

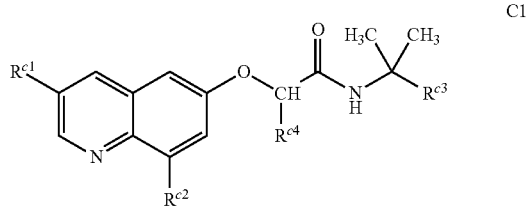

C1 wherein
$R^{c1}$ is halogen, $C_1$-$C_4$ alkoxy or $C_1$-$C_4$ alkynyl;
$R^{c2}$ is H, halogen or $C_1$-$C_4$ alkyl;
$R^{c3}$ is $C_1$-$C_{12}$ alkyl, $C_1$-$C_{12}$ haloalkyl, $C_1$-$C_{12}$ alkoxy, $C_2$-$C_{12}$ alkoxyalkyl, $C_2$-$C_{12}$ alkenyl, $C_2$-$C_{12}$ alkynyl, $C_4$-$C_{12}$ alkoxyalkenyl, $C_4$-$C_{12}$ alkoxyalkynyl, $C_1$-$C_{12}$ alkylthio or $C_2$-$C_{12}$ alkylthioalkyl;
$R^{c4}$ is methyl or $Y^{c1}$—$R^{c5}$;
$R^{c5}$ is $C_1$-$C_2$ alkyl; and
$Y^{c1}$ is $CH_2$, O or S.

Compounds of Formula C1, their use as fungicides and methods of preparation are generally known; see, for example, PCT Patent Publications WO 2004/047538, WO 2004/108663, WO 2006/058699, WO 2006/058700, WO 2008/110355, WO 2009/030469, WO 2009/049716 and WO 2009/087098. Examples of compounds of Formula C1 include: 2-[(3-bromo-6-quinolinyl)oxy]-N-(1,1-dimethyl-2-butyn-1-yl)-2-(methylthio)acetamide, 2-[(3-ethynyl-6-quinolinyl)oxy]-N-[1-(hydroxymethyl)-1-methyl-2-propyn-1-yl]-2-(methyl-thio)acetamide, N-(1,1-dimethyl-2-butyn-1-yl)-2-[(3-ethynyl-6-quinolinyl)oxy]-2-(methyl-thio)acetamide, 2-[(3-bromo-8-methyl-6-quinolinyl)oxy]-N-(1,1-dimethyl-2-propyn-1-yl)-2-(methylthio)acetamide and 2-[(3-bromo-6-quinolinyl)oxy]-N-(1,1-dimethylethyl)-butanamide.

"Fungicides other than fungicides of component (a) and components (c1) through (c45); (c46)" also include (c46.6) N'-[4-[[3-[(4-chlorophenyl)methyl]-1,2,4-thiadiazol-5-yl]oxy]-2,5-dimethylphenyl]-N-ethyl-N-methylmethanimidamide, which is believed to inhibit C24-methyl transferase involved in biosynthesis of sterols.

Examples of component (c) fungicidal compounds include those listed in Embodiment 31, more particularly Embodiment 32, and even more particularly Embodiment 33.

Compositions comprising a combination of (a) at least one compound selected from the compounds of Formula 1, including N-oxides and salts thereof, (b) at least one fungicidal component selected from Formulae B1 through B13, including salts thereof and (c) at least one additional fungicidal compound (e.g., (c1) through (c46) of Embodiment 30, including the corresponding fungicidal compounds described above) can provide improved control (i.e. prevention and/or cure) of plant disease from synergic contributions of components (a), (b) and (c). The improved plant disease control may be manifest by a broader spectrum or longer duration of plant disease control, or retardation of resistance development. The contributions of components (a), (b) and (c) may be complementarily additive or even greater than additive through synergistic interaction. Addition of component (c) may provide stronger synergy than resulting from combination of components (a) and (b).

In a fungicidal composition comprising (a) at least one compound selected from the compounds of Formula 1, including N-oxides and salts thereof, (b) at least one fungicidal compound selected from Formulae B1 through B13 including salts thereof, described above, and (c) further comprising at least one additional compound or agent that is biologically active, besides the fungicidal compounds (c1) through (c46) described above, component (c) can also be selected from compounds or agents having biological activity that is other than fungicidal. Examples of such biologically active compounds or agents with which compositions of component (a) with component (b), can be mixed (e.g., in an agricultural formulation) are: insecticides such as abamectin, acephate, acetamiprid, acetoprole, acrinathrin, aldicarb, amidoflumet, amitraz, avermectin, azadirachtin, azinphos-methyl, bifenthrin, bifenazate, bistrifluron, buprofezin, carbofuran, cartap, chinomethionat, chlorfenapyr, chlorfluazuron, chlorantraniliprole, chlorpyrifos, chlorpyrifos-methyl, chlorobenzilate, chromafenozide, clothianidin, cyantraniliprole, cyflumetofen, cyfluthrin, beta-cyfluthrin, cyhalothrin, gamma-cyhalothrin, lambda-cyhalothrin, cyhexatin, cypermethrin, cyromazine, deltamethrin, diafenthiuron, diazinon, dicofol, dieldrin, dienochlor, diflubenzuron, dimefluthrin, dimethoate, dinotefuran, diofenolan, emamectin, endosulfan, esfenvalerate, ethiprole, etoxazole, fenamiphos, fenazaquin, fenbutatin oxide, fenothiocarb, fenoxycarb, fenpropathrin, fenpyroximate, fenvalerate, fipronil, flonicamid, flubendiamide, flucythrinate, tau-fluvalinate, flufenerim, flufenoxuron, fonophos, halofenozide, hexaflumuron, hexythiazox, hydramethylnon, imicyafos, imidacloprid, indoxacarb, isofenphos, lufenuron, malathion, meperfluthrin, metaflumizone, metaldehyde, methamidophos, methidathion, methomyl, methoprene, methoxychlor, methoxyfenozide, metofluthrin, milbemycin oxime, monocrotophos, nicotine, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, prothiocarb, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spiridiclofen, spiromesifen, spirotetramat, sulfoxaflor, sulprofos, tebufenozide, tebufenpyrad, teflubenzuron, tefluthrin, terbufos, tetrachlorvinphos, tetramethylfluthrin, thiacloprid, thiamethoxam, thiodicarb, thiosultap-sodium, tolfenpyrad, tralomethrin, triazamate, trichlorfon, triflumuron; nematocides such as aldicarb, imicyafos, oxamyl and fenamiphos; bactericides such as streptomycin; acaricides such as amitraz, chinomethionat, chlorobenzilate, cyenopyrafen, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Of note is a composition of the present invention which comprises, in addition to a components (a) and (b), at least one invertebrate pest control compound or agent selected from the group consisting of abamectin, acephate, acetamiprid, acetoprole, acrinathrin, aldicarb, amidoflumet, amitraz, avermectin, azadirachtin, azinphos-methyl, bifenthrin, bifenazate, bistrifluron, buprofezin, carbofuran, cartap, chinomethionat, chlorfenapyr, chlorfluazuron, chlorantraniliprole, chlorpyrifos, chlorpyrifos-methyl, chlorobenzilate, chromafenozide, clothianidin, cyantraniliprole, cyflumetofen, cyfluthrin, beta-cyfluthrin, cyhalothrin, gamma-cyhalothrin, lambda-cyhalothrin, cyhexatin, cypermethrin, cyromazine, deltamethrin, diafenthiuron, diazinon, dicofol, dieldrin, dienochlor, diflubenzuron, dimefluthrin, dimethoate, dinotefuran, diofenolan, emamectin, endosulfan, esfenvalerate, ethiprole, etoxazole, fenamiphos, fenazaquin, fenbutatin oxide, fenothiocarb, fenoxycarb, fenpropathrin, fenpyroximate, fenvalerate, fipronil, flonicamid, flubendiamide, flucythrinate, tau-fluvalinate, flufenerim, flufenoxuron, fonophos, halofenozide, hexaflumuron, hexythiazox, hydramethylnon, imicyafos, imidacloprid, indoxacarb, isofenphos, lufenuron, malathion, meperfluthrin, metaflumizone, metaldehyde, methamidophos, methidathion, methomyl, methoprene, methoxychlor, methoxyfenozide, metofluthrin, milbemycin oxime, monocrotophos, nicotine, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spiridiclofen, spiromesifen, spirotetramat, sulfoxaflor, sulprofos, tebufenozide, tebufenpyrad, teflubenzuron, tefluthrin, terbufos, tetrachlorvinphos, tetramethylfluthrin, thiacloprid, thiamethoxam, thiodicarb, thiosultap-sodium, tolfenpyrad, tralomethrin, triazamate, trichlorfon, triflumuron, *Bacillus thuringiensis* subsp. *aizawai*, *Bacillus thuringiensis* subsp. *kurstaki*, nucleopolyhedro viruses, encapsulated delta-endotoxins of *Bacillus thuringiensis*, baculoviruses, entomopathogenic bacteria, entomopathogenic viruses and entomopathogenic fungi.

In certain instances, combinations of a mixture of components (a) and (b) fungicidal compounds with invertebrate pest control compounds or agents (i.e. as component (c) biologically active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load. Synergism can also result in increased plant disease control or protection.

In the fungicidal compositions of the present invention, component (a) (i.e. at least one compound selected from compounds of Formula 1, N-oxides, and salts thereof) and component (b) are present in fungicidally effective amounts. The weight ratio of component (a) to component (b) (i.e. one or more additional fungicidal compounds) is generally between about 1:3000 to about 3000:1, more typically between about 1:500 and about 500:1. Of note are compositions where in the weight ratio of component (a) to component (b) is from about 125:1 to about 1:125. With many fungicidal compounds of component (b), these compositions are particularly effective for controlling plant diseases caused by fungal plant pathogens. Of particular note are compositions wherein the weight ratio of component (a) to component (b) is from about 25:1 to about 1:25, or from about 5:1 to about 1:5. One skilled in the art can easily determine through simple experimentation the weight ratios and application rates of fungicidal compounds necessary for the desired spectrum of fungicidal protection and control.

Table A1 lists specific combinations of a Component (b) compound with Compound 1 as Component (a) illustrative of the mixtures, compositions and methods of the present invention. (Compound numbers refer to compounds in Index Table A.) The second column of Table A1 lists the specific Component (b) compound (e.g., "1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone (b1a)" in the first line). The third, fourth and fifth columns of Table A1 lists ranges of weight ratios for rates at which the Component (a) compound is typically applied to a field-grown crop relative to Component (b). Thus, for example, the first line of Table A1 specifically discloses the combination of Compound 1 with Component (b1a) is typically applied in a weight ratio of Compound 1 to Component (b1a) of between 400:1 and 1:1. The remaining lines of Table A1 are to be construed similarly.

TABLE A1

| Component (a) | Component (b) | Typical Weight Ratio | More Typical Weight Ratio | Most Typical Weight Ratio |
|---|---|---|---|---|
| Compound 1 | 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]-ethanone (b1a) | 400:1 to 1:1 | 100:1 to 4:1 | 50:1 to 8:1 |

TABLE A1-continued

| Component (a) | Component (b) | Typical Weight Ratio | More Typical Weight Ratio | Most Typical Weight Ratio |
|---|---|---|---|---|
| Compound 1 | 1-[4-[4-[5R-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]-ethanone (b1aa) | 800:1 to 2:1 | 200:1 to 8:1 | 100:1 to 16:1 |
| Compound 1 | 1-[4-[4-[5-[(2,6-difluorophenoxy)methyl]-4,5-dihydro-3-isoxazolyl]-2-thiazolyl]-1-piperdinyl]-2-[5-methyl-3-(trifluoromethyl)-1H-pyrazol-1-yl]ethanone (b1b) | 400:1 to 1:1 | 100:1 to 4:1 | 50:1 to 8:1 |
| Compound 1 | (2-chloro-6-fluorophenyl)methyl 2-[1-[2-[3,5-bis(difluoromethyl)-1H-pyrazol-1-yl]acetyl]-4-piperidinyl]-4-thiazolecarboxylate (b2a) | 200:1 to 2:1 | 50:1 to 2:1 | 25:1 to 4:1 |
| Compound 1 | (1R)-1,2,3,4-tetrahydro-1-naphthalenyl 2-[1-[2-[3,5-bis(difluoromethyl)-1H-pyrazol-1-yl]acetyl]-4-piperidinyl]-4-thiazolecarboxylate (b2b) | 200:1 to 1:2 | 50:1 to 2:1 | 25:1 to 4:1 |
| Compound 1 | [[4-methoxy-2-[[[(3S,7R,8R,9S)-9-methyl-8-(2-methyl-1-oxopropoxy)-2,6-dioxo-7-(phenylmethyl)-1,5-dioxonan-3-yl]amino]-carbonyl]-3-pyridinyl]oxy]methyl 2-methylpropanoate (b3a) | 200:1 to 1:2 | 50:1 to 2:1 | 25:1 to 4:1 |
| Compound 1 | (3S,6S,7R,8R)-3-[[[3-(acetyloxy)-4-methoxy-2-pyridinyl]carbonyl]amino]-6-methyl-4,9-dioxo-8-(phenylmethyl)-1,5-dioxonan-7-yl 2-methylpropanoate (b3b) | 200:1 to 1:2 | 50:1 to 2:1 | 25:1 to 4:1 |
| Compound 1 | (3S,6S,7R,8R)-3-[[[3-[(acetyloxy)methyl]-4-methoxy-2-pyridinyl]carbonyl]amino]-6-methyl-4,9-dioxo-8-(phenylmethyl)-1,5-dioxonan-7-yl 2-methylpropanoate (b3c) | 200:1 to 1:2 | 50:1 to 2:1 | 25:1 to 4:1 |
| Compound 1 | (3S,6S,7R,8R)-3-[[[4-methoxy-3-[[(2-methyl-propoxy)carbonyl]oxy]-2-pyridinyl]-carbonyl]amino]-6-methyl-4,9-dioxo-8-(phenylmethyl)-1,5-dioxonan-7-yl 2-methylpropanoate (b3d) | 200:1 to 1:2 | 50:1 to 2:1 | 25:1 to 4:1 |
| Compound 1 | N-[[3-(1,3-benzodioxol-5-ylmethoxy)-4-methoxy-2-pyridinyl]carbonyl]-O-[2,5-dideoxy-3-O-(2-methyl-1-oxopropyl)-2-(phenylmethyl)-L-arabinonoyl]-L-serine, (1→4')-lactone (b3e) | 200:1 to 1:2 | 50:1 to 2:1 | 25:1 to 4:1 |
| Compound 1 | 5-fluoro-2-[(4-methylphenyl)methoxy]-4-pyrimidinamine (b4a) | 20:1 to 1:20 | 5:1 to 1:5 | 3:1 to 1:3 |
| Compound 1 | 5-fluoro-2-[(4-fluorophenyl)methoxy]-4-pyrimidinamine (b4b) | 20:1 to 1:20 | 5:1 to 1:5 | 3:1 to 1:3 |
| Compound 1 | 5,8-difluoro-N-[2-[3-methoxy-4-[[4-(trifluoromethyl)-2-pyridinyl]oxy]phenyl]-ethyl]-4-quinazolinamine (b5) | 40:1 to 1:10 | 10:1 to 1:3 | 5:1 to 1:2 |
| Compound 1 | pentyl [6-[[[(Z)-[(1-methyl-1H-tetrazol-5-yl)phenylmethylene]amino]oxy]methyl]-2-pyridinyl]carbamate (b6a) | 40:1 to 1:10 | 10:1 to 1:3 | 5:1 to 1:2 |
| Compound 1 | 1,1-dimethylethyl N-[6-[[[(Z)-[(1-methyl-1H-tetrazol-5-yl)phenylmethylene]amino]oxy]-methyl]-2-pyridinyl]carbamate (b6b) | 40:1 to 1:10 | 10:1 to 1:3 | 5:1 to 1:2 |
| Compound 1 | 3-butyn-1-yl N-[6-[[[(Z)-[(1-methyl-1H-tetrazol-5-yl)phenylmethylene]amino]oxy]-methyl]-2-pyridinyl]carbamate (b6c) | 40:1 to 1:10 | 10:1 to 1:3 | 5:1 to 1:2 |
| Compound 1 | N-(3',4'-difluoro[1,1'-biphenyl]-2-yl)-3-(trifluoromethyl)-2-pyrazinecarboxamide (b7) | 20:1 to 1:20 | 5:1 to 1:5 | 3:1 to 1:3 |
| Compound 1 | N-[2-(2,4-dichlorophenyl)-2-methoxy-1-methylethyl]-3-(difluoromethyl)-1-methyl-2H-pyrazole-4-carboxamide (b8) | 20:1 to 1:20 | 5:1 to 1:5 | 3:1 to 1:3 |
| Compound 1 | 3-(difluoromethyl)-N-[4-fluoro-2-(1,1,2,3,3,3-hexafluoropropoxy)phenyl]-1-methyl-1H-pyrazole-4-carboxamide (b9a) | 20:1 to 1:20 | 5:1 to 1:5 | 3:1 to 1:3 |
| Compound 1 | 3-(difluoromethyl)-1-methyl-N-[2-(1,1,2,2-tetrafluoroethoxy)phenyl]-1H-pyrazole-4-carboxamide (b9b) | 20:1 to 1:20 | 5:1 to 1:5 | 3:1 to 1:3 |
| Compound 1 | isofetamid (b10a) | 20:1 to 1:20 | 5:1 to 1:5 | 3:1 to 1:3 |
| Compound 1 | tolprocarb (b10b) | 20:1 to 1:20 | 5:1 to 1:5 | 3:1 to 1:3 |
| Compound 1 | (αR)-2-[(2,5-dimethylphenoxy)methyl]-α-methoxy-N-methylbenzeneacetamide (b11) | 20:1 to 1:20 | 5:1 to 1:5 | 3:1 to 1:3 |
| Compound 1 | 2,6-dimethyl-1H,5H-[1,4]dithiino[2,3-c:5,6-c']dipyrrole-1,3,5,7(2H,6H)-tetrone (b12) | 1:1 to 1:400 | 1:4 to 1:100 | 1:8 to 1:50 |
| Compound 1 | N-cyclopropyl-3-(difluoromthyl)-5-fluoro-1-methyl-N-[[2-(1-methylethyl)phenyl]methyl]-1H-pyrazole-4-carboxamide (b13) | 20:1 to 1:20 | 5:1 to 1:5 | 3:1 to 1:3 |

Tables A2 through A13 are each constructed the same as Table A1 above except that entries below the "Component (a)" column heading are replaced with the respective Component (a) Column Entry shown below. Thus, for example, in Table A2 the entries below the "Component (a)" column heading all recite "Compound 2", and the first line below the column headings in Table A2 specifically discloses combination of Compound 2 with 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone. Tables A3 through A13 are constructed similarly.

| Table Number | Component (a) Column Entry |
| --- | --- |
| A2 | Compound 2 |
| A3 | Compound 3 |
| A4 | Compound 4 |
| A5 | Compound 5 |
| A6 | Compound 6 |
| A7 | Compound 7 |
| A8 | Compound 8 |
| A9 | Compound 9 |
| A10 | Compound 10 |
| A11 | Compound 11 |
| A12 | Compound 12 |

Specific mixtures are listed in Tables B1 through B13. (Compound numbers refer to compounds in Index Table A, and Component (b) is identified in Table A1.) In Table B1, each line below the column headings "Component (a)" and "Component (b)" specifically discloses a mixture of Component (a), which is Compound 1, with a Component (b) fungicidal compound. The entries under the heading "Illustrative Ratios" disclose seven specific weight ratios of Component (a) relative to Component (b) for the disclosed mixture. For example, the first line of Table B1 discloses a mixture of Compound 1 with 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone (b1) and lists weight ratios of Compound 1 relative to Component (b1) of 2:1, 4:1, 8:1, 20:1, 50:1, 100:1 or 200:1. Table B1 thus supplements with specific ratios the general ranges of ratios for the combinations disclosed in Table A1.

TABLE B1

| Component (a) | Component (b) | Illustrative Ratios | | | | | | |
| --- | --- | --- | --- | --- | --- | --- | --- | --- |
| Compound 1 | b1a | 2:1 | 4:1 | 8:1 | 20:1 | 50:1 | 100:1 | 200:1 |
| Compound 1 | b1aa | 4:1 | 8:1 | 16:1 | 40:1 | 100:1 | 200:1 | 400:1 |
| Compound 1 | b1b | 2:1 | 4:1 | 8:1 | 20:1 | 50:1 | 100:1 | 200:1 |
| Compound 1 | b2a | 1:1 | 2:1 | 4:1 | 10:1 | 25:1 | 50:1 | 100:1 |
| Compound 1 | b2b | 1:1 | 2:1 | 4:1 | 10:1 | 25:1 | 50:1 | 100:1 |
| Compound 1 | b3a | 1:1 | 2:1 | 4:1 | 10:1 | 25:1 | 50:1 | 100:1 |
| Compound 1 | b3b | 1:1 | 2:1 | 4:1 | 10:1 | 25:1 | 50:1 | 100:1 |
| Compound 1 | b3c | 1:1 | 2:1 | 4:1 | 10:1 | 25:1 | 50:1 | 100:1 |
| Compound 1 | b3d | 1:1 | 2:1 | 4:1 | 10:1 | 25:1 | 50:1 | 100:1 |
| Compound 1 | b3e | 1:1 | 2:1 | 4:1 | 10:1 | 25:1 | 50:1 | 100:1 |
| Compound 1 | b4a | 1:10 | 1:5 | 1:3 | 1:1 | 3:1 | 5:1 | 10:1 |
| Compound 1 | b4b | 1:10 | 1:5 | 1:3 | 1:1 | 3:1 | 5:1 | 10:1 |
| Compound 1 | b5 | 1:5 | 1:3 | 1:2 | 2:1 | 5:1 | 10:1 | 20:1 |
| Compound 1 | b6a | 1:5 | 1:3 | 1:2 | 2:1 | 5:1 | 10:1 | 20:1 |
| Compound 1 | b6b | 1:5 | 1:3 | 1:2 | 2:1 | 5:1 | 10:1 | 20:1 |
| Compound 1 | b6c | 1:5 | 1:3 | 1:2 | 2:1 | 5:1 | 10:1 | 20:1 |

TABLE B1-continued

| Component (a) | Component (b) | Illustrative Ratios | | | | | | |
| --- | --- | --- | --- | --- | --- | --- | --- | --- |
| Compound 1 | b7 | 1:10 | 1:5 | 1:3 | 1:1 | 3:1 | 5:1 | 10:1 |
| Compound 1 | b8 | 1:10 | 1:5 | 1:3 | 1:1 | 3:1 | 5:1 | 10:1 |
| Compound 1 | b9a | 1:10 | 1:5 | 1:3 | 1:1 | 3:1 | 5:1 | 10:1 |
| Compound 1 | b9b | 1:10 | 1:5 | 1:3 | 1:1 | 3:1 | 5:1 | 10:1 |
| Compound 1 | b10a | 1:10 | 1:5 | 1:3 | 1:1 | 3:1 | 5:1 | 10:1 |
| Compound 1 | b10b | 1:10 | 1:5 | 1:3 | 1:1 | 3:1 | 5:1 | 10:1 |
| Compound 1 | b11 | 1:10 | 1:5 | 1:3 | 1:1 | 3:1 | 5:1 | 10:1 |
| Compound 1 | b12 | 1:200 | 1:100 | 1:50 | 1:18 | 1:8 | 1:4 | 1:2 |
| Compound 1 | b13 | 1:10 | 1:5 | 1:3 | 1:1 | 3:1 | 5:1 | 10:1 |

Tables B2 through B13 are each constructed the same as Table B1 above except that entries below the "Component (a)" column heading are replaced with the respective Component (a) Column Entry shown below. Thus, for example, in Table B2 the entries below the "Component (a)" column heading all recite "Compound 2", and the first line below the column headings in Table A2 specifically discloses a mixture of Compound 2 with 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone. Tables B3 through B13 are constructed similarly. Tables B2 through B13 thus supplement with specific ratios the general ranges of ratios for the combinations disclosed in Tables A2 through A13, respectively.

| Table Number | Component (a) Column Entry |
| --- | --- |
| B2 | Compound 2 |
| B3 | Compound 3 |
| B4 | Compound 4 |
| B5 | Compound 5 |
| B6 | Compound 6 |
| B7 | Compound 7 |
| B8 | Compound 8 |
| B9 | Compound 9 |
| B10 | Compound 10 |
| B11 | Compound 11 |
| B12 | Compound 12 |

As already noted, the present invention includes embodiments wherein the composition comprising components (a) and (b) further comprises as component (c) one or more biologically active compounds or agents. Therefore embodiments of the present composition include combinations of the mixtures disclosed in Tables A1 through A12 and B1 through B13 with additional biological compounds or agents. Of note as additional biological compounds or agents are fungicidal compounds selected from (c1) through (c46) already described. The weight ratio of component (c) to component (a) is generally between about 1:3000 and about 3000:1, more typically between about 1:500 and about 500:1, between about 125:1 and about 1:125, and between about 25:1 and 1:25 and most typically between about 5:1 and about 1:5. One skilled in the art can easily determine through simple experimentation the weight ratios and application rates of fungicidal compounds necessary for the desired spectrum of plant disease protection and control.

Table C lists typical, more typical, and most typical weight ratios for specific component (c) fungicides relative to component (a) in compositions comprising components (a) and (c) either before (i.e. without component (b)) or after inclusion of component (b).

TABLE C

| Component (c) | Typical Weight Ratio | More Typical Weight Ratio | Most Typical Weight Ratio | Illustrative Weight Ratio |
|---|---|---|---|---|
| acibenzolar-S-methyl | 2:1 to 1:180 | 1:1 to 1:60 | 1:1 to 1:18 | 1:4 |
| aldimorph | 30:1 to 1:3 | 10:1 to 1:1 | 7:1 to 1:1 | 3:1 |
| ametoctradin | 9:1 to 1:18 | 3:1 to 1:6 | 3:1 to 1:3 | 1:1 |
| amisulbrom | 6:1 to 1:18 | 2:1 to 1:6 | 1:1 to 1:6 | 1:2 |
| anilazine | 90:1 to 2:1 | 30:1 to 4:1 | 22:1 to 4:1 | 8:1 |
| azaconazole | 7:1 to 1:18 | 2:1 to 1:6 | 2:1 to 1:4 | 1:2 |
| azoxystrobin | 9:1 to 1:12 | 3:1 to 1:4 | 3:1 to 1:3 | 1:1 |
| benalaxyl | 4:1 to 1:18 | 1:1 to 1:6 | 1:1 to 1:6 | 1:2 |
| benalaxyl-M | 4:1 to 1:36 | 1:1 to 1:12 | 1:1 to 1:8 | 1:3 |
| benodanil | 18:1 to 1:6 | 6:1 to 1:2 | 4:1 to 1:2 | 2:1 |
| benomyl | 45:1 to 1:4 | 15:1 to 1:1 | 11:1 to 1:1 | 4:1 |
| benthiavalicarb or benthiavalicarb-isopropyl | 2:1 to 1:36 | 1:1 to 1:12 | 1:1 to 1:12 | 1:4 |
| bethoxazin | 150:1 to 1:36 | 50:1 to 1:12 | 15:1 to 2:1 | 5:1 |
| binapacryl | 150:1 to 1:36 | 50:1 to 1:12 | 15:1 to 2:1 | 5:1 |
| biphenyl | 150:1 to 1:36 | 50:1 to 1:12 | 15:1 to 2:1 | 5:1 |
| bitertanol | 15:1 to 1:5 | 5:1 to 1:2 | 3:1 to 1:2 | 1:1 |
| bixafen | 12:1 to 1:9 | 4:1 to 1:3 | 2:1 to 1:3 | 1:1 |
| blasticidin-S | 3:1 to 1:90 | 1:1 to 1:30 | 1:4 to 1:30 | 1:12 |
| boscalid | 18:1 to 1:6 | 6:1 to 1:2 | 4:1 to 1:2 | 2:1 |
| bromuconazole | 15:1 to 1:9 | 5:1 to 1:3 | 3:1 to 1:3 | 1:1 |
| bupirimate | 3:1 to 1:90 | 1:1 to 1:30 | 1:3 to 1:30 | 1:10 |
| captafol | 90:1 to 1:4 | 30:1 to 1:2 | 15:1 to 2:1 | 5:1 |
| captan | 90:1 to 1:4 | 30:1 to 1:2 | 15:1 to 2:1 | 5:1 |
| carbendazim | 45:1 to 1:4 | 15:1 to 1:2 | 11:1 to 2:1 | 4:1 |
| carboxin | 18:1 to 1:6 | 6:1 to 1:2 | 4:1 to 1:2 | 2:1 |
| carpropamid | 15:1 to 1:9 | 5:1 to 1:3 | 3:1 to 1:3 | 1:1 |
| chloroneb | 300:1 to 2:1 | 100:1 to 4:1 | 100:1 to 14:1 | 35:1 |
| chlorothalonil | 90:1 to 1:4 | 30:1 to 1:2 | 15:1 to 2:1 | 5:1 |
| chlozolinate | 45:1 to 1:2 | 15:1 to 2:1 | 11:1 to 2:1 | 4:1 |
| clotrimazole | 15:1 to 1:9 | 5:1 to 1:3 | 3:1 to 1:3 | 1:1 |
| copper salts such as Bordeaux mixture (tribasic copper sulfate), copper oxychloride, copper sulfate and copper hydroxide | 450:1 to 1:1 | 150:1 to 4:1 | 45:1 to 5:1 | 15:1 |
| cyazofamid | 4:1 to 1:18 | 1:1 to 1:6 | 1:1 to 1:6 | 1:2 |
| cyflufenamid | 1:1 to 1:90 | 1:2 to 1:30 | 1:2 to 1:24 | 1:6 |
| cymoxanil | 6:1 to 1:18 | 2:1 to 1:6 | 1:1 to 1:5 | 1:2 |
| cyproconazole | 4:1 to 1:18 | 1:1 to 1:6 | 1:1 to 1:6 | 1:2 |
| cyprodinil | 22:1 to 1:9 | 7:1 to 1:3 | 4:1 to 1:2 | 2:1 |
| dichlofluanid | 150:1 to 1:36 | 50:1 to 1:12 | 15:1 to 2:1 | 5:1 |
| diclocymet | 150:1 to 1:36 | 50:1 to 1:12 | 15:1 to 2:1 | 5:1 |
| diclomezine | 15:1 to 1:9 | 5:1 to 1:3 | 3:1 to 1:3 | 1:1 |
| dicloran | 150:1 to 1:36 | 50:1 to 1:12 | 15:1 to 2:1 | 5:1 |
| diethofencarb | 22:1 to 1:9 | 7:1 to 1:3 | 7:1 to 1:2 | 2:1 |
| difenoconazole | 4:1 to 1:36 | 1:1 to 1:12 | 1:1 to 1:12 | 1:3 |
| diflumetorim | 150:1 to 1:36 | 50:1 to 1:12 | 15:1 to 2:1 | 5:1 |
| dimethirimol | 3:1 to 1:90 | 1:1 to 1:30 | 1:3 to 1:30 | 1:8 |
| dimethomorph | 9:1 to 1:6 | 3:1 to 1:2 | 3:1 to 1:2 | 1:1 |
| dimoxystrobin | 9:1 to 1:18 | 3:1 to 1:6 | 2:1 to 1:4 | 1:1 |
| diniconazole | 3:1 to 1:36 | 1:1 to 1:12 | 1:1 to 1:8 | 1:3 |
| diniconazole M | 3:1 to 1:90 | 1:1 to 1:30 | 1:1 to 1:12 | 1:3 |
| dinocap | 7:1 to 1:9 | 2:1 to 1:3 | 2:1 to 1:3 | 1:1 |
| dithianon | 15:1 to 1:4 | 5:1 to 1:2 | 5:1 to 1:2 | 2:1 |
| dodemorph | 30:1 to 1:3 | 10:1 to 1:1 | 7:1 to 1:1 | 3:1 |
| dodine | 30:1 to 1:2 | 10:1 to 2:1 | 10:1 to 2:1 | 4:1 |
| edifenphos | 30:1 to 1:9 | 10:1 to 1:3 | 3:1 to 1:3 | 1:1 |
| enestroburin | 9:1 to 1:18 | 3:1 to 1:6 | 2:1 to 1:4 | 1:1 |
| epoxiconazole | 3:1 to 1:36 | 1:1 to 1:12 | 1:1 to 1:7 | 1:3 |
| etaconazole | 3:1 to 1:36 | 1:1 to 1:12 | 1:1 to 1:7 | 1:3 |
| ethaboxam | 7:1 to 1:9 | 2:1 to 1:3 | 2:1 to 1:3 | 1:1 |
| ethirimol | 30:1 to 1:3 | 10:1 to 1:1 | 7:1 to 1:1 | 3:1 |
| etridazole | 30:1 to 1:9 | 10:1 to 1:3 | 7:1 to 1:2 | 2:1 |
| famoxadone | 9:1 to 1:18 | 3:1 to 1:6 | 2:1 to 1:4 | 1:1 |
| fenamidone | 6:1 to 1:18 | 2:1 to 1:6 | 2:1 to 1:4 | 1:1 |
| fenarimol | 3:1 to 1:90 | 1:1 to 1:30 | 1:2 to 1:24 | 1:7 |
| fenbuconazole | 3:1 to 1:30 | 1:1 to 1:10 | 1:1 to 1:10 | 1:3 |
| fenfuram | 18:1 to 1:6 | 6:1 to 1:2 | 4:1 to 1:2 | 1:1 |
| fenhexamid | 30:1 to 1:2 | 10:1 to 2:1 | 10:1 to 2:1 | 4:1 |
| fenoxanil | 150:1 to 1:36 | 50:1 to 1:12 | 15:1 to 1:1 | 4:1 |
| fenpiclonil | 75:1 to 1:9 | 25:1 to 1:3 | 15:1 to 2:1 | 5:1 |
| fenpropidin | 30:1 to 1:3 | 10:1 to 1:1 | 7:1 to 1:1 | 2:1 |
| fenpropimorph | 30:1 to 1:3 | 10:1 to 1:1 | 7:1 to 1:1 | 2:1 |
| fenpyrazamine | 100:1 to 1:100 | 10:1 to 1:10 | 3:1 to 1:3 | 1:1 |
| fentin salt such as the acetate, chloride or hydroxide | 15:1 to 1:9 | 5:1 to 1:3 | 3:1 to 1:3 | 1:1 |

TABLE C-continued

| Component (c) | Typical Weight Ratio | More Typical Weight Ratio | Most Typical Weight Ratio | Illustrative Weight Ratio |
|---|---|---|---|---|
| ferbam | 300:1 to 1:2 | 100:1 to 2:1 | 30:1 to 4:1 | 10:1 |
| ferimzone | 30:1 to 1:5 | 10:1 to 1:2 | 7:1 to 1:2 | 2:1 |
| fluazinam | 22:1 to 1:5 | 7:1 to 1:2 | 3:1 to 1:2 | 1:1 |
| fludioxonil | 7:1 to 1:12 | 2:1 to 1:4 | 2:1 to 1:4 | 1:1 |
| flumetover | 9:1 to 1:6 | 3:1 to 1:2 | 3:1 to 1:2 | 1:1 |
| flumorph | 9:1 to 1:18 | 3:1 to 1:6 | 3:1 to 1:3 | 1:1 |
| fluopicolide | 3:1 to 1:18 | 1:1 to 1:6 | 1:1 to 1:6 | 1:2 |
| fluopyram | 15:1 to 1:90 | 5:1 to 1:30 | 3:1 to 1:3 | 1:1 |
| fluoromide | 150:1 to 2:1 | 50:1 to 4:1 | 37:1 to 5:1 | 14:1 |
| fluoxastrobin | 4:1 to 1:18 | 1:1 to 1:6 | 1:1 to 1:6 | 1:2 |
| fluquinconazole | 4:1 to 1:12 | 1:1 to 1:4 | 1:1 to 1:4 | 1:2 |
| flusilazole | 15:1 to 1:9 | 5:1 to 1:3 | 3:1 to 1:3 | 1:1 |
| flusulfamide | 90:1 to 1:2 | 30:1 to 2:1 | 15:1 to 2:1 | 5:1 |
| flutianil | 7:1 to 1:36 | 2:1 to 1:12 | 1:1 to 1:6 | 1:2 |
| flutolanil | 18:1 to 1:6 | 6:1 to 1:2 | 4:1 to 1:2 | 1:1 |
| flutriafol | 4:1 to 1:12 | 1:1 to 1:4 | 1:1 to 1:4 | 1:2 |
| fluxapyroxad | 12:1 to 1:9 | 4:1 to 1:3 | 2:1 to 1:3 | 1:1 |
| folpet | 90:1 to 1:4 | 30:1 to 1:2 | 15:1 to 2:1 | 5:1 |
| fosetyl-aluminum | 225:1 to 2:1 | 75:1 to 5:1 | 30:1 to 5:1 | 12:1 |
| fuberidazole | 45:1 to 1:4 | 15:1 to 1:2 | 11:1 to 2:1 | 4:1 |
| furalaxyl | 15:1 to 1:45 | 5:1 to 1:15 | 1:1 to 1:6 | 1:2 |
| furametpyr | 150:1 to 1:36 | 50:1 to 1:12 | 15:1 to 2:1 | 5:1 |
| guazatine or iminoctadine | 150:1 to 1:36 | 50:1 to 1:12 | 15:1 to 2:1 | 5:1 |
| hexaconazole | 15:1 to 1:36 | 5:1 to 1:12 | 1:1 to 1:5 | 1:2 |
| hymexazol | 225:1 to 2:1 | 75:1 to 4:1 | 75:1 to 9:1 | 25:1 |
| imazalil | 7:1 to 1:18 | 2:1 to 1:6 | 1:1 to 1:5 | 1:2 |
| imibenconazole | 15:1 to 1:36 | 5:1 to 1:12 | 1:1 to 1:5 | 1:2 |
| iodocarb | 150:1 to 1:36 | 50:1 to 1:12 | 15:1 to 2:1 | 4:1 |
| ipconazole | 15:1 to 1:36 | 5:1 to 1:12 | 1:1 to 1:5 | 1:2 |
| iprobenfos | 150:1 to 1:36 | 50:1 to 1:12 | 15:1 to 2:1 | 5:1 |
| iprodione | 120:1 to 1:2 | 40:1 to 2:1 | 15:1 to 2:1 | 5:1 |
| iprovalicarb | 9:1 to 1:9 | 3:1 to 1:3 | 2:1 to 1:3 | 1:1 |
| isoprothiolane | 150:1 to 2:1 | 50:1 to 4:1 | 45:1 to 5:1 | 15:1 |
| isopyrazam | 12:1 to 1:9 | 4:1 to 1:3 | 2:1 to 1:3 | 1:1 |
| isotianil | 12:1 to 1:9 | 4:1 to 1:3 | 2:1 to 1:3 | 1:1 |
| kasugamycin | 7:1 to 1:90 | 2:1 to 1:30 | 1:2 to 1:24 | 1:7 |
| kresoxim-methyl | 7:1 to 1:18 | 2:1 to 1:6 | 2:1 to 1:4 | 1:1 |
| mancozeb | 180:1 to 1:3 | 60:1 to 2:1 | 22:1 to 3:1 | 7:1 |
| mandipropamid | 6:1 to 1:18 | 2:1 to 1:6 | 2:1 to 1:4 | 1:1 |
| maneb | 180:1 to 1:3 | 60:1 to 2:1 | 22:1 to 3:1 | 7:1 |
| mepanipyrim | 18:1 to 1:3 | 6:1 to 1:1 | 6:1 to 1:1 | 2:1 |
| mepronil | 7:1 to 1:36 | 2:1 to 1:12 | 1:1 to 1:6 | 1:2 |
| meptyldinocap | 7:1 to 1:9 | 2:1 to 1:3 | 2:1 to 1:3 | 1:1 |
| metalaxyl | 15:1 to 1:45 | 5:1 to 1:15 | 1:1 to 1:6 | 1:2 |
| metalaxyl-M | 7:1 to 1:90 | 2:1 to 1:30 | 1:1 to 1:12 | 1:4 |
| metconazole | 3:1 to 1:18 | 1:1 to 1:6 | 1:1 to 1:6 | 1:2 |
| methasulfocarb | 150:1 to 1:36 | 50:1 to 1:12 | 15:1 to 1:1 | 5:1 |
| metiram | 150:1 to 1:36 | 50:1 to 1:12 | 15:1 to 1:1 | 5:1 |
| metominostrobin | 9:1 to 1:12 | 3:1 to 1:4 | 3:1 to 1:3 | 1:1 |
| metrafenone | 6:1 to 1:12 | 2:1 to 1:4 | 2:1 to 1:4 | 1:1 |
| myclobutanil | 5:1 to 1:26 | 1:1 to 1:9 | 1:1 to 1:8 | 1:3 |
| naftifine | 150:1 to 1:36 | 50:1 to 1:12 | 15:1 to 2:1 | 5:1 |
| neo-asozin (ferric methanearsonate) | 150:1 to 1:36 | 50:1 to 1:12 | 15:1 to 2:1 | 5:1 |
| nuarimol | 15:1 to 1:9 | 5:1 to 1:3 | 3:1 to 1:3 | 1:1 |
| octhilinone | 150:1 to 1:36 | 50:1 to 1:12 | 15:1 to 1:1 | 4:1 |
| ofurace | 15:1 to 1:45 | 5:1 to 1:15 | 1:1 to 1:6 | 1:2 |
| orysastrobin | 9:1 to 1:12 | 3:1 to 1:4 | 3:1 to 1:3 | 1:1 |
| oxadixyl | 15:1 to 1:45 | 5:1 to 1:15 | 1:1 to 1:6 | 1:2 |
| oxolinic acid | 30:1 to 1:9 | 10:1 to 1:3 | 7:1 to 1:2 | 2:1 |
| oxpoconazole | 15:1 to 1:36 | 5:1 to 1:12 | 1:1 to 1:5 | 1:2 |
| oxycarboxin | 18:1 to 1:6 | 6:1 to 1:2 | 4:1 to 1:2 | 1:1 |
| oxytetracycline | 15:1 to 1:9 | 5:1 to 1:3 | 3:1 to 1:3 | 1:1 |
| pefurazoate | 150:1 to 1:36 | 50:1 to 1:12 | 15:1 to 2:1 | 5:1 |
| penconazole | 1:1 to 1:45 | 1:2 to 1:15 | 1:2 to 1:15 | 1:6 |
| pencycuron | 150:1 to 1:2 | 50:1 to 2:1 | 11:1 to 2:1 | 4:1 |
| penflufen | 12:1 to 1:9 | 4:1 to 1:3 | 2:1 to 1:3 | 1:1 |
| penthiopyrad | 12:1 to 1:9 | 4:1 to 1:3 | 2:1 to 1:3 | 1:1 |
| phosphorous acid and salts thereof | 150:1 to 1:36 | 50:1 to 1:12 | 15:1 to 2:1 | 6:1 |
| phthalide | 150:1 to 1:36 | 50:1 to 1:12 | 15:1 to 2:1 | 6:1 |
| picoxystrobin | 7:1 to 1:18 | 2:1 to 1:6 | 1:1 to 1:5 | 1:2 |
| piperalin | 15:1 to 1:9 | 5:1 to 1:3 | 3:1 to 1:3 | 1:1 |
| polyoxin | 15:1 to 1:9 | 5:1 to 1:3 | 3:1 to 1:3 | 1:1 |
| probenazole | 15:1 to 1:9 | 5:1 to 1:3 | 3:1 to 1:3 | 1:1 |
| prochloraz | 22:1 to 1:4 | 7:1 to 1:1 | 7:1 to 1:2 | 2:1 |
| procymidone | 45:1 to 1:3 | 15:1 to 1:1 | 11:1 to 2:1 | 4:1 |

TABLE C-continued

| Component (c) | Typical Weight Ratio | More Typical Weight Ratio | Most Typical Weight Ratio | Illustrative Weight Ratio |
|---|---|---|---|---|
| propamocarb or propamocarb-hydrochloride | 30:1 to 1:2 | 10:1 to 2:1 | 10:1 to 2:1 | 4:1 |
| propiconazole | 4:1 to 1:18 | 1:1 to 1:6 | 1:1 to 1:5 | 1:2 |
| propineb | 45:1 to 1:2 | 15:1 to 2:1 | 11:1 to 2:1 | 4:1 |
| proquinazid | 3:1 to 1:36 | 1:1 to 1:12 | 1:1 to 1:12 | 1:3 |
| prothiocarb | 9:1 to 1:18 | 3:1 to 1:6 | 3:1 to 1:3 | 1:1 |
| prothioconazole | 6:1 to 1:18 | 2:1 to 1:6 | 1:1 to 1:5 | 1:2 |
| pyraclostrobin | 9:1 to 1:18 | 3:1 to 1:6 | 2:1 to 1:4 | 1:1 |
| pyrametostrobin | 9:1 to 1:18 | 3:1 to 1:6 | 2:1 to 1:4 | 1:1 |
| pyraoxystrobin | 9:1 to 1:18 | 3:1 to 1:6 | 2:1 to 1:4 | 1:1 |
| pyrazophos | 150:1 to 1:36 | 50:1 to 1:12 | 15:1 to 1:1 | 4:1 |
| pyribencarb | 15:1 to 1:6 | 5:1 to 1:2 | 4:1 to 1:2 | 1:1 |
| pyrifenox | 15:1 to 1:9 | 5:1 to 1:3 | 3:1 to 1:3 | 1:1 |
| pyrimethanil | 30:1 to 1:6 | 10:1 to 1:2 | 3:1 to 1:2 | 1:1 |
| pyriofenone | 6:1 to 1:12 | 2:1 to 1:4 | 2:1 to 1:4 | 1:1 |
| pyroquilon | 15:1 to 1:9 | 5:1 to 1:3 | 3:1 to 1:3 | 1:1 |
| pyrrolnitrin | 150:1 to 1:36 | 50:1 to 1:12 | 15:1 to 2:1 | 5:1 |
| quinconazole | 4:1 to 1:12 | 1:1 to 1:4 | 1:1 to 1:4 | 1:2 |
| quinomethionate | 150:1 to 1:36 | 50:1 to 1:12 | 15:1 to 2:1 | 5:1 |
| quinoxyfen | 4:1 to 1:18 | 1:1 to 1:6 | 1:1 to 1:6 | 1:2 |
| quintozene | 150:1 to 1:36 | 50:1 to 1:12 | 15:1 to 2:1 | 5:1 |
| silthiofam | 7:1 to 1:18 | 2:1 to 1:6 | 2:1 to 1:4 | 1:1 |
| simeconazole | 15:1 to 1:36 | 5:1 to 1:12 | 1:1 to 1:5 | 1:2 |
| spiroxamine | 22:1 to 1:4 | 7:1 to 1:2 | 5:1 to 1:2 | 2:1 |
| streptomycin | 15:1 to 1:9 | 5:1 to 1:3 | 3:1 to 1:3 | 1:1 |
| sulfur | 300:1 to 3:1 | 100:1 to 9:1 | 75:1 to 9:1 | 25:1 |
| tebuconazole | 7:1 to 1:18 | 2:1 to 1:6 | 1:1 to 1:5 | 1:2 |
| tebufloquin | 100:1 to 1:100 | 10:1 to 1:10 | 3:1 to 1:3 | 1:1 |
| tecloftalam | 150:1 to 1:36 | 50:1 to 1:12 | 15:1 to 2:1 | 5:1 |
| tecnazene | 150:1 to 1:36 | 50:1 to 1:12 | 15:1 to 2:1 | 5:1 |
| terbinafine | 150:1 to 1:36 | 50:1 to 1:12 | 15:1 to 2:1 | 5:1 |
| tetraconazole | 15:1 to 1:36 | 5:1 to 1:12 | 1:1 to 1:5 | 1:2 |
| thiabendazole | 45:1 to 1:4 | 15:1 to 1:2 | 11:1 to 2:1 | 4:1 |
| thifluzamide | 15:1 to 1:9 | 5:1 to 1:3 | 3:1 to 1:3 | 1:1 |
| thiophanate | 45:1 to 1:3 | 15:1 to 2:1 | 11:1 to 2:1 | 4:1 |
| thiophanate-methyl | 45:1 to 1:3 | 15:1 to 2:1 | 11:1 to 2:1 | 4:1 |
| thiram | 150:1 to 1:2 | 50:1 to 2:1 | 37:1 to 5:1 | 14:1 |
| tiadinil | 12:1 to 1:9 | 4:1 to 1:3 | 2:1 to 1:3 | 1:1 |
| tolclofos-methyl | 150:1 to 1:2 | 50:1 to 2:1 | 37:1 to 5:1 | 14:1 |
| tolylfluanid | 150:1 to 1:36 | 50:1 to 1:12 | 15:1 to 2:1 | 5:1 |
| triadimefon | 15:1 to 1:36 | 5:1 to 1:12 | 1:1 to 1:5 | 1:2 |
| triadimenol | 15:1 to 1:36 | 5:1 to 1:12 | 1:1 to 1:5 | 1:2 |
| triarimol | 3:1 to 1:90 | 1:1 to 1:30 | 1:2 to 1:24 | 1:7 |
| triazoxide | 150:1 to 1:36 | 50:1 to 1:12 | 15:1 to 2:1 | 5:1 |
| tricyclazole | 15:1 to 1:9 | 5:1 to 1:3 | 3:1 to 1:3 | 1:1 |
| tridemorph | 30:1 to 1:3 | 10:1 to 1:1 | 7:1 to 1:1 | 2:1 |
| trifloxystrobin | 6:1 to 1:18 | 2:1 to 1:6 | 2:1 to 1:4 | 1:1 |
| triflumizole | 15:1 to 1:9 | 5:1 to 1:3 | 3:1 to 1:3 | 1:1 |
| triforine | 15:1 to 1:9 | 5:1 to 1:3 | 3:1 to 1:3 | 1:1 |
| trimorphamide | 45:1 to 1:9 | 15:1 to 1:3 | 7:1 to 1:2 | 2 1 |
| triticonazole | 15:1 to 1:36 | 5:1 to 1:12 | 1:1 to 1:5 | 12 |
| uniconazole | 15:1 to 1:36 | 5:1 to 1:12 | 1:1 to 1:5 | 12 |
| validamycin | 150:1 to 1:36 | 50:1 to 1:12 | 3:1 to 1:3 | 1 1 |
| valifenalate | 6:1 to 1:18 | 2:1 to 1:6 | 2:1 to 1:4 | 1 1 |
| vinclozolin | 120:1 to 1:2 | 40:1 to 2:1 | 15:1 to 2:1 | 6 1 |
| zineb | 150:1 to 1:2 | 50:1 to 2:1 | 37:1 to 5:1 | 14:1 |
| ziram | 150:1 to 1:2 | 50:1 to 2:1 | 37:1 to 5:1 | 14:1 |
| zoxamide | 6:1 to 1:18 | 2:1 to 1:6 | 2:1 to 1:4 | 1:1 |
| 5-chloro-6-(2,4,6-trifluorophenyl)-7-(4-methylpiperidin-1-yl)[1,2,4]triazolo[1,5-a]pyrimidine | 15:1 to 1:36 | 5:1 to 1:12 | 1:1 to 1:6 | 1:2 |
| N-[2-[4-[[3-(4-chlorophenyl)-2-propyn-1-yl]oxy]-3-methoxyphenyl]ethyl]-3-methyl-2-[(methylsulfonyl)amino]butanamide | 6:1 to 1:18 | 2:1 to 1:6 | 2:1 to 1:4 | 1:1 |
| N-[2-[4-[[3-(4-chlorophenyl)-2-propyn-1-yl]oxy]-3-methoxyphenyl]ethyl]-3-methyl-2-[(ethylsulfonyl)amino]butanamide | 6:1 to 1:18 | 2:1 to 1:6 | 2:1 to 1:4 | 1:1 |
| 2-butoxy-6-iodo-3-propyl-4H-1-benzopyran-4-one | 3:1 to 1:36 | 1:1 to 1:12 | 1:1 to 1:12 | 1:3 |
| 3-[5-(4-chlorophenyl)-2,3-dimethyl-3-isoxazolidinyl]pyridine | 15:1 to 1:9 | 5:1 to 1:3 | 3:1 to 1:3 | 1:1 |
| N'-[4-[[3-[(4-chlorophenyl)methyl]-1,2,4-thiadiazol-5-yl]oxy]-2,5-dimethylphenyl]-N-ethyl-N-methylmethanimidamide | 20:1 to 1:20 | 8:1 to 1:8 | 3:1 to 1:3 | 1:1 |
| 4-fluorophenyl N-[1-[[[1-(4-cyanophenyl)-ethyl]sulfonyl]methyl]propyl]carbamate | 6:1 to 1:18 | 2:1 to 1:6 | 2:1 to 1:4 | 1:1 |

TABLE C-continued

| Component (c) | Typical Weight Ratio | More Typical Weight Ratio | Most Typical Weight Ratio | Illustrative Weight Ratio |
|---|---|---|---|---|
| N-[[(cyclopropylmethoxy)amino][6-(difluoromethoxy)-2,3-difluorophenyl]-methylene]benzeneacetamide | 1:1 to 1:90 | 1:2 to 1:30 | 1:2 to 1:24 | 1:7 |
| α-[methoxyimino]-N-methyl-2-[[[1-[3-(trifluoromethyl)phenyl]ethoxy]imino]-methyl]benzeneacetamide | 9:1 to 1:18 | 3:1 to 1:6 | 3:1 to 1:3 | 1:1 |
| N'-[4-[4-chloro-3-(trifluoromethyl)phenoxy]-2,5-dimethylphenyl]-N-ethyl-N-methylmethanimidamide | 15:1 to 1:18 | 5:1 to 1:6 | 3:1 to 1:3 | 1:1 |
| N-(4-chloro-2-nitrophenyl)-N-ethyl-4-methylbenzenesulfonamide | 15:1 to 1:18 | 5:1 to 1:6 | 3:1 to 1:3 | 1:1 |
| 2-[[[3-(2,6-dichlorophenyl)-1-methyl-2-propen-1-ylidene]amino]oxy]methyl]-α-(methoxyimino)-N-methylbenzeneacetamide | 9:1 to 1:18 | 3:1 to 1:6 | 3:1 to 1:3 | 1:1 |
| pentyl N-[4-[[[[(1-methyl-1H-tetrazol-5-yl)-phenylmethylene]amino]oxy]methyl]-2-thiazolyl]carbamate | 9:1 to 1:18 | 3:1 to 1:6 | 3:1 to 1:3 | 1:1 |
| pentyl N-[6-[[[[(1-methyl-1H-tetrazol-5-yl)-phenylmethylene]amino]oxy]methyl]-2-pyridinyl]carbamate | 9:1 to 1:18 | 3:1 to 1:6 | 3:1 to 1:3 | 1:1 |
| 2-[(3-bromo-6-quinolinyl)oxy]-N-(1,1-dimethyl-2-butyn-1-yl)-2-(methylthio)acetamide | 5:1 to 1:22 | 2:1 to 1:8 | 2:1 to 1:4 | 1:1 |
| 2-[(3-ethynyl-6-quinolinyl)oxy]-N-[1-(hydroxymethyl)-1-methyl-2-propyn-1-yl]-2-(methylthio)acetamide | 5:1 to 1:22 | 2:1 to 1:8 | 2:1 to 1:4 | 1:1 |
| N-(1,1-dimethyl-2-butyn-1-yl)-2-[(3-ethynyl-6-quinolinyl)oxy]-2-(methylthio)acetamide | 5:1 to 1:22 | 2:1 to 1:8 | 2:1 to 1:4 | 1:1 |

The particular weight ratios defining the weight ratio ranges in Table C constitute disclosure of specific weight ratios. Table C also specifically discloses an additional illustrative weight ratio. Illustrative of specific combinations of components (a), (b) and (c) in the compositions of the present invention are specific combinations and weight ratios of components (a) and (b) listed in Tables B1 through B13 further combined with particular component (c) fungicidal compounds in the specific weight ratios disclosed in Table C.

Formulation/Utility

A compound selected from compounds of Formula 1, N-oxides, and salts thereof, or a mixture (i.e. composition) comprising the compound with (b) at least one fungicidal compound selected from (b1) through (b13) and salts thereof as described in the Summary of the Invention, will generally be used to provide fungicidal active ingredients in further compositions, i.e. formulations, with at least one additional component selected from the group consisting of surfactants, solid diluents and liquid diluents, which serves as a carrier. The formulation or composition ingredients are selected to be consistent with the physical properties of the active ingredients, mode of application and environmental factors such as soil type, moisture and temperature.

The mixtures of component (a) (i.e. at least one compound of Formula 1, N-oxides, or salts thereof) with component (b) (e.g., selected from (b1) to (b13) and salts thereof as described above) and/or one or more other biologically active compounds or agents (i.e. insecticides, other fungicides, nematocides, acaricides, herbicides and other biological agents) can be formulated in a number of ways, including:

(i) component (a), component (b) and optionally (c) one or more other biologically active compounds or agents can be formulated separately and applied separately or applied simultaneously in an appropriate weight ratio, e.g., as a tank mix; or (ii) component (a), component (b) and optionally (c) one or more other biologically active compounds or agents can be formulated together in the proper weight ratio.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Of note is a composition embodiment wherein granules of a solid composition comprising a compound of Formula 1 (or an N-oxide or salt thereof) is mixed with granules of a solid composition comprising component (b). These mixtures can be further mixed with granules comprising one or more additional biologically active compounds or agents, e.g., additional agricultural protectants. Alternatively, two or more agricultural protectants (e.g., a component (a) (Formula 1) compound, a component (b) compound, (c) an agricultural protectant other than component (a) or (b)) can be combined in the solid composition of one set of granules, which is then mixed with one or more sets of granules of solid compositions comprising one or more additional agricultural protectants. These granule mixtures can be in accordance with the general granule mixture disclosure of PCT Patent Publication WO 94/24861 or more preferably the homogeneous granule mixture teaching of U.S. Pat. No. 6,022,552.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compounds of Formula 1 and other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

Without further elaboration, it is believed that one skilled in the art using the preceding formulation description can utilize the present invention to its fullest extent. The following Examples of formulation are, therefore, to be construed as merely illustrative, and not limiting of the disclosure in any way whatsoever. Percentages are by weight, and all formulations are prepared in conventional ways. Compound numbers refer to compounds in Index Table A. The component designations refer to the corresponding compounds indicated in the Component (b) column of Table A1. For example, "Component (b1a)" refers to 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone.

Example A

| High Strength Concentrate | |
|---|---|
| Any one of Compounds 1, 2, 3, 4, 5, 6, 7, 8, 9, 10, 11 and 12 | 93.8% |
| Component (b1a) | 4.7% |
| silica aerogel | 0.5% |
| synthetic amorphous fine silica | 1.0% |

Example B

Wettable Powder

| | |
|---|---|
| Any one of Compounds 1, 2, 3, 4, 5, 6, 7, 8, 9, 10, 11 and 12 | 59.1% |
| Component (b3a) | 5.9% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| Any one of Compounds 1, 2, 3, 4, 5, 6, 7, 8, 9, 10, 11 and 12 | 5.0% |
| Component (b4a) | 5.0% |
| attapulgite granules (low volatile matter, 0.71/0.30 mm; U.S.S. No. 25-50 sieves) | 90.0% |

Example D

Extruded Pellet

| | |
|---|---|
| Any one of Compounds 1, 2, 3, 4, 5, 6, 7, 8, 9, 10, 11 and 12 | 16.7% |
| Component (b5) | 8.3% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Any one of Compounds 1, 2, 3, 4, 5, 6, 7, 8, 9, 10, 11 and 12 | 6.7% |
| Component (b6a) | 3.3% |
| polyoxyethylene sorbitol hexoleate | 20.0% |
| $C_6$-$C_{10}$ fatty acid methyl ester | 70.0% |

Example F

Microemulsion

| | |
|---|---|
| Any one of Compounds 1, 2, 3, 4, 5, 6, 7, 8, 9, 10, 11 and 12 | 2.5% |
| Component (b7) | 2.5% |
| polyvinylpyrrolidone-vinyl acetate copolymer | 30.0% |
| alkylpolyglycoside | 30.0% |
| glyceryl monooleate | 15.0% |
| water | 20.0% |

Example G

High Strength Concentrate

| | |
|---|---|
| Any one of Compounds 1, 2, 3, 4, 5, 6, 7, 8, 9, 10, 11 and 12 | 49.3% |
| Component (b8) | 49.2% |
| silica aerogel | 0.5% |
| synthetic amorphous fine silica | 1.0% |

Example H

Granule

| | |
|---|---|
| Any one of Compounds 1, 2, 3, 4, 5, 6, 7, 8, 9, 10, 11 and 12 | 5.0% |
| Component (b9a) | 5.0% |
| attapulgite granules (low volatile matter, 0.71/0.30 mm; U.S.S. No. 25-50 sieves) | 90.0% |

Example I

Extruded Pellet

| | |
|---|---|
| Any one of Compounds 1, 2, 3, 4, 5, 6, 7, 8, 9, 10, 11 and 12 | 12.5% |
| Component (b10a) | 12.5% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example J

Emulsifiable Concentrate

| | |
|---|---|
| Any one of Compounds 1, 2, 3, 4, 5, 6, 7, 8, 9, 10, 11 and 12 | 5.0% |
| Component (b11) | 5.0% |
| polyoxyethylene sorbitol hexoleate | 20.0% |
| $C_6$-$C_{10}$ fatty acid methyl ester | 70.0% |

Example K

Seed Treatment

| | |
|---|---|
| Any one of Compounds 1, 2, 3, 4, 5, 6, 7, 8, 9, 10, 11 and 12 | 1.05% |
| Component (b12) | 18.95% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example L

Wettable Powder

| | |
|---|---|
| Any one of Compounds 1, 2, 3, 4, 5, 6, 7, 8, 9, 10, 11 and 12 | 41.9% |
| Component (b1a) | 2.1% |

-continued

| Wettable Powder | |
|---|---|
| prothioconazole | 21.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example M

| Emulsifiable Concentrate | |
|---|---|
| Any one of Compounds 1, 2, 3, 4, 5, 6, 7, 8, 9, 10, 11 and 12 | 5.0% |
| Component (b13) | 5.0% |
| polyoxyethylene sorbitol hexoleate | 20.0% |
| $C_6$-$C_{10}$ fatty acid methyl ester | 70.0% |

As already mentioned, combinations of components (a), (b) and optionally (c) can be together or separately formulated with at least one of a surfactant, a solid diluent or a liquid diluent. Thus one, two or all three of components (a), (b) and (c) can be formulated together to form a premix composition, or they can be formulated separately and then the formulated compositions combined together before application (e.g., in a spray tank) or, alternatively, applied in succession. In the formulated compositions containing components (a), (b) or (c), the components (a), (b) or (c) are present in biologically effective amounts, or more particularly, for example, fungicidally effective amounts if they are fungicidal or insecticidally effective amounts if they are insecticidal.

Formulations are often diluted with water to form aqueous compositions before application. Aqueous compositions for direct applications to the plant or portion thereof (e.g., spray tank compositions) typically comprise at least about 1 ppm or more (e.g., from 1 ppm to 100 ppm) of fungicidally active compounds according to the present invention.

The compositions of this invention are useful as plant disease control agents. The present invention therefore further comprises a method for controlling plant diseases caused by fungal plant pathogens comprising applying to the plant or portion thereof to be protected, or to the plant seed or vegetative propagation unit to be protected, an effective amount of a composition of the invention (e.g., a composition comprising component (a), or components (a) and (b), or components (a), (b) and (c)). This aspect of the present invention can also be described as a method for protecting a plant or plant seed from diseases caused by fungal pathogens comprising applying a fungicidally effective amount of a composition of the invention to the plant (or portion thereof) or plant seed (directly or through the environment (e.g., growing medium) of the plant or plant seed).

Component (a) compounds and/or combinations thereof with component (b) compounds and/or (c) one or more other biologically active compounds or agents can be applied to plants genetically transformed to express proteins toxic to invertebrate pests (such as *Bacillus thuringiensis* delta-endotoxins). The effect of the exogenously applied present component (a) alone or in combination with component (b) and optionally component (c) may be synergistic with the expressed toxin proteins.

Plant disease control is ordinarily accomplished by applying an effective amount of a composition of the invention (e.g., comprising component (a), or a mixture of components (a), (b) and optionally (c)), typically as a formulated composition, either pre- or post-infection, to the portion of the plant to be protected such as the roots, stems, foliage, fruit, seeds, tubers or bulbs, or to the media (soil or sand) in which the plants to be protected are growing. Component (a) or mixtures thereof can also be applied to seeds to protect the seeds and seedlings developing from the seeds. The mixtures can also be applied through irrigation water to treat plants. Control of postharvest pathogens which infect the produce before harvest is typically accomplished by field application of a composition of the invention, and in cases where infection occurs after harvest the compositions can be applied to the harvested crop as dips, sprays, fumigants, treated wraps or box liners.

Suitable rates of application (e.g., fungicidally effective amounts) of component (a) (i.e. at least one compound selected from compounds of Formula 1, N-oxides and salts thereof) as well as suitable rates of application (e.g., biologically effective amounts, fungicidally effective amounts or insecticidally effective amounts) of components (b) and optionally (c) according to this invention can be influenced by many factors of the environment and should be determined under actual use conditions. Foliage can normally be protected when treated at a rate of from less than about 1 g/ha to about 5,000 g/ha of active ingredients. Seed and seedlings can normally be protected when seed is treated at a rate of from about 0.1 to about 10 g per kilogram of seed; and vegetative propagation units (e.g., cuttings and tubers) can normally be protected when propagation unit is treated at a rate of from about 0.1 to about 10 g per kilogram of propagation unit. One skilled in the art can easily determine through simple experimentation the application rates of component (a), and mixtures and compositions thereof, containing particular combinations of active ingredients according to this invention needed to provide the desired spectrum of plant protection and control of plant diseases and optionally other plant pests.

The compounds of Formula 1, N-oxides, and salts thereof, are particularly efficacious for controlling plant diseases caused by fungal pathogens, particularly in the Basidomycete and Ascomycete classes. Combining these compounds with other fungicidal compounds can provide control of diseases caused by a broad spectrum of fungal plant pathogens in the Basidiomycete, Ascomycete, Oomycete and Deuteromycete classes. Accordingly, mixtures and compositions described herein can control a broad spectrum of plant diseases, foliar pathogens of crops including: cereal grain crops such as wheat, barley, oats, rye, triticale, rice, maize, sorghum and millet; vine crops such as table and wine grapes; field crops such as oilseed rape (canola), sunflower; sugar beets, sugar cane, soybean, peanuts (groundnut), tobacco, alfalfa, clover, lespedeza, trefoil and vetch; pome fruits such as apple, pear, crabapple, loquat, mayhaw and quince; stone fruits such as peaches, cherries, plums, apricots, nectarines and almonds; citrus fruits such as lemons, limes, oranges, grapefruit, mandarin (tangerines) and kumquat; root and tuber vegetables and field crops (and their foliage) such as artichoke, garden and sugar beet, carrot, cassava, ginger, ginseng, horseradish, parsnip, potato, radish, rutabaga, sweet potato, turnip and yam; bulb vegetables such as garlic, leek, onion and shallot; leafy vegetables such as arugula (roquette), celery, celery, cress, endive (escarole), fennel, head and leaf lettuce, parsley, radicchio (red chicory), rhubarb, spinach and Swiss chard; brassica (cole) leafy vegetables such as broccoli, broccoli raab (rapini), Brussels sprouts, cabbage, bok Choy, cauliflower, collards, kale, kohlrabi, mustard and greens; legume vegetables (succulent or dried) such as lupin, bean (*Phaseolus* spp.) (including field bean, kidney bean, lima bean, navy bean, pinto bean, runner bean, snap bean, tepary bean and wax bean), bean (*Vigna* spp.) (including adzuki bean, asparagus bean, blackeyed pea, catjang, Chinese longbean, cowpea, crowder pea, moth bean, mung bean, rice bean, southern pea, urd bean and yardlong bean), broad bean (fava), chickpea (garbanzo), guar, jackbean, lablab bean, lentil and pea (*Pisum* spp.) (including dwarf pea, edible-podded pea, English pea, field pea, garden pea, green pea, snowpea, sugar snap pea, pigeon pea and soybean); fruiting vegetables such as eggplant, groundcherry (*Physalis* spp.), pepino and pepper (including bell pepper, chili pepper, cooking pepper, pimento, sweet pepper; tomatillo and tomato); cucurbit vegetables such as Chayote (fruit), Chinese waxgourd (Chinese preserving melon), citron melon, cucumber, gherkin, edible gourd (including hyotan, cucuzza, hechima, and Chinese okra), *Momordica* spp. (including balsam apple, balsam pear, bittermelon and Chinese cucumber), muskmelon (including cantaloupe and pumpkin), summer and winter squash (including butternut squash, calabaza, hubbard squash, acorn squash, spaghetti squash) and watermelon; berries such as blackberry (including bingleberry, boysenberry, dewberry, lowberry, marionberry, olallieberry and youngberry), blueberry, cranberry, currant, elderberry, gooseberry, huckleberry, loganberry, raspberry and strawberry; tree nuts such as almond, beech nut, Brazil nut, butternut, cashew, chestnut, chinquapin, filbert (hazelnut), hickory nut, macadamia nut, pecan and walnut; tropical fruits and other crops such as bananas, plantains, mangos, coconuts, papaya, guava, avocado, lichee, agave, coffee, cacao, sugar cane, oil palm, sesame, rubber and spices; fiber crops such as cotton, flax and hemp; turfgrasses (including warm- and cool-season turfgrasses) such as bentgrass, Kentucky bluegrass, St. Augustine grass, tall fescue and Bermuda grass.

These pathogens include: Oomycetes, including *Phytophthora* pathogens such as *Phytophthora infestans*, *Phytophthora megasperma*, *Phytophthora parasitica*, *Phytophthora cinnamomi* and *Phytophthora capsici*, *Pythium* pathogens such as *Pythium aphanidermatum*, and pathogens in the Peronosporaceae family such as *Plasmopara viticola*, *Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* pathogens such as *Alternaria solani* and *Alternaria brassicae*, *Guignardia* pathogens such as *Guignardia bidwelli*, *Venturia* pathogens such as *Venturia inaequalis*, *Septoria* pathogens such as *Septoria nodorum* and *Septoria tritici*, powdery mildew disease pathogens such as *Blumeria* spp. (including *Blumeria graminis*) and *Erysiphe* spp. (including *Erysiphe polygoni*), *Uncinula necatur*, *Sphaerotheca fuliginea* and *Podosphaera leucotricha*, *Pseudocercosporella herpotrichoides*, *Botrytis* pathogens such as *Botrytis cinerea*, *Monilinia fructicola*, *Sclerotinia* pathogens such as *Sclerotinia sclerotiorum* and *Sclerotinia minor*, *Magnaporthe grisea*, *Phomopsis viticola*, *Helminthosporium* pathogens such as *Helminthosporium tritici repentis*, *Pyrenophora teres*, anthracnose disease pathogens such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondita*, *Puccinia striiformis*, *Puccinia hordei*, *Puccinia graminis* and *Puccinia arachidis*), *Hemileia vastatrix* and *Phakopsora pachyrhizi*; other pathogens including *Rhizoctonia* spp. (such as *Rhizoctonia solani* and *Rhizoctonia oryzae*); *Fusarium* pathogens such as *Fusarium roseum*, *Fusarium graminearum* and *Fusarium oxysporum*; *Verticillium dahliae*; *Sclerotium rolfsii*; *Rynchosporium secalis*; *Cercosporidium personatum*, *Cercospora arachidicola* and *Cercospora beticola*; *Rutstroemia floccosum* (also known as *Sclerontina homoeocarpa*); *Rhizopus* spp. (such as *Rhizopus stolonifer*); *Aspergillus* spp. (such as *Aspergillus flavus* and *Aspergillus parasiticus*); and other genera and species closely related to these pathogens. Commonly, pathogens are referred to as diseases, and thus in the preceding sentence the word "pathogen" also refers to the plant disease caused by the pathogen. More precisely, plant diseases are caused by pathogens. Therefore, for example, powdery mildew diseases are plant diseases caused by powdery mildew pathogens, *Septoria* diseases are plant diseases caused by *Septoria* pathogens, and rust diseases are plant diseases caused by rust disease pathogens. Certain fungicidal compounds are also bactericidal, and therefore in addition to their fungicidal activity, the compositions or combinations can also have activity against bacteria such as *Erwinia amylovora*, *Xanthomonas campestris*, *Pseudomonas syringae*, and other related species. Furthermore, compounds of Formula 1 and their mixtures and compositions according to this invention are useful in treating postharvest diseases of fruits and vegetables caused by fungi and bacteria. These infections can occur before, during and after harvest. For example, infections can occur before harvest and then remain dormant until some point during ripening (e.g., host begins tissue changes in such a way that infection can progress); also infections can arise from surface wounds created by mechanical or insect injury. In this respect, application of compounds, mixtures and compositions according to this invention can reduce losses (i.e. losses resulting from quantity and quality) due to postharvest diseases which may occur at any time from harvest to consumption. Treatment of postharvest diseases with compounds of the invention can increase the period of time during which perishable edible plant parts (e.g., fruits, seeds, foliage, stems, bulbs, tubers) can be stored refrigerated or unrefrigerated after harvest, and remain edible and free from noticeable or harmful degradation or contamination by fungi or other microorganisms. Treatment of edible plant parts before or after harvest with compounds, mixtures or compositions according to this invention can also decrease the formation of toxic metabolites of fungi or other microorganisms, for example, mycotoxins such as aflatoxins.

In the present fungicidal compositions, the Formula 1 compounds of component (a) can work synergically with the additional fungicidal compounds of component (b) to provide such beneficial results as broadening the spectrum of plant diseases controlled, extending duration of preventative and curative protection, and suppressing proliferation of resistant fungal pathogens. In particular embodiments, compositions are provided in accordance with this invention that comprise proportions of component (a) and component (b) that are especially useful for controlling particular fungal diseases (such as *Alternaria solani*, *Blumeria graminis* f. sp. *tritici*, *Botrytis cinerea*, *Puccinia recondita* f. sp. *tritici*, *Rhizoctonia solani*, *Septoria nodorum*, *Septoria tritici*).

Mixtures of fungicides may also provide significantly better disease control than could be predicted based on the activity of the individual components. This synergism has been described as "the cooperative action of two components of a mixture, such that the total effect is greater or more prolonged than the sum of the effects of the two (or more) taken independently" (see P. M. L. Tames, *Neth. J. Plant Pathology* 1964, 70, 73-80). In methods providing plant disease control in which synergy is exhibited from a combination of active ingredients (e.g., fungicidal compounds) applied to the plant or seed, the active ingredients are applied in a synergistic weight ratio and synergistic (i.e. synergistically effective) amounts. Measures of disease control, inhibition and prevention cannot exceed 100%. Therefore expression of substantial synergism typically requires use of application rates of active ingredients wherein the active ingredients separately provide much less than 100% effect, so that their additive effect is substantially less than 100% to allow the possibility of an increase in effect as result of synergism. On the other hand, application rates of active ingredients that are too low may show not show much activity in mixtures even with the benefit of synergism. One skilled in the art can easily identify and optimize through simple experimentation the weight ratios and application rates (i.e. amounts) of fungicidal compounds providing synergy.

The following Tests include tests demonstrating the efficacy of compounds of Formula 1 for controlling specific pathogens; this efficacy is thus provided to fungicidal mixtures comprising these compounds. The disease control afforded by the present compounds alone or in mixtures is not limited, however, to the pathogenic fungi species exemplified.

See Index Table A for compound descriptions. See Index Table B for melting point data. The abbreviation "Cmpd." stands for "Compound", and the abbreviation "Ex." stands for "Example" and is followed by a number indicating in which Synthesis Example the compound is prepared. Mass spectra (M.S.) are reported as the molecular weight of the highest isotopic abundance parent ion (M+1) formed by addition of H$^+$ (molecular weight of 1) to the molecule, observed by mass spectrometry using atmospheric pressure chemical ionization (AP$^+$). The presence of molecular ions containing one or more higher atomic weight isotopes of lower abundance (e.g., $^{37}$Cl, $^{81}$Br) is not reported.

INDEX TABLE A

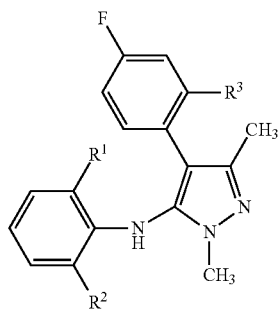

| Cmpd No. | R$^1$ | R$^2$ | R$^3$ | M.S. |
|---|---|---|---|---|
| 1 | F | H | Cl | 334 |
| 2 | F | F | Cl | 352 |
| 3 | Cl | F | Cl | * |
| 4 (Ex. 1) | Cl | F | Br | 414 |
| 5 | Br | F | Cl | 414 |
| 6 | Br | H | Br | 440 |
| 7 | Br | F | Br | * |
| 8 | Cl | H | Br | 396 |
| 9 | Br | H | Cl | 396 |
| 10 | Cl | H | Cl | 350 |
| 11 (Ex. 2) | F | F | Br | * |
| 12 | F | H | Br | |

*Melting Point (MP) data are listed in Index Table B.

INDEX TABLE B

| CmpdNo. | Melting Point[a] | Cmpd No. | Melting Point | Cmpd No. | Melting Point |
|---|---|---|---|---|---|
| 3 | 166-168 | 7 | 154-156 | 11 | 134-136 |

[a]Melting point data are ° C.

Biological Examples of the Invention

General protocol for preparing test suspensions for Tests A-I: the test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-I. Each test was conducted in triplicate, and the results were averaged. Spraying a 200 ppm test suspension to the point of run-off on the test plants was the equivalent of a rate of about 800 g/ha. Unless otherwise indicated, the rating values indicate a 200 ppm test suspension was used. (An asterisk "*" next to the rating value indicates a 40 ppm test suspension was used.)

Test A

The test suspension was sprayed to the point of run-off on tomato seedlings. The following day the seedlings were inoculated with a spore suspension of *Botrytis cinerea* (the causal agent of tomato *Botrytis*) and incubated in saturated atmosphere at 20° C. for 48 h, and then moved to a growth chamber at 24° C. for 3 additional days, after which time visual disease ratings were made.

Test B

The test suspension was sprayed to the point of run-off on tomato seedlings. The following day the seedlings were inoculated with a spore suspension of *Alternaria solani* (the causal agent of tomato early blight) and incubated in a saturated atmosphere at 27° C. for 48 h, and then moved to a growth chamber at 20° C. for 5 days, after which time visual disease ratings were made.

Test C

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 5 days, after which time visual disease ratings were made.

Test D

The test suspension was sprayed to the point of run-off on creeping bent grass (*Agrostis* sp.) seedlings. The following day the seedlings were inoculated with a bran and mycelial slurry of *Rhizoctonia solani* (the causal agent of turf brown patch) and incubated in a saturated atmosphere at 27° C. for 48 h, and then moved to a growth chamber at 27° C. for 3 days, after which time disease ratings were made.

Test E

The test suspension was sprayed to the point of run-off on wheat seedlings. The following day the seedlings were inoculated with a spore suspension of *Septoria nodorum* (the causal agent of *Septoria* glume blotch) and incubated in a saturated atmosphere at 24° C. for 48 h, and then moved to a growth chamber at 20° C. for 9 days, after which time visual disease ratings were made.

Test F

The test suspension was sprayed to the point of run-off on wheat seedlings. The following day the seedlings were inoculated with a spore suspension of *Septoria tritici* (the causal agent of wheat leaf blotch) and incubated in saturated atmosphere at 24° C. for 48 h. and then the seedlings were moved to a growth chamber at 20° C. for 19 additional days, after which time visual disease ratings were made.

Test G

Wheat seedlings were inoculated with a spore suspension of *Puccinia recondita* f. sp. *tritici* (the causal agent of wheat leaf rust) and incubated in a saturated atmosphere at 20° C. for 24 h, and then moved to a growth chamber at 20° C. for 2 days. At the end of this time the test suspension was sprayed to the point of run-off, and then the seedlings were moved to a growth chamber at 20° C. for 4 days after which time visual disease ratings were made.

Test H

The test suspension was sprayed to the point of run-off on wheat seedlings. The following day the seedlings were inoculated with a spore suspension of *Puccinia recondita* f. sp. *tritici* (the causal agent of wheat leaf rust) and incubated in a saturated atmosphere at 20° C. for 24 h, and then moved to a growth chamber at 20° C. for 6 days, after which time visual disease ratings were made.

Test I

The test suspension was sprayed to the point of run-off on wheat seedlings. The following day the seedlings were inoculated with a spore dust of *Blumeria graminis* f. sp. *tritici* (also known as *Erysiphe graminis* f. sp. *tritici*, the causal agent of wheat powdery mildew) and incubated in a growth chamber at 20° C. for 8 days, after which time visual disease ratings were made.

Results for Tests A-I are given in Table A. In the Table, a rating of 100 indicates 100% disease control and a rating of 0 indicates no disease control (relative to the controls). A hyphen (-) indicates no test results.

TABLE A

| Cmpd No. | Test A | Test B | Test C | Test D | Test E | Test F | Test G | Test H | Test I |
|---|---|---|---|---|---|---|---|---|---|
| 1 | 99 | 93 | 0 | 99 | 0 | 100 | — | 99 | 100 |
| 2 | 100 | 100 | — | — | 87 | 100 | 0 | 99 | 100 |
| 3 | 100 | 100 | 0* | — | 99 | 100 | 100 | 100 | 99 |
| 4 | 100 | — | — | — | — | 100 | — | 100 | 100 |
| 5 | 100 | — | — | — | — | 100 | — | 100 | 100 |
| 6 | 99* | — | — | — | — | 100* | — | 96* | 99* |
| 7 | 100 | — | — | — | — | 100 | — | 100 | 100 |
| 8 | 100 | — | — | — | — | 100 | — | 99 | 100 |
| 9 | 99* | — | — | — | 0* | 100* | — | 93* | 99* |

TABLE A-continued

| Cmpd No. | Test A | Test B | Test C | Test D | Test E | Test F | Test G | Test H | Test I |
|---|---|---|---|---|---|---|---|---|---|
| 10 | 100* | — | — | — | 0* | 100* | — | 98* | 100* |
| 11 | 100* | — | — | — | 60* | 100* | — | 98* | 100* |

"Cmpd No." means compound number.

The test results presented in Table A for compounds of Formula 1 illustrate the fungicidal activity of component (a) contributing to the plant disease control utility of compositions comprising component (a) in combination with component (b) and optionally component (c) according to the present invention.

What is claimed is:

1. A fungicidal composition comprising:
(a) the compound of Formula 1 wherein
$R^1$ is Cl, $R^2$ is F and $R^3$ is Br;
and
(b) at least one fungicidal compound selected from (b1)

B1a (b2)

B2 wherein R$^{b1}$ is (b3)

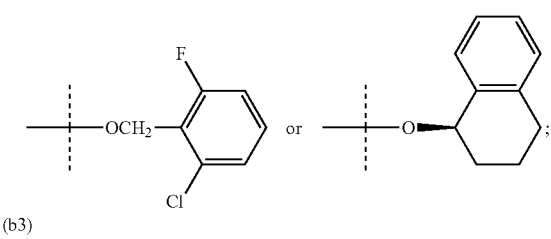 or 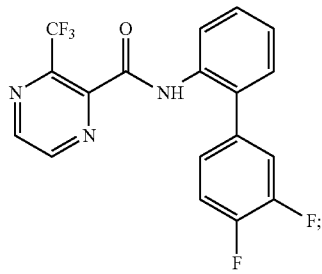;

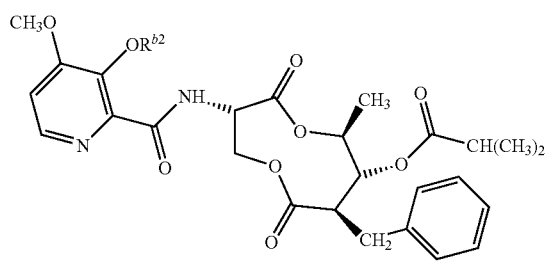

wherein R$^{b2}$ is —CH$_2$OC(O)CH(CH$_3$)$_2$, —C(O)CH$_3$, —CH$_2$OC(O)CH$_3$, —C(O)OCH$_2$CH(CH$_3$)$_2$ or

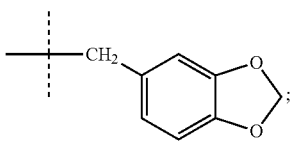;

(b4)

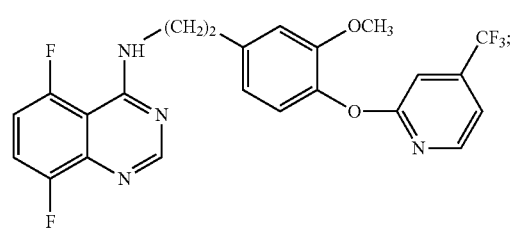

wherein R$^{b3}$ is CH$_3$ or F;

(b5)

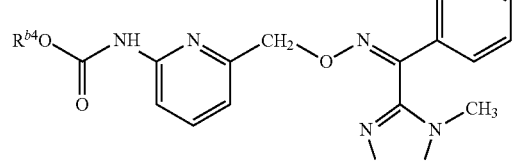

(b6)

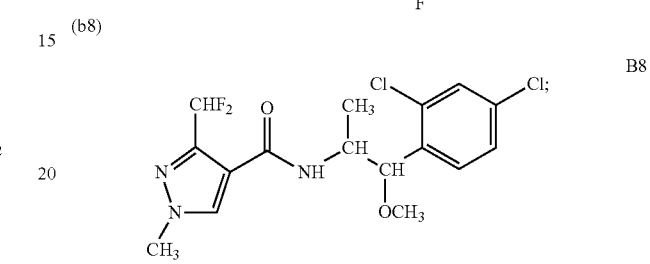

wherein R$^{b4}$ is —(CH$_2$)$_4$CH$_3$, —C(CH$_3$)$_3$ or —(CH$_2$)$_2$C≡CH;

(b7)

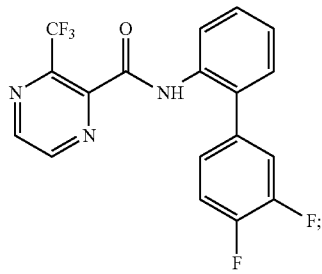

(b8)

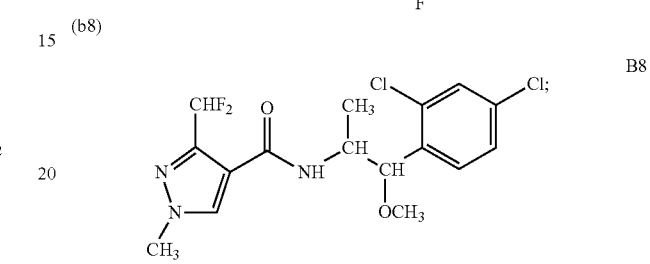

(b9)

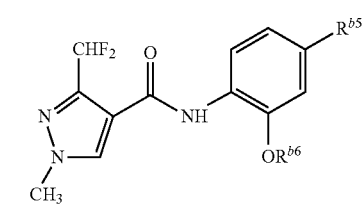

wherein R$^{b5}$ is H or F, and R$^{b6}$ is —CF$_2$CHFCF$_3$ or —CF$_2$CF$_2$H;

(b10)

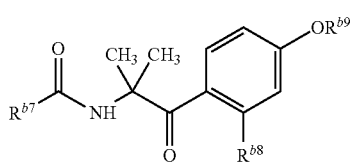

wherein R$^{b7}$ is

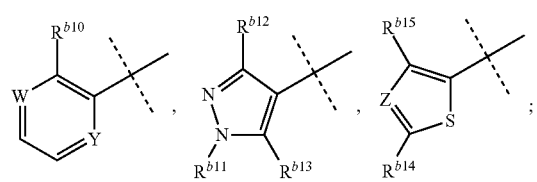

R$^{b8}$ is H, halogen or C$_1$-C$_2$ alkyl;
R$^{b9}$ is C$_1$-C$_8$ alkyl, C$_1$-C$_8$ haloalkyl or C$_2$-C$_8$ alkoxyalkyl;
R$^{b10}$ is halogen, C$_1$-C$_2$ alkyl or C$_1$-C$_2$ haloalkyl;
R$^{b11}$ is halogen, C$_1$-C$_2$ alkyl or C$_1$-C$_2$ haloalkyl;
R$^{b12}$ is C$_1$-C$_2$ alkyl;
R$^{b13}$ is H, halogen or C$_1$-C$_2$ alkyl;
R$^{b14}$ is C$_1$-C$_2$ alkyl or C$_1$-C$_2$ haloalkyl;
R$^{b15}$ is H, C$_1$-C$_2$ alkyl or C$_1$-C$_2$ haloalkyl;

W is CH or N;
Y is CH or N; and
Z is CH or N;
(b11)
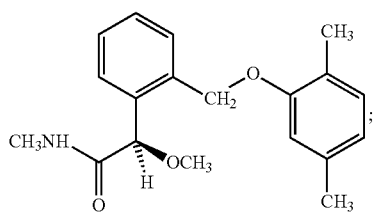
B11
(b12)
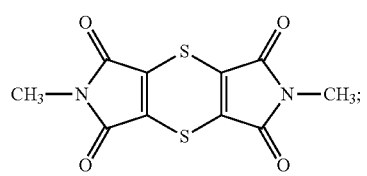
B12
and salts thereof.
2. A method for protecting a plant or plant seed from diseases caused by fungal pathogens comprising applying a fungicidally effective amount of the composition of claim 1 to the plant or plant seed.
3. A composition of claim 1 wherein the weight ratio of component (a) to component (b) is from 25:1 to 1:25.
* * * * *